(12) United States Patent
Abdu et al.

(10) Patent No.: US 12,116,629 B2
(45) Date of Patent: *Oct. 15, 2024

(54) METHODS AND COMPOSITIONS FOR REDUCING NUCLEOTIDE IMPURITIES

(71) Applicant: Singular Genomics Systems, Inc., San Diego, CA (US)

(72) Inventors: Abrehet Abdu, San Diego, CA (US); Eli N. Glezer, Del Mar, CA (US); Laura Ann Hale, Del Mar, CA (US); Jiawen Li, San Diego, CA (US)

(73) Assignee: Singular Genomics Systems, Inc., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/188,153

(22) Filed: Mar. 22, 2023

(65) Prior Publication Data

US 2023/0265505 A1    Aug. 24, 2023

Related U.S. Application Data

(63) Continuation of application No. PCT/US2021/057600, filed on Nov. 1, 2021.

(60) Provisional application No. 63/108,179, filed on Oct. 30, 2020.

(51) Int. Cl.
| | | |
|---|---|---|
| *C12Q 1/6809* | (2018.01) | |
| *B01L 3/00* | (2006.01) | |
| *C12Q 1/6806* | (2018.01) | |
| *C12Q 1/6869* | (2018.01) | |
| *C12Q 1/6874* | (2018.01) | |

(52) U.S. Cl.
CPC ...... *C12Q 1/6874* (2013.01); *B01L 3/502715* (2013.01); *C12Q 1/6806* (2013.01); *C12Q 2600/166* (2013.01)

(58) Field of Classification Search
None
See application file for complete search history.

(56) References Cited

U.S. PATENT DOCUMENTS

| | | |
|---|---|---|
| 5,763,594 A | 6/1998 | Hiatt et al. |
| 5,808,045 A | 9/1998 | Hiatt et al. |
| 5,872,244 A | 2/1999 | Hiatt et al. |
| 6,174,672 B1 | 1/2001 | Faff et al. |
| 6,232,465 B1 | 5/2001 | Hiatt et al. |
| 6,664,079 B2 | 12/2003 | Ju et al. |
| 7,057,026 B2 | 6/2006 | Barnes et al. |

(Continued)

FOREIGN PATENT DOCUMENTS

| | | |
|---|---|---|
| WO | WO-2004/018497 A2 | 3/2004 |
| WO | WO-2004/018497 A3 | 3/2004 |

(Continued)

OTHER PUBLICATIONS

Sarac, I. et al. (2019). "Terminal deoxynucleotidyl transferase in the synthesis and modification of nucleic acids," *ChemBioChem* 20(7): 860-871.

(Continued)

*Primary Examiner* — Robert T. Crow
(74) *Attorney, Agent, or Firm* — Mintz, Levin, Cohn, Ferris, Glovsky, Popeo, P.C.; Zachary L. Terranova

(57) ABSTRACT

Disclosed herein, inter alia, are compositions and methods for depleting nucleotide impurities in nucleotide solutions.

19 Claims, 7 Drawing Sheets

Specification includes a Sequence Listing.

The next correct nucleotide (G) is incorporated

The label for the G nucleotide is detected, and both the label and reversible terminator are removed

(56) References Cited

U.S. PATENT DOCUMENTS

| | | |
|---|---|---|
| 7,541,444 B2 | 6/2009 | Milton et al. |
| 8,039,817 B2 | 10/2011 | Feng et al. |
| 8,241,573 B2 | 8/2012 | Banerjee et al. |
| 9,222,132 B2 | 12/2015 | Drmanac |
| 9,453,258 B2 | 9/2016 | Kain et al. |
| 10,738,072 B1 | 8/2020 | Graham et al. |
| 10,822,653 B1 | 11/2020 | Graham et al. |
| 2001/0036629 A1* | 11/2001 | Dower ............... C12Q 1/6837 435/6.12 |
| 2003/0186288 A1 | 10/2003 | Spivack et al. |
| 2004/0023220 A1 | 2/2004 | Greenfield et al. |
| 2004/0077090 A1* | 4/2004 | Short ............... C12N 15/1027 435/254.2 |
| 2006/0199214 A1* | 9/2006 | Jack ............... C12Q 1/6869 435/6.12 |
| 2007/0009922 A1 | 1/2007 | Borns |
| 2009/0170724 A1 | 7/2009 | Balasubramanian et al. |
| 2010/0022403 A1 | 1/2010 | Kurn et al. |
| 2012/0270305 A1 | 10/2012 | Reed et al. |
| 2013/0022980 A1 | 1/2013 | Nelson et al. |
| 2013/0189743 A1* | 7/2013 | Balasubramanian ........................ C12Q 1/6834 435/183 |
| 2013/0324418 A1 | 12/2013 | Fuchs et al. |
| 2016/0097091 A1 | 4/2016 | Hinz et al. |
| 2016/0251711 A1 | 9/2016 | Amorese et al. |
| 2017/0016063 A1* | 1/2017 | McGall ............... C12N 15/1065 |
| 2017/0130051 A1 | 5/2017 | Marma et al. |
| 2017/0211141 A1 | 7/2017 | Gordon et al. |
| 2018/0023108 A1 | 1/2018 | Chen et al. |
| 2018/0119217 A1* | 5/2018 | Hinz ............... C12Q 1/6874 |
| 2018/0258472 A1 | 9/2018 | Glezer |
| 2018/0274024 A1 | 9/2018 | Ju et al. |
| 2018/0305753 A1* | 10/2018 | Chesney ............... C12N 15/1065 |
| 2019/0078126 A1* | 3/2019 | Baiga ............... C12Q 1/6806 |
| 2019/0185914 A1* | 6/2019 | Cherkasov ............ C12Q 1/6806 |
| 2019/0211315 A1* | 7/2019 | Champion ............ C12N 9/1264 |
| 2020/0069717 A1 | 3/2020 | Ju et al. |
| 2020/0190490 A1 | 6/2020 | Efcavitch et al. |

FOREIGN PATENT DOCUMENTS

| | | |
|---|---|---|
| WO | WO-2006/030455 A1 | 3/2006 |
| WO | WO-2017/058953 A1 | 4/2017 |
| WO | WO-2019/164977 A1 | 8/2019 |

OTHER PUBLICATIONS

Bentley, D. et al. (Nov. 6, 2008). "Accurate whole human genome sequencing using reversible terminator chemistry," *Nature* 456(7218): 53-59.

Beste, K. Y. et al. (Jan. 10, 2012, e-published Dec. 13, 2011). "Nucleotidyl cyclase activity of soluble guanylyl cyclase $\alpha 1\beta 1$," *Biochemistry* 51(1): 194-204.

Gardner, A. F. et al. (Aug. 1, 2012, e-published May 8, 2012). "Rapid incorporation kinetics and improved fidelity of a novel class of 3'-OH unblocked reversible terminators," Nucleic Acids Research 40(15): 7404-7415.

Hutter, D. et al. (Dec. 1, 2010). "Labeled nucleoside triphosphates with reversibly terminating aminoalkoxyl groups," *Nucleosides Nucleotides & Nucleic Acids* 29(11): 879-895.

International Search Report mailed on Mar. 7, 2022, for PCT Application No. PCT/US2021/057600, filed Nov. 1, 2021, 5 pages.

Metzker, M. et al. (Nov. 1998, e-published Aug. 15, 2018). "Elimination of residual natural nucleotides from 3'-O-modified-dNTP syntheses by enzymatic mop-up," *Biotechniques* 25(5): 814-817.

Written Opinion mailed on Mar. 7, 2022, for PCT Application No. PCT/US2021/057600, filed Nov. 1, 2021, 6 pages.

\* cited by examiner

The next correct nucleotide (G) is incorporated

The label for the G nucleotide is detected, and both the label and reversible terminator are removed

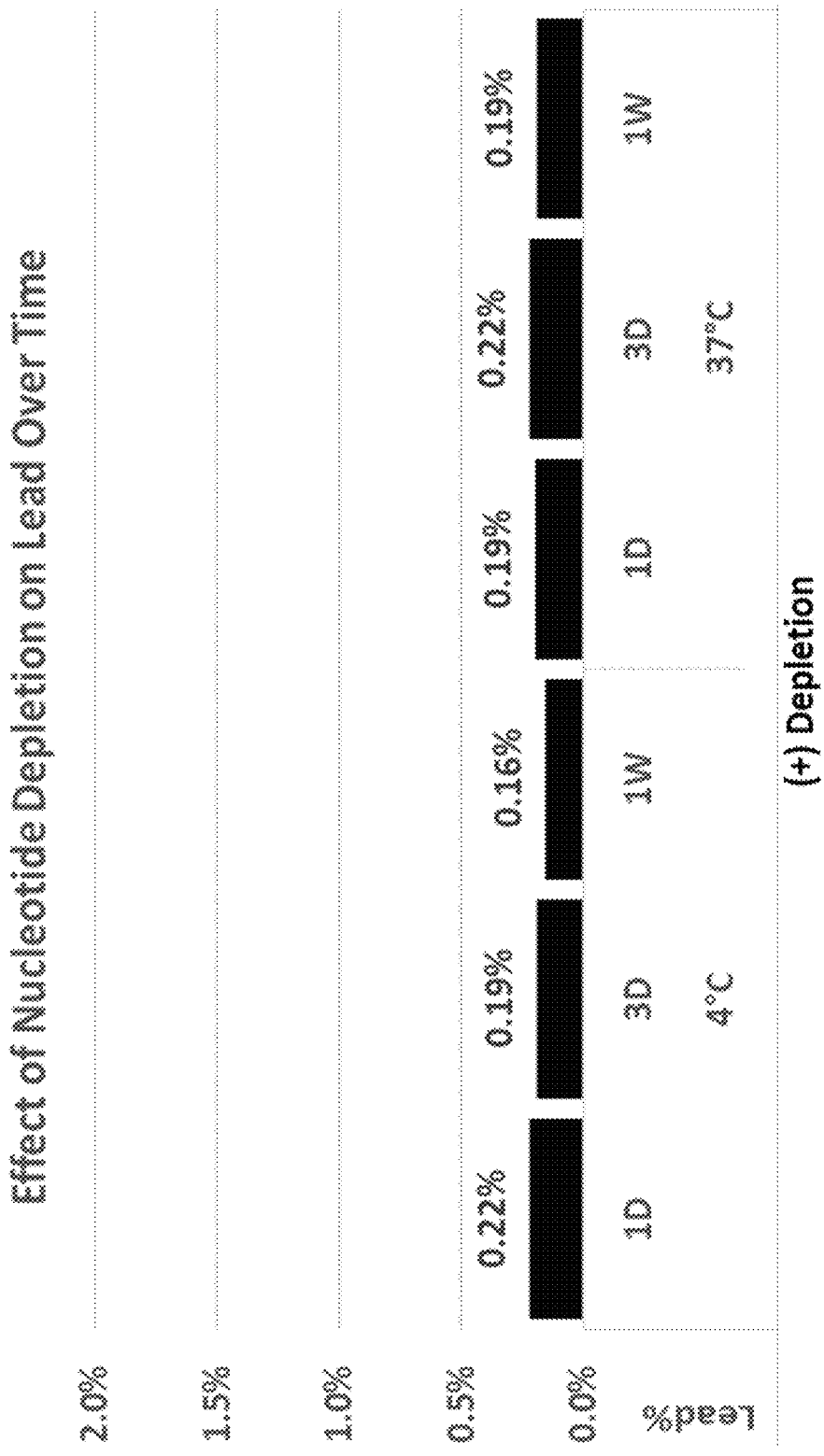

METHODS AND COMPOSITIONS FOR REDUCING NUCLEOTIDE IMPURITIES

CROSS-REFERENCES TO RELATED APPLICATIONS

This application is a continuation of International Patent Application No. PCT/US2021/057600, filed Nov. 1, 2021, and which claims the benefit of U.S. Provisional Application No. 63/108,179, filed Oct. 30, 2020, which is incorporated herein by reference in its entirety and for all purposes.

SEQUENCE LISTING

The instant application contains a Sequence Listing which has been submitted electronically in ASCII format and is hereby incorporated by reference in its entirety. Said ASCII copy, created on Mar. 10, 2023, is named 051385-539C01US_ST26.xml and is 8,499 bytes in size.

BACKGROUND

Modified nucleotides used in next generation sequencing (NGS) technologies, such as modified nucleotides containing reversible terminators, often contain impurities, such as natural nucleotides or non-reversible terminator-containing nucleotides. DNA polymerases generally discriminate against modified nucleotides in favor of 3'-OH bearing nucleotide counterparts when presented as a mixture. This typically leads to the clusters of monoclonal amplicons being out-of-phase, reducing sequencing accuracy and limiting sequencing read lengths.

BRIEF SUMMARY

In view of the foregoing, there is a need for an effective solution to the synchrony problems in ensemble-based sequencing methods, particularly for long read lengths. Disclosed herein, inter alia, are solutions to these and other problems in the art.

In an aspect is provided a composition including (a) nucleotides including a free 3'-OH, (b) nucleotides lacking a free 3'-OH, and (c) one or more reagents for decreasing the amount of the nucleotides including a free 3'-OH. In embodiments, the one or more reagents include a depletion primer, a depletion template, and a depletion polymerase that is active to extend the depletion primer along the depletion template by selectively incorporating the nucleotides including a free 3'-OH, wherein the depletion primer and the depletion template are free in solution. In embodiments, the one or more reagents include one or more nucleotide cyclases active to selectively cyclize the nucleotides including a free 3'-OH.

In an aspect is provided a method of sequencing a target polynucleotide. In embodiments, the method includes (a) incubating the target polynucleotide in a composition described herein (e.g., a reaction mixture including a sequencing primer, nucleotides including a free 3'-OH, nucleotides lacking a free 3'-OH, and a sequencing polymerase); (b) enzymatically decreasing the amount of the nucleotides including a free 3'-OH; (c) extending the sequencing primer along the target polynucleotide using the sequencing polymerase by incorporating one of the nucleotides lacking a free 3'-OH; and (d) identifying the incorporated nucleotide. In embodiments, steps (a)-(d) are performed in a sequencing flow cell. In embodiments, the target polynucleotide is immobilized to a solid substrate.

In an aspect is provided a method of decreasing the amount of 3'-OH nucleotide in a sequencing solution, said method including: (a) contacting a sequencing solution with a depleting solution, wherein said sequencing solution includes a 3'-OH nucleotide and a plurality of labeled 3-O-blocked reversible terminator nucleotides and wherein the depleting solution includes: (i) a depletion polynucleotide and a depletion polymerase, wherein the depletion polymerase incorporates the 3'-OH nucleotide into the depletion polynucleotide thereby producing an extended depletion polynucleotide; or (ii) a nucleotide cyclase, wherein the nucleotide cyclase cyclizes the 3'-OH nucleotide thereby producing a cyclized nucleotide; and (b) inactivating the depletion polymerase or the nucleotide cyclase.

In an aspect is provided a method of increasing storage stability of modified nucleotides. In embodiments, the modified nucleotides are for use in a sequencing reaction. In embodiments, the method of increasing the storage stability includes (a) storing the modified nucleotides in solution at about 2° C.-65° C. for at least 12 hours, wherein the modified nucleotides include nucleotides lacking a free 3'-OH, and wherein the solution includes nucleotides including a free 3'-OH; and (b) depleting the nucleotides including a free 3'-OH during storage. In embodiments, depleting the nucleotides including a free 3'-OH during storage includes extending a depletion primer along a depletion template using a depletion polymerase that selectively incorporates the nucleotides including a free 3'-OH, wherein the depletion primer and the depletion template are free in solution. In embodiments, depleting the nucleotides including a free 3'-OH during storage includes selectively cyclizing the nucleotides including the free 3'-OH using a nucleotide cyclase.

In an aspect is provided a method of sequencing a nucleic acid. The method includes (i) incorporating in series with a nucleic acid polymerase, within a reaction vessel, one of four different nucleotides from a composition (e.g., a nucleotide solution) described herein into a primer to create an extension strand, wherein said primer is hybridized to the nucleic acid and wherein each of the four different nucleotides comprises a detectable moiety; and (ii) detecting the detectable moiety of each incorporated nucleotide, so as to thereby identify each incorporated nucleotide in said extension strand, thereby sequencing the nucleic acid.

BRIEF DESCRIPTION OF THE DRAWINGS

FIGS. 4A-4B. Effects of nucleotide depletion (also referred to as live-polishing) on percent lead. FIG. 4A shows the results of reversibly-terminated nucleotides stored at either 4° C. or 37° C. for 1, 3, or 7 days (1 week) assayed for non-terminated nucleotide incorporation in the absence of a depletion solution (i.e., a non-live polished solution). Freshly manufactured, (F) nucleotides were included as a no-storage, non-depleted control. FIG. 4B shows the results of reversibly-terminated nucleotides stored at either 4° C. or 37° C. for 1, 3, or 7 days (1 week) assayed for non-terminated nucleotide incorporation in the presence of a depletion solution.

DETAILED DESCRIPTION

Figure 1:
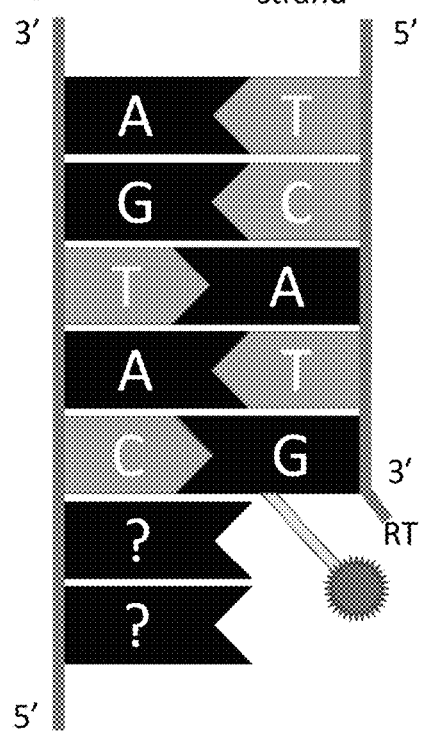
FIG. 1. A simplified depiction of a desired sequencing-by-synthesis (SBS) in-phase nucleotide incorporation and detection event. The complementary strand is extended by adding a modified G nucleotide, wherein the G nucleotide contains a 3' reversible terminator (RT) and a label (pictorially represented as a spiky ball). Note, the modified G nucleotide is incorporated via a polymerase, though the polymerase is not shown in the illustration. Following detection, the RT and linker are cleaved thereby removing the label and exposing a free 3' hydroxyl group.
Figure 1:
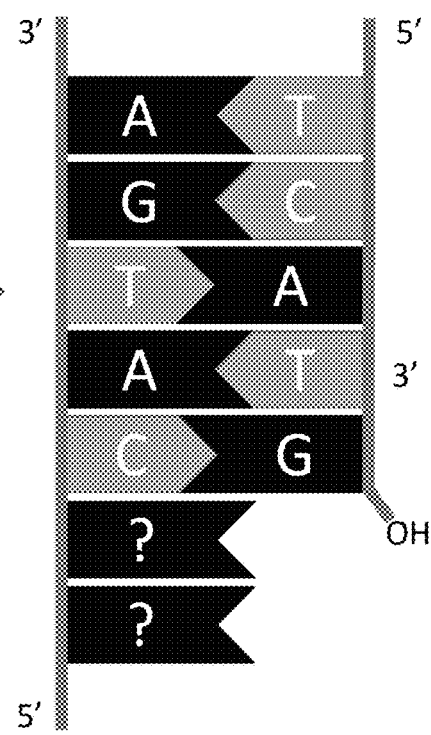

The aspects and embodiments described herein relate to depleting nucleotide impurities from nucleotide solutions. For example, described herein is a nucleotide solution. In embodiments, the nucleotide solution includes a plurality of modified nucleotides, depletion enzyme, buffer, and salt. In embodiments, the modified nucleotides include labeled reversibly-terminated nucleotides and labeled nucleotides. In embodiments, the solution includes a depletion oligonucleotide template and the depletion enzyme is a polymerase. In embodiments, the depletion enzyme is a cyclase. In embodiments, the nucleotide solution is maintained at a temperature of 4° C., 25° C., or 65° C. In embodiments, the depletion enzyme is active at low temperatures (e.g., 2° C.-10° C.). In embodiments, the depletion enzyme is not thermostable. In embodiments, the depletion enzyme is a zinc metalloenzyme. In embodiments, the depletion oligonucleotide templates are hairpins with a 5'-overhang with a poly(N) sequence, where N is T, G, C, or A. As described herein, the term "depletion oligonucleotide template" may be used interchangeably with "depletion template".

Described herein is a method of decreasing the amount of non-terminated modified nucleotides from a stored nucleotide solution. A stored nucleotide solution is a nucleotide solution that has been stored for a period of time (e.g., at least one day) following nucleotide manufacturing. In a stored nucleotide solution, the percentage of non-terminated nucleotides may increase relative to a freshly manufactured and purified nucleotide solution. In embodiments, the stored nucleotide solution is maintained at 2-8° C. or 20-30° C. In embodiments, the method includes mixing a stored nucleotide solution containing non-terminated and reversibly-terminated nucleotides with a depletion enzyme, wherein the depletion enzyme catalyzes a reaction with the non-terminated modified nucleotides to decrease the amount of non-terminated nucleotides from the stored nucleotide solution.

Also described herein is a method of decreasing the amount of non-terminated modified nucleotides from a sequencing solution within a microfluidic device. In embodiments, the method includes mixing a sequencing solution containing non-terminated and reversibly-terminated nucleotides with a depletion enzyme, wherein the depletion enzyme catalyzes a reaction with the non-terminated modified nucleotides to decrease the amount of non-terminated nucleotides from the sequencing solution; and flowing the sequencing solution into a reaction vessel within the microfluidic device.

I. Definitions

The practice of the technology described herein will employ, unless indicated specifically to the contrary, conventional methods of chemistry, biochemistry, organic chemistry, molecular biology, microbiology, recombinant DNA techniques, genetics, immunology, and cell biology that are within the skill of the art, many of which are described below for the purpose of illustration. Examples of such techniques are available in the literature. Methods, devices and materials similar or equivalent to those described herein can be used in the practice of this invention.

All patents, patent applications, articles and publications mentioned herein, both supra and infra, are hereby expressly incorporated herein by reference in their entireties.

Unless defined otherwise herein, all technical and scientific terms used herein have the same meaning as commonly understood by one of ordinary skill in the art to which this disclosure belongs. Various scientific dictionaries that include the terms included herein are well known and available to those in the art. Although any methods and materials similar or equivalent to those described herein find use in the practice or testing of the disclosure, some preferred methods and materials are described. Accordingly, the terms defined immediately below are more fully described by reference to the specification as a whole. It is to be understood that this disclosure is not limited to the particular methodology, protocols, and reagents described, as these may vary, depending upon the context in which they are used by those of skill in the art. The following definitions are provided to facilitate understanding of certain terms used frequently herein and are not meant to limit the scope of the present disclosure.

As used herein, the singular terms "a", "an", and "the" include the plural reference unless the context clearly indicates otherwise. Reference throughout this specification to, for example, "one embodiment", "an embodiment", "another embodiment", "a particular embodiment", "a related embodiment", "a certain embodiment", "an additional embodiment", or "a further embodiment" or combinations thereof means that a particular feature, structure or characteristic described in connection with the embodiment is included in at least one embodiment of the present disclosure. Thus, the appearances of the foregoing phrases in various places throughout this specification are not necessarily all referring to the same embodiment. Furthermore, the particular features, structures, or characteristics may be combined in any suitable manner in one or more embodiments.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

As used herein, the term "control" or "control experiment" is used in accordance with its plain and ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. For example the methods described herein measure an increase or decrease of a property relative to a control and it is understood that one having skill in the art would conduct a parallel experiment while omitting one or more steps of the method (e.g., omitting contact with one or more depleting reagents).

As used herein, the term "complement" is used in accordance with its plain and ordinary meaning and refers to a nucleotide (e.g., RNA nucleotide or DNA nucleotide) or a sequence of nucleotides capable of base pairing with another nucleotide or sequence of nucleotides (e.g., Watson-Crick base pairing). As described herein and commonly known in the art the complementary (matching) nucleotide of adenosine is thymidine in DNA, or alternatively in RNA the complementary (matching) nucleotide of adenosine is uracil, and the complementary (matching) nucleotide of guanosine is cytosine. Thus, a complement may include a sequence of nucleotides that base pair with corresponding complementary nucleotides of a second nucleic acid sequence. The nucleotides of a complement may partially or completely match the nucleotides of the second nucleic acid sequence. Where the nucleotides of the complement completely match each nucleotide of the second nucleic acid sequence, the complement forms base pairs with each nucleotide of the second nucleic acid sequence. Where the nucleotides of the complement partially match the nucleotides of the second nucleic acid sequence only some of the nucleotides of the complement form base pairs with nucleotides of the second nucleic acid sequence. Examples of complementary sequences include coding and non-coding sequences, wherein the non-coding sequence contains complementary nucleotides to the coding sequence and thus forms the complement of the coding sequence. A further example of complementary sequences are sense and antisense sequences, wherein the sense sequence contains complementary nucleotides to the antisense sequence and thus forms the complement of the antisense sequence.

As described herein, the complementarity of sequences may be partial, in which only some of the nucleic acids match according to base pairing, or complete, where all the nucleic acids match according to base pairing. Thus, two sequences that are complementary to each other, may have a specified percentage of nucleotides that complement one another (e.g., about 60%, preferably 65%, 70%, 75%, 80%, 85%, 90%, 91%, 92%, 93%, 94%, 95%, 96%, 97%, 98%, 99%, or higher complementarity over a specified region). In embodiments, two sequences are complementary when they are completely complementary, having 100% complementarity. In embodiments, sequences in a pair of complementary sequences form portions of a single polynucleotide with non-base-pairing nucleotides (e.g., as in a hairpin structure, with or without an overhang) or portions of separate polynucleotides. In embodiments, one or both sequences in a pair of complementary sequences form portions of longer polynucleotides, which may or may not include additional regions of complementarity.

As used herein, the term "contacting" is used in accordance with its plain ordinary meaning and refers to the process of allowing at least two distinct species (e.g. chemical compounds including biomolecules or cells) to become sufficiently proximal to react, interact or physically touch. However, the resulting reaction product can be produced directly from a reaction between the added reagents or from an intermediate from one or more of the added reagents that can be produced in the reaction mixture. The term "contacting" may include allowing two species to react, interact, or physically touch, wherein the two species may be a compound, nucleic acid, a protein, or enzyme (e.g., a DNA polymerase).

As used herein, the term "nucleic acid" is used in accordance with its plain and ordinary meaning and refers to nucleotides (e.g., deoxyribonucleotides or ribonucleotides) and polymers thereof in either single-, double- or multiple-stranded form, or complements thereof. The terms "polynucleotide," "oligonucleotide," "oligo" or the like refer, in the usual and customary sense, to a sequence of nucleotides. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA with linear or circular framework. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the disclosure may comprise natural nucleic acid sequences and variants thereof, artificial nucleic acid sequences, or a combination of such sequences. A "nucleoside" is structurally similar to a nucleotide, but is missing the phosphate moieties. An example of a nucleoside analogue would be one in which the label is linked to the base and there is no phosphate group attached to the sugar molecule.

As used herein, the term "modified nucleotide" refers to nucleotide modified in some manner. Typically, a nucleotide contains a single 5-carbon sugar moiety, a single nitrogenous base moiety and 1 to three phosphate moieties. In embodiments, a nucleotide can include a blocking moiety or a label moiety. A blocking moiety on a nucleotide prevents formation of a covalent bond between the 3' hydroxyl moiety of the nucleotide and the 5' phosphate of another nucleotide. A blocking moiety on a nucleotide can be reversible, whereby the blocking moiety can be removed or modified to allow the 3' hydroxyl to form a covalent bond with the 5' phosphate of another nucleotide. A blocking moiety can be effectively irreversible under particular conditions used in a method set forth herein. A label moiety of a nucleotide can be any moiety that allows the nucleotide to be detected, for example, using a spectroscopic method. Exemplary label moieties are fluorescent labels, mass labels, chemiluminescent labels, electrochemical labels, detectable labels and the like. One or more of the above moieties can be absent from a nucleotide used in the methods and compositions set forth herein. For example, a nucleotide can lack a label moiety or a blocking moiety or both. Examples of nucleotide analogues include, without limitation, 7-deaza-adenine, 7-deaza-guanine, the analogues of deoxynucleotides shown herein, analogues in which a label is attached through a cleavable linker to the 5-position of cytosine or thymine or to the 7-position of deaza-adenine or deaza-guanine, and analogues in which a small chemical moiety is used to cap the —OH group at the 3'-position of deoxyribose. Nucleotide analogues and DNA polymerase-based DNA sequencing are also described in U.S. Pat. No. 6,664,079, which is incorporated herein by reference in its entirety for all purposes The term "primer," as used herein, refers to an oligonucleotide, either natural or synthetic, which is capable, upon forming a duplex with a polynucleotide (e.g., the target polynucleotide or the depletion template), of acting as a point of initiation of nucleic acid synthesis and being extended from one of its ends along the template so that an extended polynucleotide duplex is formed. The sequence of nucleotides added during the extension process is determined by the sequence of the polynucleotide. Primers usually are extended by a DNA polymerase. A primer can be of any length depending on the particular technique it will be used for. For example, PCR primers are generally between 10 and 40 nucleotides in length. The length and complexity of the nucleic acid fixed onto the nucleic acid template is not critical to the invention. One of skill can adjust these factors to provide optimum hybridization and signal production for a given hybridization procedure, and to provide the required resolution among different genes or genomic locations. The primer permits the addition of a nucleotide residue thereto, or oligonucleotide or polynucleotide synthesis therefrom, under suitable conditions known in the art. In an embodiment the primer is a DNA primer, i.e., a primer consisting of, or largely consisting of, deoxyribonucleotide residues. The primers are designed to have a sequence that is the complement of a region of DNA (e.g., the depletion template or the target polynucleotide) to which the primer hybridizes. The addition of a nucleotide residue to the 3' end of a primer by formation of a phosphodiester bond results in a DNA extension product. The addition of a nucleotide residue to the 3' end of the DNA extension product by formation of a phosphodiester bond results in a further DNA extension product. In another embodiment the primer is an RNA primer.

Nucleic acids, including e.g., nucleic acids with a phosphothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent, or other interaction.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

As used herein, the terms "analogue" and "analog", in reference to a chemical compound, refers to compound having a structure similar to that of another one, but differing from it in respect of one or more different atoms, functional groups, or substructures that are replaced with one or more other atoms, functional groups, or substructures. In the context of a nucleotide, a "nucleotide analog" and "modified nucleotide" refer to a compound that, like the nucleotide of which it is an analog, can be incorporated into a nucleic acid molecule (e.g., an extension product) by a suitable polymerase, for example, a DNA polymerase in the context of a nucleotide analogue. The terms also encompass nucleic acids containing known nucleotide analogs or modified backbone residues or linkages, which are synthetic, naturally occurring, or non-naturally occurring, which have similar binding properties as the reference nucleic acid, and which are metabolized in a manner similar to the reference nucleotides. Examples of such analogs include, include, without limitation, phosphodiester derivatives including, e.g., phosphoramidate, phosphorodiamidate, phosphorothioate (also known as phosphothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see, e.g., see Eckstein, OLIGONUCLEOTIDES AND ANALOGUES: A PRACTICAL APPROACH, Oxford University Press) as well as modifications to the nucleotide bases such as in 5-methyl cytidine or pseudouridine.; and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA)), including those described in U.S. Pat. Nos. 5,235, 033 and 5,034,506, and Chapters 6 and 7, ASC Symposium Series 580, CARBOHYDRATE MODIFICATIONS IN ANTISENSE RESEARCH, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

As used herein, a "native" nucleotide is used in accordance with its plain and ordinary meaning and refers to a naturally occurring nucleotide that does not include an exogenous label (e.g., a fluorescent dye, or other label) or chemical modification such as those that may characterize a nucleotide analog (e.g., an analog having a reversible terminating moiety).

In embodiments, the nucleotides of the present disclosure use a cleavable linker to attach the label to the nucleotide. The use of a cleavable linker ensures that the label can, if required, be removed after detection, avoiding any interfering signal with any labelled nucleotide incorporated subsequently. The use of the term "cleavable linker" is not meant to imply that the whole linker is required to be removed from the nucleotide base. The cleavage site can be located at a position on the linker that ensures that part of the linker remains attached to the nucleotide base after cleavage. The linker can be attached at any position on the nucleotide base provided that Watson-Crick base pairing can still be carried out. In the context of purine bases, it is preferred if the linker is attached via the 7-position of the purine or the preferred deazapurine analogue, via an 8-modified purine, via an N-6 modified adenosine or an N-2 modified guanine. For pyrimidines, attachment is preferably via the 5-position on cytidine, thymidine or uracil and the N-4 position on cytosine. The term "cleavable linker" or "cleavable moiety" as used herein refers to a divalent or monovalent, respectively, moiety which is capable of being separated (e.g., detached, split, disconnected, hydrolyzed, a stable bond within the moiety is broken) into distinct entities. A cleavable linker is cleavable (e.g., specifically cleavable) in response to external stimuli (e.g., enzymes, nucleophilic/basic reagents, reducing agents, photo-irradiation, electrophilic/acidic reagents, organometallic and metal reagents, or oxidizing reagents). A chemically cleavable linker refers to a linker which is capable of being split in response to the presence of a chemical (e.g., acid, base, oxidizing agent, reducing agent, Pd(0), tris-(2-carboxyethyl)phosphine, dilute nitrous acid, fluoride, tris(3-hydroxypropyl)phosphine), sodium dithionite ($Na_2S_2O_4$), or hydrazine ($N_2H_4$)). A chemically cleavable linker is non-enzymatically cleavable. In embodiments, the cleavable linker is cleaved by contacting the cleavable linker with a cleaving agent. In embodiments, the cleaving agent is a phosphine containing reagent (e.g., TCEP or TIPP), sodium dithionite ($Na_2S_2O_4$), weak acid, hydrazine ($N_2H_4$), Pd(0), or light-irradiation (e.g., ultraviolet radiation).

As used herein, the terms "blocking moiety," "reversible blocking group," "reversible terminator" and "reversible terminator moiety" are used in accordance with their plain and ordinary meanings and refer to a cleavable moiety which does not interfere with incorporation of a nucleotide comprising it by a polymerase (e.g., DNA polymerase, modified DNA polymerase), but prevents further strand extension until removed ("unblocked"). For example, a reversible terminator may refer to a blocking moiety located, for example, at the 3' position of the nucleotide and may be a chemically cleavable moiety such as an allyl group, an azidomethyl group or a methoxymethyl group, or may be an enzymatically cleavable group such as a phosphate ester. Suitable nucleotide blocking moieties are described in applications WO 2004/018497, U.S. Pat. Nos. 7,057,026, 7,541, 444, WO 96/07669, U.S. Pat. Nos. 5,763,594, 5,808,045, 5,872,244 and 6,232,465 the contents of which are incorporated herein by reference in their entirety. The nucleotides may be labelled or unlabelled. The nucleotides may be modified with reversible terminators useful in methods provided herein and may be 3'-O-blocked reversible or 3'-unblocked reversible terminators. In nucleotides with 3'-O-blocked reversible terminators, the blocking group may be represented as —OR [reversible terminating (capping) group], wherein O is the oxygen atom of the 3'-OH of the pentose and R is the blocking group, while the label is linked to the base, which acts as a reporter and can be cleaved. The 3'-O-blocked reversible terminators are known in the art, and may be, for instance, a 3'-$ONH_2$ reversible terminator, a 3'-O-allyl reversible terminator, or a 3'-O-azidomethyl reversible terminator. In embodiments, the reversible terminator moiety is

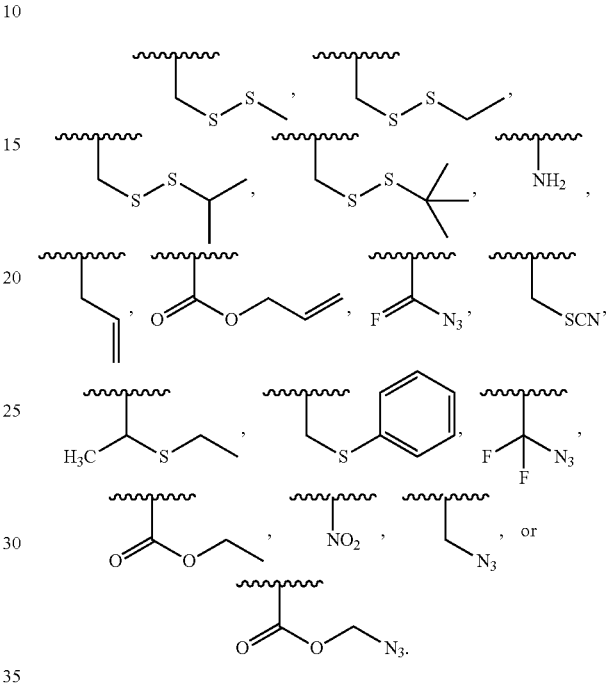

In embodiments, the reversible terminator moiety is

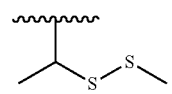 [SMILES: *C(C)SSC]

as described in U.S. Pat. No. 10,738,072, which is incorporated herein by reference for all purposes.

As used herein, the term "label" or "labels" is used in accordance with their plain and ordinary meanings and refer to molecules that can directly or indirectly produce or result in a detectable signal either by themselves or upon interaction with another molecule. Non-limiting examples of detectable labels include fluorescent dyes, biotin, digoxin, haptens, and epitopes. In general, a dye is a molecule, compound, or substance that can provide an optically detectable signal, such as a colorimetric, luminescent, bioluminescent, chemiluminescent, phosphorescent, or fluorescent signal. In embodiments, the label is a dye. In embodiments, the dye is a fluorescent dye. Non-limiting examples of dyes, some of which are commercially available, include CF® dyes (Biotium, Inc.), Alexa Fluor® dyes (Thermo Fisher), DyLight® dyes (Thermo Fisher), Cy® dyes (GE Healthscience), IRDye® dyes (Li-Cor Biosciences, Inc.), and HiLyte™ dyes (Anaspec, Inc.). In embodiments, a particular nucleotide type is associated with a particular label, such that identifying the label identifies the nucleotide with which it is associated. In embodiments, the label is luciferin that reacts with luciferase to produce a detectable signal in response to one or more bases being incorporated into an elongated complementary strand, such as in pyrosequencing. In embodiment, a nucleotide comprises a label (such as a dye). In embodiments, the label is not associated with any particular nucleotide, but detection of the label identifies whether one or more nucleotides having a known identity were added during an extension step (such as in the case of pyrosequencing).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics, which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide" and "protein" are used interchangeably herein to refer to a polymer of amino acid residues, wherein the polymer may In embodiments be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

"Conservatively modified variants" applies to both amino acid and nucleic acid sequences. With respect to particular nucleic acid sequences, "conservatively modified variants" refers to those nucleic acids that encode identical or essentially identical amino acid sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein, which encodes a polypeptide, also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure.

The following groups each contain amino acids that are conservative substitutions for one another: 1) Non-polar—Alanine (A), Leucine (L), Isoleucine (I), Valine (V), Glycine (G), Methionine (M); 2) Aliphatic—Alanine (A), Leucine (L), Isoleucine (I), Valine (V); 3) Acidic—Aspartic acid (D), Glutamic acid (E); 4) Polar—Asparagine (N), Glutamine (Q); Serine (S), Threonine (T); 5) Basic—Arginine (R), Lysine (K); 7) Aromatic—Phenylalanine (F), Tyrosine (Y), Tryptophan (W), Histidine (H); 8) Other—Cystein (C) and Proline (P).

The term "amino acid side chain" refers to the functional substituent contained on amino acids. For example, an amino acid side chain may be the side chain of a naturally occurring amino acid. Naturally occurring amino acids are those encoded by the genetic code (e.g., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine), as well as those amino acids that are later modified, e.g., hydroxyproline, γ-carboxyglutamate, and O-phosphoserine. In embodiments, the amino acid side chain may be a non-natural amino acid side chain.

The term "non-natural amino acid side chain" refers to the functional substituent of compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium, allylalanine, 2-aminoisobutryric acid. Non-natural amino acids are non-proteinogenic amino acids that occur naturally or are chemically synthesized. Such analogs have modified R groups (e.g., norleucine) or modified peptide backbones, but retain the same basic chemical structure as a naturally occurring amino acid. Non-limiting examples include exo-cis-3-Aminobicyclo[2.2.1]hept-5-ene-2-carboxylic acid hydrochloride, cis-2-Aminocycloheptanecarboxylic acid hydrochloride,cis-6-Amino-3-cyclohexene-1-carboxylic acid hydrochloride, cis-2-Amino-2-methylcyclohexanecarboxylic acid hydrochloride, cis-2-Amino-2-methylcyclopentanecarboxylic acid hydrochloride,2-(Boc-aminomethyl)benzoic acid, 2-(Boc-amino)octanedioic acid, Boc-4,5-dehydro-Leu-OH (dicyclohexylammonium), Boc-4-(Fmoc-amino)-L-phenylalanine, Boc-β-Homopyr-OH, Boc-(2-indanyl)-Gly-OH, 4-Boc-β-morpholineacetic acid, 4-Boc-β-morpholineacetic acid, Boc-pentafluoro-D-phenylalanine, Boc-pentafluoro-L-phenylalanine, Boc-Phe(2-Br)—OH, Boc-Phe(4-Br)—OH, Boc-D-Phe(4-Br)—OH, Boc-D-Phe(3-Cl)—OH, Boc-Phe(4-NH2)-OH, Boc-Phe(3-NO2)-OH, Boc-Phe(3,5-F2)-OH, 2-(4-Boc-piperazino)-2-(3,4-dimethoxyphenyl)acetic acid purum, 2-(4-Boc-piperazino)-2-(2-fluorophenyl)acetic acid purum, 2-(4-Boc-piperazino)-2-(3-fluorophenyl)acetic acid purum, 2-(4-Boc-piperazino)-2-(4-fluorophenyl)acetic acid purum, 2-(4-Boc-piperazino)-2-(4-methoxyphenyl)acetic acid purum, 2-(4-Boc-piperazino)-2-phenylacetic acid purum, 2-(4-Boc-piperazino)-2-(3-pyridyl)acetic acid purum, 2-(4-Boc-piperazino)-2-[4-(trifluoromethyl)phenyl] acetic acid purum, Boc-β-(2-quinolyl)-Ala-OH, N-Boc-1,2,3,6-tetrahydro-2-pyridinecarboxylic acid, Boc-β-(4-thiazolyl)-Ala-OH, Boc-β-(2-thienyl)-D-Ala-OH, Fmoc-N-(4-Boc-aminobutyl)-Gly-OH, Fmoc-N-(2-Boc-aminoethyl)-Gly-OH, Fmoc-N-(2,4-dimethoxybenzyl)-Gly-OH, Fmoc-(2-indanyl)-Gly-OH, Fmoc-pentafluoro-L-phenylalanine, Fmoc-Pen(Trt)-OH, Fmoc-Phe(2-Br)—OH, Fmoc-Phe(4-Br)—OH, Fmoc-Phe(3,5-F2)-OH, Fmoc-β-(4-thiazolyl)-Ala-OH, Fmoc-β-(2-thienyl)-Ala-OH, 4-(Hydroxymethyl)-D-phenylalanine.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length. As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 10 to 700, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., *Current Protocols in Molecular Biology* (Ausubel et al., eds. 1995 supplement)).

The terms "position", "numbered with reference to" or "corresponding to," when used in the context of the numbering of a given amino acid or polynucleotide sequence, refer to the numbering of the residues of a specified reference sequence when the given amino acid or polynucleotide sequence is compared to the reference sequence. As used herein, the term "functionally equivalent to" in relation to an amino acid position refers to an amino acid residue in a protein that corresponds to a particular amino acid in a reference sequence. An amino acid "corresponds" to a given residue when it occupies the same essential structural position within the protein as the given residue. One skilled in the art will immediately recognize the identity and location of residues corresponding to a specific position in a protein (e.g., polymerase) in other proteins with different numbering systems. For example, by performing a simple sequence alignment with a protein (e.g., polymerase) the identity and location of residues corresponding to specific positions of said protein are identified in other protein sequences aligning to said protein. Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

"Polymerase," as used herein, refers to any natural or non-naturally occurring enzyme or other catalyst that is capable of catalyzing a polymerization reaction, such as the polymerization of nucleotide monomers to form a nucleic acid polymer. Exemplary types of polymerases that may be used in the compositions and methods of the present disclosure include the nucleic acid polymerases such as DNA polymerase, DNA- or RNA-dependent RNA polymerase, and reverse transcriptase. In some cases, the DNA polymerase is 9° N polymerase or a variant thereof, *E. Coli* DNA polymerase I, Bacteriophage T4 DNA polymerase, Sequenase™ (GE Healthcare), Taq DNA polymerase, DNA polymerase from *Bacillus stearothermophilus*, Bst 2.0 DNA polymerase, 9° N polymerase (exo-)A485L/Y409V, Phi29 DNA Polymerase (φ29 DNA Polymerase), T7 DNA polymerase, DNA polymerase II, DNA polymerase III holoenzyme, DNA polymerase IV, DNA polymerase V, VentR DNA polymerase, Therminator™ II DNA Polymerase, Therminator™ III DNA Polymerase, or or Therminator™ IX DNA Polymerase. In embodiments, the polymerase is a protein polymerase. Typically, a DNA polymerase adds nucleotides to the 3'-end of a DNA strand, one nucleotide at a time. In embodiments, the DNA polymerase is a Pol I DNA polymerase, Pol II DNA polymerase, Pol III DNA polymerase, Pol IV DNA polymerase, Pol V DNA polymerase, Pol β DNA polymerase, Pol μ DNA polymerase, Pol λ DNA polymerase, Pol σ DNA polymerase, Pol α DNA polymerase, Pol δ DNA polymerase, Pol ε DNA polymerase, Pol η DNA polymerase, Pol τ DNA polymerase, Pol κ DNA polymerase, Pol ζ DNA polymerase, Pol γ DNA polymerase, Pol θ DNA polymerase, Pol ν DNA polymerase, or a thermophilic nucleic acid polymerase (e.g. Therminator™ γ, 9° N polymerase (exo-), Therminator™ II, Therminator™ III, or Therminator™ IX). As used herein, the term "thermophilic nucleic acid polymerase" refers to a family of DNA polymerases (e.g., 9° N™) and mutants thereof derived from the DNA polymerase originally isolated from the hyperthermophilic archaea, *Thermococcus* sp. 9 degrees N-7, found in hydrothermal vents at that latitude (East Pacific Rise) (Southworth M W, et al. PNAS. 1996; 93(11): 5281-5285). A thermophilic nucleic acid polymerase is a member of the family B DNA polymerases. Site-directed mutagenesis of the 3'-5' exo motif I (Asp-Ile-Glu or DIE) to AIA, AIE, EIE, EID or DIA yielded polymerase with no detectable 3' exonuclease activity. Mutation to Asp-Ile-Asp (DID) resulted in reduction of 3'-5' exonuclease specific activity to <1% of wild type, while maintaining other properties of the polymerase including its high strand displacement activity. The sequence AIA (D141A, E143A) was chosen for reducing exonuclease. Subsequent mutagenesis of key amino acids results in an increased ability of the enzyme to incorporate dideoxynucleotides, ribonucleotides and acyclonucleotides (e.g., Therminator™ II enzyme from New England Biolabs with D141A/E143A/Y409V/A485L mutations); 3'-amino-dNTPs, 3'-azido-dNTPs and other 3'-modified nucleotides (e.g., NEB Therminator™ III DNA Polymerase with D141A/E143A/L408S/Y409A/P410V mutations, NEB Therminator™ IX DNA polymerase), or 7-phosphate labeled nucleotides (e.g., Therminator™ 7: D141A/E143A/W355A/L408W/R460A/Q461S/K464E/D480V/R484W/A485L). Typically, these enzymes do not have 5'-3' exonuclease activity. Additional information about thermophilic nucleic acid polymerases may be found in (Southworth M W, et al. *PNAS.* 1996; 93(11):5281-5285; Bergen K, et al. *ChemBioChem.* 2013; 14(9):1058-1062; Kumar S, et al. *Scientific Reports.* 2012; 2:684; Fuller C W, et al. 2016; 113(19):5233-5238; Guo J, et al. *Proceedings of the National Academy of Sciences of the United States of America.* 2008; 105(27):9145-9150), which are incorporated herein in their entirety for all purposes.

As used herein, the term "exonuclease activity" is used in accordance with its ordinary meaning in the art, and refers to the removal of a nucleotide from a nucleic acid by a DNA polymerase. For example, during polymerization, nucleotides are added to the 3' end of the primer strand. Occasionally a DNA polymerase incorporates an incorrect nucleotide to the 3'-OH terminus of the primer strand, wherein the incorrect nucleotide cannot form a hydrogen bond to the corresponding base in the template strand. Such a nucleotide, added in error, is removed from the primer as a result of the 3' to 5' exonuclease activity of the DNA polymerase. In embodiments, exonuclease activity may be referred to as "proofreading." When referring to 3'-5' exonuclease activity, it is understood that the DNA polymerase facilitates a hydrolyzing reaction that breaks phosphodiester bonds at either the 3' end of a polynucleotide chain to excise the nucleotide. In embodiments, 3'-5' exonuclease activity refers to the successive removal of nucleotides in single-stranded DNA in a 3'→5' direction, releasing deoxyribonucleoside 5'-monophosphates one after another. Methods for quantifying exonuclease activity are known in the art, see for example Southworth et al, PNAS Vol 93, 8281-8285 (1996).

As used herein, the term "incorporating" or "chemically incorporating," when used in reference to a primer and cognate nucleotide, refers to the process of joining the cognate nucleotide to the primer or extension product thereof by formation of a phosphodiester bond.

As used herein, the term "selective" or "selectivity" or the like of a compound refers to the compound's ability to discriminate between molecular targets. For example, in a pool of nucleotides in which some nucleotides have a free 3'-OH and other nucleotides do not, an enzyme that selectively acts upon the nucleotides having a free 3'-OH is less likely to act (or not capable of acting) upon the nucleotides lacking a free 3'-OH. As a result, following the action by the enzyme, the relative proportion of nucleotides having a free 3'-OH in the pool is decreased. In embodiments, the enzyme is a polymerase that selectively incorporates nucleotides having a free 3'-OH in a primer extension reaction. In embodiments, the enzyme is a nucleotide cyclase that selectively cyclizes the nucleotides having a free 3'-OH.

As used herein, the terms "specific", "specifically", "specificity", or the like of a compound refers to the compound's ability to cause a particular action, such as binding, to a particular molecular target with minimal or no action to other proteins in the cell.

As used herein, the terms "bind" and "bound" are used in accordance with their plain and ordinary meanings and refer to an association between atoms or molecules. The association can be direct or indirect. For example, bound atoms or molecules may be directly bound to one another, e.g., by a covalent bond or non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). As a further example, two molecules may be bound indirectly to one another by way of direct binding to one or more intermediate molecules, thereby forming a complex.

As used herein, the terms "sequencing", "sequence determination", "determining a nucleotide sequence", and the like include determination of partial as well as full sequence information, including the identification, ordering, or locations of the nucleotides that comprise the polynucleotide being sequenced, and inclusive of the physical processes for generating such sequence information. That is, the term includes sequence comparisons, fingerprinting, and like levels of information about a target polynucleotide, as well as the express identification and ordering of nucleotides in a target polynucleotide. The term also includes the determination of the identification, ordering, and locations of one, two, or three of the four types of nucleotides within a target polynucleotide. Sequencing methods, such as those outlined in U.S. Pat. No. 5,302,509 can be carried out using the nucleotides described herein. The sequencing methods are preferably carried out with the target polynucleotide arrayed on a solid substrate. Multiple target polynucleotides can be immobilized on the solid support through linker molecules, or can be attached to particles, e.g., microspheres, which can also be attached to a solid substrate. In embodiments, the solid substrate is in the form of a chip, a bead, a well, a capillary tube, a slide, a wafer, a filter, a fiber, a porous media, or a column. In embodiments, the solid substrate is gold, quartz, silica, plastic, glass, diamond, silver, metal, or polypropylene. In embodiments, the solid substrate is porous.

As used herein, the term "sequencing reaction mixture" or "sequencing solution" is used in accordance with its plain and ordinary meaning and refers to an aqueous mixture that contains the reagents necessary to allow a dNTP or dNTP analogue to add a nucleotide to a DNA strand by a DNA polymerase. In embodiments, the sequencing reaction mixture includes a buffer. In embodiments, the buffer includes an acetate buffer, 3-(N-morpholino)propanesulfonic acid (MOPS) buffer, N-(2-Acetamido)-2-aminoethanesulfonic acid (ACES) buffer, phosphate-buffered saline (PBS) buffer, 4-(2-hydroxyethyl)-1-piperazineethanesulfonic acid (HEPES) buffer, N-(1,1-Dimethyl-2-hydroxyethyl)-3-amino-2-hydroxypropanesulfonic acid (AMPSO) buffer, borate buffer (e.g., borate buffered saline, sodium borate buffer, boric acid buffer), 2-Amino-2-methyl-1,3-propanediol (AMPD) buffer, N-cyclohexyl-2-hydroxyl-3-aminopropanesulfonic acid (CAPSO) buffer, 2-Amino-2-methyl-1-propanol (AMP) buffer, 4-(Cyclohexylamino)-1-butanesulfonic acid (CABS) buffer, glycine-NaOH buffer, N-Cyclohexyl-2-aminoethanesulfonic acid (CHES) buffer, tris(hydroxymethyl)aminomethane (Tris) buffer, or a N-cyclohexyl-3-aminopropanesulfonic acid (CAPS) buffer. In embodiments, the buffer is a borate buffer. In embodiments, the buffer is a CHES buffer. In embodiments, the sequencing reaction mixture includes nucleotides, wherein the nucleotides include a reversible terminating moiety and a label covalently linked to the nucleotide via a cleavable linker. In embodiments, the sequencing reaction mixture includes a buffer, DNA polymerase, detergent (e.g., Triton™ X), a chelator (e.g., EDTA), and/or salts (e.g., ammonium sulfate, magnesium chloride, sodium chloride, or potassium chloride). In embodiments, the sequencing reaction mixture includes the reagents used in a sequencing-by-synthesis protocol.

As used herein, the term "sequencing cycle" is used in accordance with its plain and ordinary meaning and refers to incorporating one or more nucleotides (e.g., nucleotide analogues) to the 3' end of a polynucleotide with a polymerase, and detecting one or more labels that identify the one or more nucleotides incorporated. The sequencing may be accomplished by, for example, sequencing by synthesis, pyrosequencing, and the like. In embodiments, a sequencing cycle includes extending a complementary polynucleotide by incorporating a first nucleotide using a polymerase, wherein the polynucleotide is hybridized to a template nucleic acid, detecting the first nucleotide, and identifying the first nucleotide. In embodiments, to begin a sequencing cycle, one or more differently labeled nucleotides and a DNA polymerase can be introduced. Following nucleotide addition, signals produced (e.g., via excitation and emission of a detectable label) can be detected to determine the identity of the incorporated nucleotide (based on the labels on the nucleotides). Reagents can then be added to remove the 3' reversible terminator and to remove labels from each incorporated base. Reagents, enzymes and other substances can be removed between steps by washing. Cycles may include repeating these steps, and the sequence of each cluster is read over the multiple repetitions.

"Hybridize" shall mean the annealing of a nucleic acid sequence to another nucleic acid sequence (e.g., one single-stranded nucleic acid (such as a primer) to another nucleic acid) based on the well-understood principle of sequence complementarity. In an embodiment the other nucleic acid is a single-stranded nucleic acid. In some embodiments, one portion of a nucleic acid hybridizes to itself, such as in the formation of a hairpin structure. The propensity for hybridization between nucleic acids depends on the temperature and ionic strength of their milieu, the length of the nucleic acids and the degree of complementarity. The effect of these parameters on hybridization is described in, for example, Sambrook J., Fritsch E. F., Maniatis T., Molecular cloning: a laboratory manual, Cold Spring Harbor Laboratory Press, New York (1989). As used herein, hybridization of a primer, or of a DNA extension product, respectively, is extendable by creation of a phosphodiester bond with an available nucleotide or nucleotide analogue capable of forming a phosphodiester bond, therewith. For example, hybridization can be performed at a temperature ranging from 15° C. to 95° C. In some embodiments, the hybridization is performed at a temperature of about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., or about 95° C. In other embodiments, the stringency of the hybridization can be further altered by the addition or removal of components of the buffered solution.

As used herein, the term "extension" or "elongation" is used in accordance with their plain and ordinary meanings and refer to synthesis by a polymerase of a new polynucleotide strand complementary to a template strand by adding free nucleotides (e.g., dNTPs) from a reaction mixture that are complementary to the template in the 5'-to-3' direction. Extension includes condensing the 5'-phosphate group of the dNTPs with the 3'-hydroxy group at the end of the nascent (elongating) DNA strand.

The term "reaction vessel" is used in accordance with its ordinary meaning in chemistry or chemical engineering, and refers to a container having an inner volume in which a reaction takes place. In embodiments, the reaction vessel may be designed to provide suitable reaction conditions such as reaction volume, reaction temperature or pressure, and stirring or agitation, which may be adjusted to ensure that the reaction proceeds with a desired, sufficient or highest efficiency for producing a product from the chemical reaction. In embodiments, the reaction vessel is a container for liquid, gas or solid. In embodiments, the reaction vessel may include an inlet, an outlet, a reservoir and the like. In embodiments, the reaction vessel is connected to a pump (e.g., vacuum pump), a controller (e.g., CPU), or a monitoring device (e.g., UV detector or spectrophotometer).

As used herein, the term "sequencing read" is used in accordance with its plain and ordinary meaning and refers to an inferred sequence of base pairs (or base pair probabilities) corresponding to all or part of a single DNA fragment. Sequencing technologies vary in the length of reads produced. Reads of length 20-40 base pairs (bp) are referred to as ultra-short. Typical sequencers produce read lengths in the range of 100-500 bp. A sequencing read may include 10, 20, 30, 40, 50, 60, 70, 80, 90, 100, 150, 200, 250, or more nucleotide bases. Read length is a factor which can affect the results of biological studies. For example, longer read lengths improve the resolution of de novo genome assembly and detection of structural variants.

"Solid substrate" shall mean any suitable medium present in the solid phase to which a nucleic acid or an agent may be affixed. Non-limiting examples include chips, beads and columns. The solid substrate can be non-porous or porous. Exemplary solid substrates include, but are not limited to, glass and modified or functionalized glass, plastics (including acrylics, polystyrene and copolymers of styrene and other materials, polypropylene, polyethylene, polybutylene, polyurethanes, Teflon™, cyclic olefins, polyimides, etc.), nylon, ceramics, resins, Zeonor® (Zeon Corporation), silica or silica-based materials including silicon and modified silicon, carbon, metals, inorganic glasses, optical fiber bundles, and polymers. In embodiments, the solid substrate has at least one surface located within a flow cell. The solid substrate, or regions thereof, can be substantially flat. The solid substrate can have surface features such as wells, pits, channels, ridges, raised regions, pegs, posts or the like. The term solid substrate is encompassing of a substrate (e.g., a flow cell) having a surface comprising a polymer coating covalently attached thereto. In embodiments, the solid substrate is a flow cell. The term "flow cell" as used herein refers to a chamber including a solid surface across which one or more fluid reagents can be flowed. Examples of flow cells and related fluidic systems and detection platforms that can be readily used in the methods of the present disclosure are described, for example, in Bentley et al., Nature 456: 53-59 (2008). The term "flow cell" may refer to the reaction vessel in a microfluidic device (e.g., nucleic acid sequencing device). The flow cell is typically a glass slide containing small fluidic channels (e.g., a glass slide 75 mm×25 mm×1 mm having one or more channels), through which sequencing solutions (e.g., polymerases, nucleotides, and buffers) may traverse. Though typically glass, suitable flow cell materials may include polymeric materials, plastics, silicon, quartz (fused silica), Borofloat® glass, silica, silica-based materials, carbon, metals, an optical fiber or optical fiber bundles, sapphire, or plastic materials such as COCs and epoxies. The particular material can be selected based on properties desired for a particular use. The flow cells used in the various embodiments can include millions of individual nucleic acid clusters, e.g., about 2-8 million clusters per channel. Each of such clusters can give read lengths of at least 25-100 bases for DNA sequencing. The systems and methods herein can generate over a gigabase (one billion bases) of sequence per run.

Where a range of values is provided, it is understood that each intervening value, to the tenth of the unit of the lower limit unless the context clearly indicates otherwise, between the upper and lower limit of that range, and any other stated or unstated intervening value in, or smaller range of values within, that stated range is encompassed within the invention. The upper and lower limits of any such smaller range (within a more broadly recited range) may independently be included in the smaller ranges, or as particular values themselves, and are also encompassed within the invention, subject to any specifically excluded limit in the stated range. Where the stated range includes one or both of the limits, ranges excluding either or both of those included limits are also included in the invention.

The methods and kits of the present disclosure may be applied, mutatis mutandis, to the sequencing of RNA, or to determining the identity of a ribonucleotide.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., packaging, buffers, written instructions for performing a method, etc.) from one location to another. For example, kits include one or more enclosures (e.g., boxes) containing the relevant reaction reagents and/or supporting materials. As used herein, the term "fragmented kit" refers to a delivery system comprising two or more separate containers that each contain a subportion of the total kit components. The containers may be delivered to the intended recipient together or separately. For example, a first container may contain an enzyme for use in an assay, while a second container contains oligonucleotides. In contrast, a "combined kit" refers to a delivery system containing all of the components of a reaction assay in a single container (e.g., in a single box housing each of the desired components). The term "kit" includes both fragmented and combined kits.

As used herein, the terms "reduce," "decrease," "reduction," "minimal," "low," or "lower" refer to decreases below basal levels, e.g., as compared to a control. The terms "increase," "high," "higher," "maximal," "elevate," or "elevation" refer to increases above basal levels, e.g., as compared to a control. Increases, elevations, decreases, or reductions can be 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% compared to a control or standard level. Each of the values or ranges recited herein may include any value or subrange therebetween, including endpoints.

II. Compositions, Devices, & Kits

In an aspect is provided a composition including (a) nucleotides including a free 3'-OH, (b) nucleotides lacking a free 3'-OH, and (c) one or more reagents for decreasing the amount of the nucleotides including a free 3'-OH. In embodiments, the one or more reagents include a depletion primer, a depletion template, and a depletion polymerase that is active to extend the depletion primer along the depletion template by selectively incorporating the nucleotides including a free 3'-OH. In embodiments, the one or more reagents include a depletion primer and a depletion polymerase that is active to extend the depletion primer by selectively incorporating the nucleotides including a free 3'-OH. In embodiments, the depletion primer is annealed to a depletion template. In embodiments, the depletion primer and the depletion template are portions of a single polynucleotide (e.g., as described herein). In embodiments, the one or more reagents include a depletion primer, a depletion template, and a depletion polymerase that is active to extend the depletion primer along the depletion template by selectively incorporating the nucleotides including a free 3'-OH, wherein the depletion primer and the depletion template are free in solution. In embodiments, the one or more reagents include a depletion template and a depletion polymerase that is active to incorporate nucleotides including a free 3'-OH into the depletion template. In embodiments, the one or more reagents include one or more nucleotide cyclases active to selectively cyclize the nucleotides including a free 3'-OH.

In another aspect is provided a composition including: (a) labeled nucleotides including a free 3'-OH, (b) labeled nucleotides lacking a free 3'-OH, and (c) one or more depleting reagents for decreasing the amount of the nucleotides including a free 3'-OH, wherein the one or more depleting reagents include: (i) one or more depletion polynucleotides and a depletion polymerase that is active to selectively incorporating the nucleotides including a free 3'-OH, wherein the depletion polynucleotide is free in solution; or (ii) one or more nucleotide cyclases active to selectively cyclize the nucleotides including a free 3'-OH. In embodiments, the composition is stored in a single container. In embodiments, each nucleotide type (e.g., modified dATP, dTTP, dCTP, and dGTP) of composition is stored in a different container with one or more depleting reagents. In embodiments, the composition is stored at about 2° C.-8° C., about 20° C.-30° C., or about 4° C.-37° C. In embodiments, the composition is stored at about 4° C. to about 30° C.

In embodiments, the composition includes nucleotides lacking a free 3'-OH. In embodiments, the nucleotides lacking a free 3'-OH include a reversible terminator moiety. The reversible terminator moiety may be covalently linked to the 3'-oxygen position of the ribose sugar of a nucleotide. For example, a nucleotide lacking a free 3'-OH may be represented by the formula:

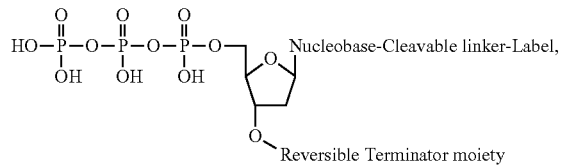

where the nucleobase is adenine or adenine analogue, thymine or thymine analogue, guanine or guanine analogue, or cytosine or cytosine analogue.

In embodiments, the nucleotide lacking a free 3'-OH has the formula:

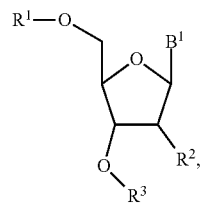

(I)

wherein $B^1$ is an optionally substituted nucleobase; $R^1$ is —OH, a monophosphate moiety, or polyphosphate moiety; $R^2$ is —OH or hydrogen; and $R^3$ is a reversible terminator moiety.

In embodiments, $B^1$ is

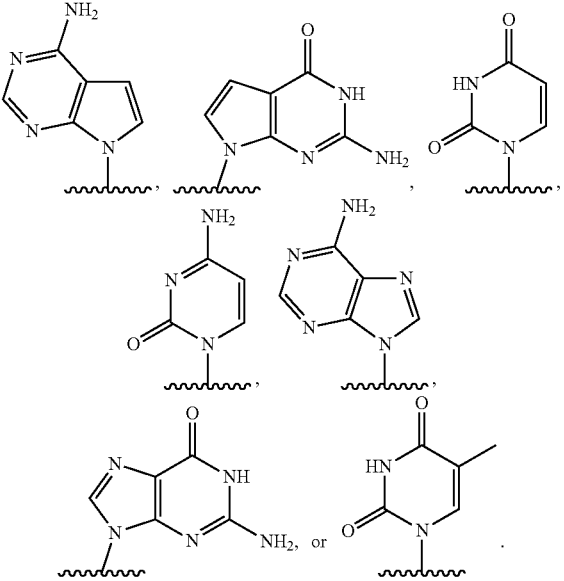

In embodiments, $B^1$ is a divalent nucleobase. In embodiments, $B^1$ is

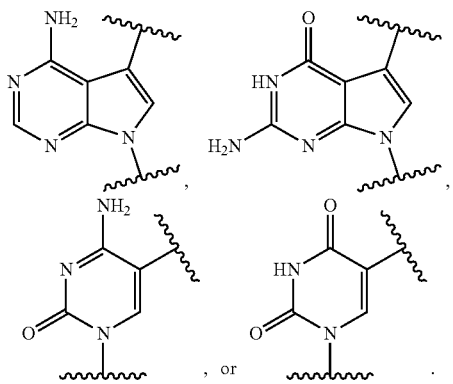

In embodiments, $B^1$ is

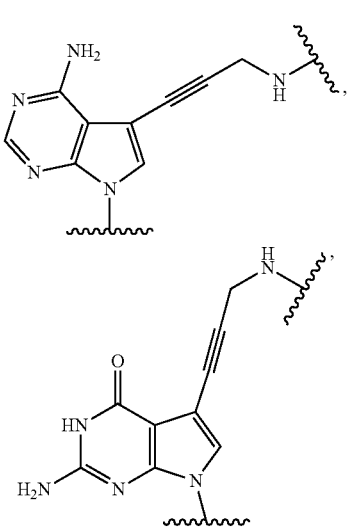

-continued

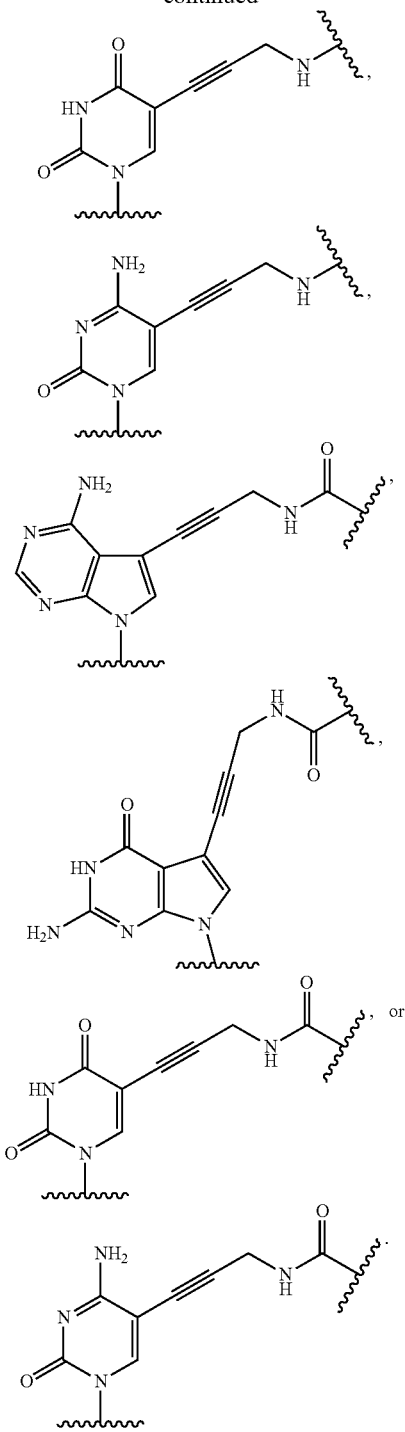

In embodiments, $B^1$ is —B-$L^{100}$-$R^4$. B is a divalent cytosine or a derivative thereof, divalent guanine or a derivative thereof, divalent adenine or a derivative thereof, divalent thymine or a derivative thereof, divalent uracil or a derivative thereof, divalent hypoxanthine or a derivative thereof, divalent xanthine or a derivative thereof, divalent 7-methylguanine or a derivative thereof, divalent 5,6-dihydrouracil or a derivative thereof, divalent 5-methylcytosine or a derivative thereof, or divalent 5-hydroxymethylcytosine or a derivative thereof. $L^{100}$ is a divalent linker; and $R^4$ is a detectable moiety. In embodiments, $L^{100}$ is independently a bioconjugate linker, a cleavable linker, or a self-immolative linker.

In embodiments, $R^4$ is a detectable moiety. In embodiments, $R^4$ is a fluorescent dye moiety. In embodiments, $R^4$ is a detectable moiety described herein (e.g., Table 1). In embodiments, $R^4$ is a detectable moiety described in Table 1. In embodiments, $R^4$ is a fluorescent dye moiety wherein the maximum emission of the fluorescent dye moiety is greater than about 530, 540, or 550 nm. In embodiments, $R^4$ is a fluorescent dye moiety wherein the maximum emission of the fluorescent dye moiety is greater than 530 nm. In embodiments, $R^4$ is a fluorescent dye moiety wherein the maximum emission of the fluorescent dye moiety is less than about 700, 690, or 680 nm. In embodiments, $R^4$ is a fluorescent dye moiety wherein the maximum emission of the fluorescent dye moiety is less than 680 nm. In embodiments, $R^4$ is a fluorescent dye moiety wherein the maximum emission of the fluorescent dye moiety is greater than about 530 and less than about 680 nm. In embodiments, $R^4$ is a fluorescent dye moiety wherein the maximum emission of the fluorescent dye moiety is greater than 530 and less than 680 nm. For example, $R^4$ may be any fluorescent moiety described in US Publication 2020/0216682, which is incorporated herein by reference. In embodiments, $R^4$ is

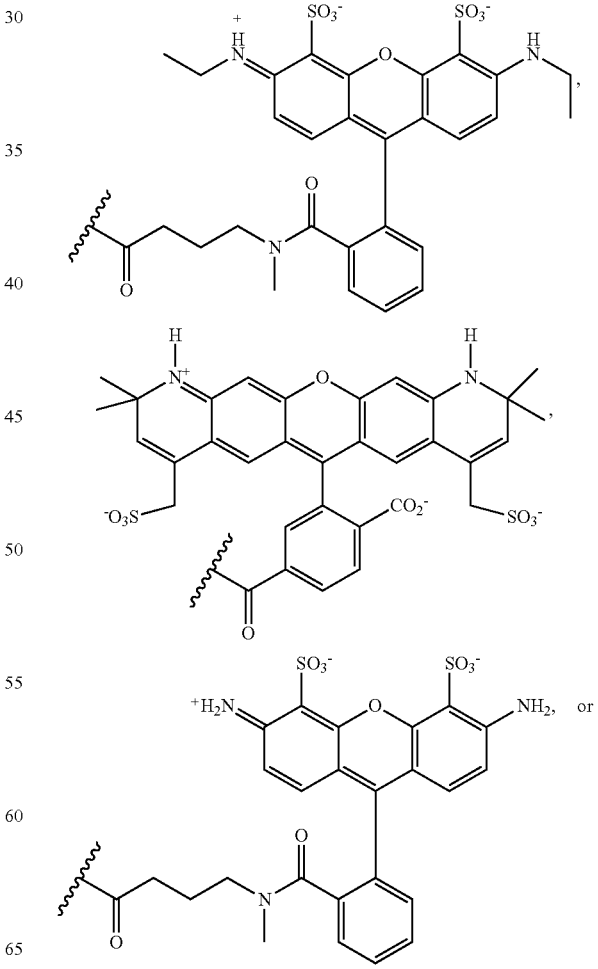

-continued

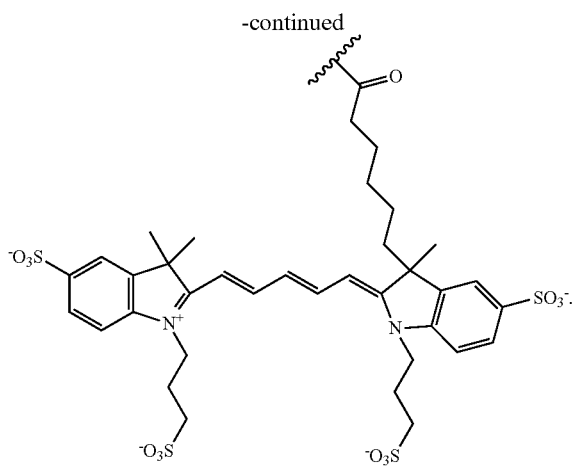

TABLE 1

Detectable moieties to be used in selected embodiments.

| Nucleoside/nucleotide abbreviation | Dye name | λmax (nm) |
| --- | --- | --- |
| dC | Atto 532 | 532 |
| dC | Atto Rho 6G | 535 |
| dC | R6G | 534 |
| dC | Tet | 521 |
| dT | Atto Rho 11 | 572 |
| dT | Atto 565 | 564 |
| dT | Alexa Fluor 568 | 578 |
| dT | dTamra | 578 |
| dA | Alexa Fluor 647 | 650 |
| dA | Atto 647N | 644 |
| dA | Janelia Fluor 646 | 646 |
| dG | Alexa Fluor 680 | 682 |
| dG | Alexa Fluor 700 | 696 |
| dG | CF680R | 680 |

In embodiments, the nucleotides including a free 3'-OH have the formula:

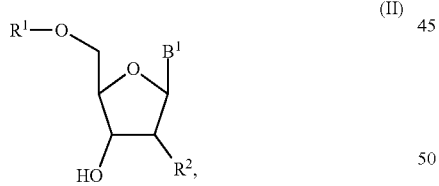

wherein $R^1$, $R^2$, and $B^1$ are as described herein, including embodiments.

In embodiments the reversible terminator moiety does not decrease the function of a polymerase relative to the absence of the reversible terminator moiety. In embodiments, the reversible terminator moiety does not negatively affect DNA polymerase recognition. In embodiments, the reversible terminator moiety does not negatively affect (e.g., limit) the read length of the DNA polymerase. Additional examples of a reversible terminator moiety may be found in U.S. Pat. No. 6,664,079, Ju J. et al. (2006) *Proc Natl Acad Sci USA* 103(52):19635-19640; Ruparel H. et al. (2005) *Proc Natl Acad Sci USA* 102(17):5932-5937; Wu J. et al. (2007) *Proc Natl Acad Sci USA* 104(104):16462-16467; Guo J. et al. (2008) *Proc Natl Acad Sci USA* 105(27): 9145-9150 Bentley D. R. et al. (2008) *Nature* 456(7218):53-59; or Hutter D. et al. (2010) *Nucleosides Nucleotides & Nucleic Acids* 29:879-895, which are incorporated herein by reference in their entirety for all purposes. In embodiments, a reversible terminator moiety includes an azido moiety or a dithiol linking moiety. In embodiments, the reversible terminator moiety is —NH$_2$, —CN, —CH$_3$, C$_2$-C$_6$ allyl (e.g., —CH$_2$—CH=CH$_2$), methoxyalkyl (e.g., —CH$_2$—O—CH$_3$), methoxyalkenyl (e.g., —CH$_2$—O—CH=CH$_2$), or —CH$_2$N$_3$. In embodiments, the reversible terminator moiety comprises a disulfide moiety. In embodiments, the reversible terminator is a moiety described in U.S. Pat. No. 10,738,072, which is incorporated herein by reference in its entirety.

In embodiments, the reversible terminator moiety (e.g., represented by the symbol $R^3$ in Formula (I)) is:

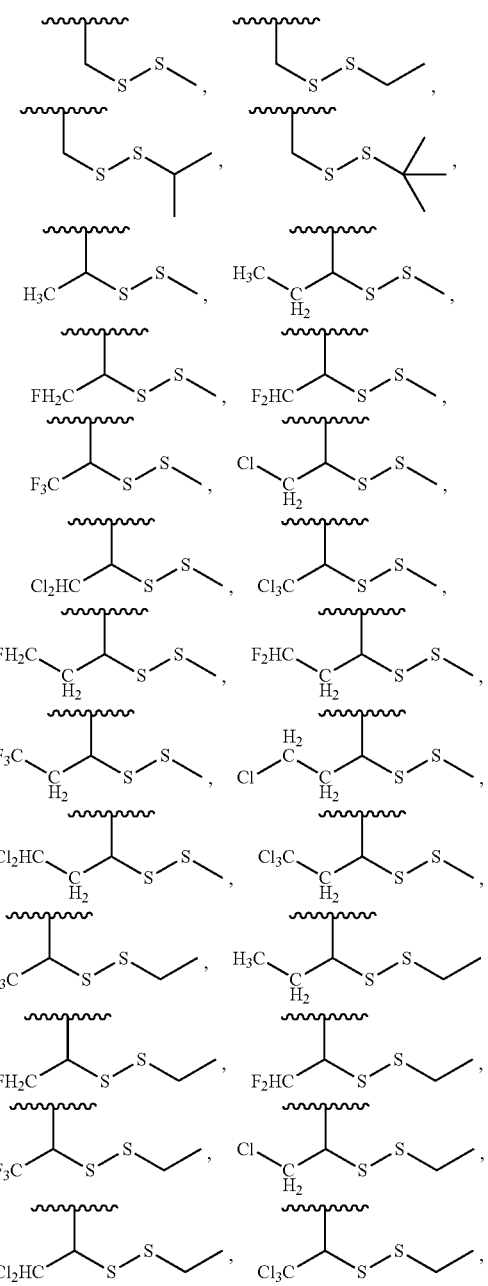

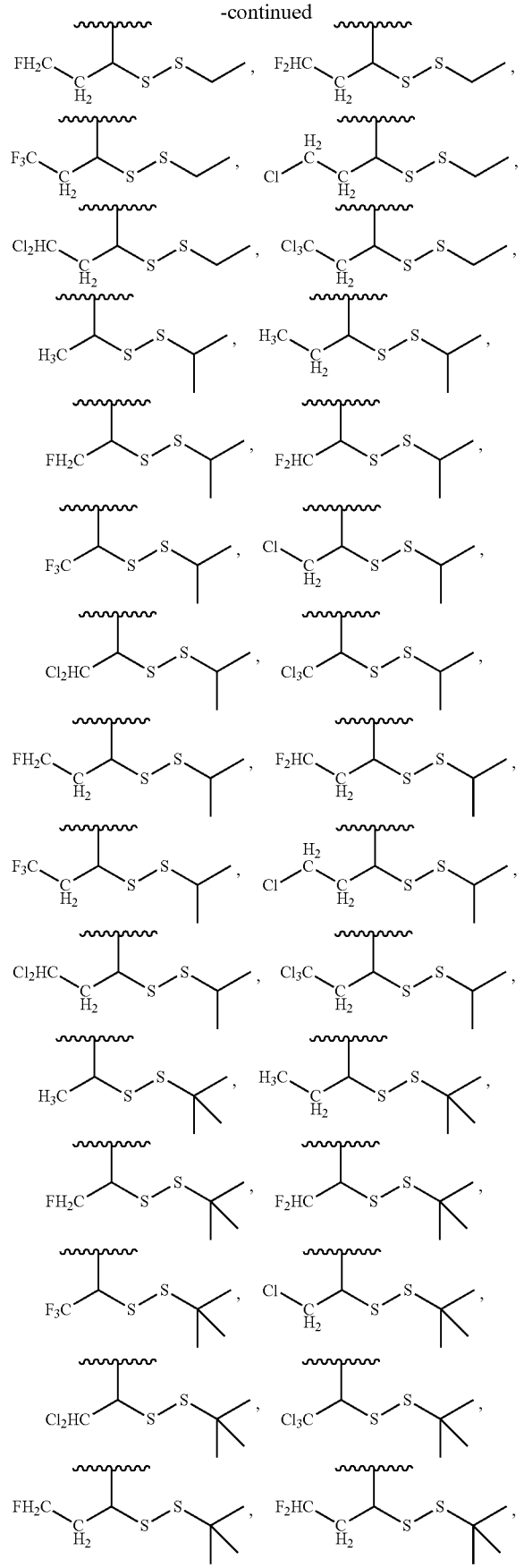
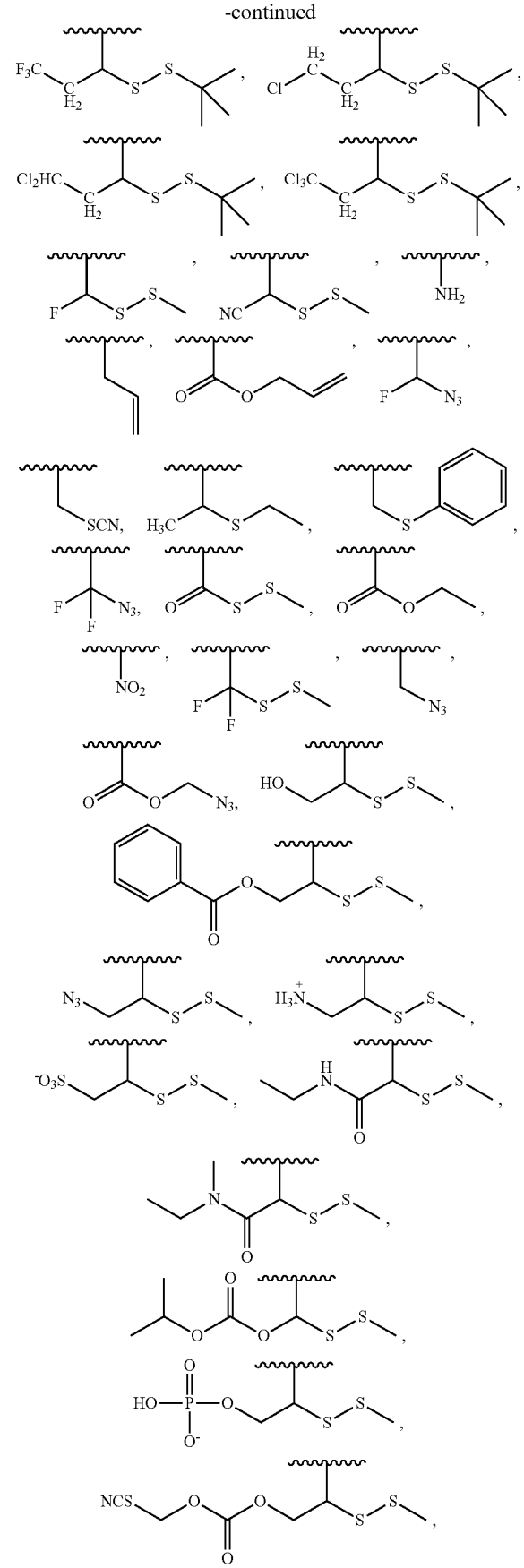

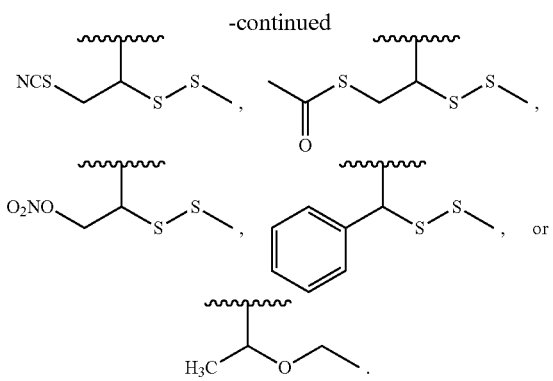

In embodiments, the labeled nucleotide lacking a free 3'-OH has the formula:

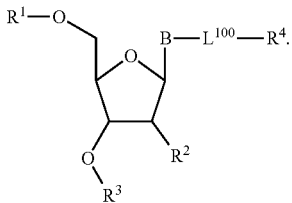

(I-A)

$R^1$ is a polyphosphate moiety, monophosphate moiety, or —OH. $R^2$ is hydrogen or —OH. $R^3$ is a reversible terminator moiety. $R^4$ is a detectable moiety. B is a divalent cytosine or a derivative thereof, divalent guanine or a derivative thereof, divalent adenine or a derivative thereof, divalent thymine or a derivative thereof, divalent uracil or a derivative thereof, divalent hypoxanthine or a derivative thereof, divalent xanthine or a derivative thereof, divalent 7-methylguanine or a derivative thereof, divalent 5,6-dihydrouracil or a derivative thereof, divalent 5-methylcytosine or a derivative thereof, or divalent 5-hydroxymethylcytosine or a derivative thereof. $L^{100}$ is a divalent linker.

In embodiments, the method includes the labeled nucleotide including a free 3'-OH has the formula:

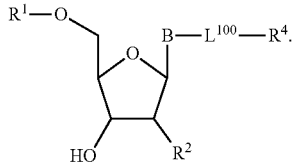

(II-A)

$R^1$ is a polyphosphate moiety, monophosphate moiety, or —OH. $R^2$ is hydrogen or —OH. $R^4$ is a detectable moiety. B is a divalent cytosine or a derivative thereof, divalent guanine or a derivative thereof, divalent adenine or a derivative thereof, divalent thymine or a derivative thereof, divalent uracil or a derivative thereof, divalent hypoxanthine or a derivative thereof, divalent xanthine or a derivative thereof, divalent 7-methylguanine or a derivative thereof, divalent 5,6-dihydrouracil or a derivative thereof, divalent 5-methylcytosine or a derivative thereof, or divalent 5-hydroxymethylcytosine or a derivative thereof. $L^{100}$ is a divalent linker.

In embodiments, $L^{100}$ is a cleavable linker. The term "cleavable linker" or "cleavable moiety" as used herein refers to a divalent or monovalent, respectively, moiety which is capable of being separated (e.g., detached, split, disconnected, hydrolyzed, a stable bond within the moiety is broken) into distinct entities. In embodiments, a cleavable linker is cleavable (e.g., specifically cleavable) in response to external stimuli (e.g., enzymes, nucleophilic/basic reagents, reducing agents, photo-irradiation, electrophilic/acidic reagents, organometallic and metal reagents, or oxidizing reagents). In embodiments, a cleavable linker is a self-immolative linker, a trivalent linker, or a linker capable of dendritic amplication of signal, or a self-immolative dendrimer containing linker (e.g., all as described in US 2007/0009980, US 2006/0003383, and US 2009/0047699, which are incorporated by reference in their entirety for any purpose). A chemically cleavable linker refers to a linker which is capable of being split in response to the presence of a chemical (e.g., acid, base, oxidizing agent, reducing agent, Pd(0), tris-(2-carboxyethyl)phosphine, dilute nitrous acid, fluoride, tris(3-hydroxypropyl)phosphine), sodium dithionite ($Na_2S_2O_4$), hydrazine ($N_2H_4$)). A chemically cleavable linker is non-enzymatically cleavable. In embodiments, the cleavable linker is cleaved by contacting the cleavable linker with a cleaving agent. In embodiments, the cleaving agent is sodium dithionite ($Na_2S_2O_4$), weak acid, hydrazine ($N_2H_4$), Pd(0), or light-irradiation (e.g., ultraviolet radiation). In embodiments, cleaving includes removing. In embodiments, $L^{100}$ includes a cleavable site. A "cleavable site" or "scissile linkage" in the context of a polynucleotide is a site which allows controlled cleavage of the polynucleotide strand (e.g., the linker, the primer, or the polynucleotide) by chemical, enzymatic, or photochemical means known in the art and described herein. A scissile site may refer to the linkage of a nucleotide between two other nucleotides in a nucleotide strand (i.e., an internucleosidic linkage). In embodiments, the scissile linkage can be located at any position within the one or more nucleic acid molecules, including at or near a terminal end (e.g., the 3' end of an oligonucleotide) or in an interior portion of the one or more nucleic acid molecules. In embodiments, conditions suitable for separating a scissile linkage include a modulating the pH and/or the temperature. In embodiments, a scissile site can include at least one acid-labile linkage. For example, an acid-labile linkage may include a phosphoramidate linkage. In embodiments, a phosphoramidate linkage can be hydrolysable under acidic conditions, including mild acidic conditions such as trifluoroacetic acid and a suitable temperature (e.g., 30° C.), or other conditions known in the art, for example Matthias Mag, et al Tetrahedron Letters, Volume 33, Issue 48, 1992, 7319-7322. In embodiments, the scissile site can include at least one photolabile internucleosidic linkage (e.g., o-nitrobenzyl linkages, as described in Walker et al, J. Am. Chem. Soc. 1988, 110, 21, 7170-7177), such as o-nitrobenzyloxymethyl or p-nitrobenzyloxymethyl group(s). In embodiments, the scissile site includes at least one uracil nucleobase. In embodiments, a uracil nucleobase can be cleaved with a uracil DNA glycosylase (UDG) or Formamidopyrimidine DNA Glycosylase Fpg. In embodiments, the scissile linkage site includes a sequence-specific nicking site having a nucleotide sequence that is recognized and nicked by a nicking endonuclease enzyme or a uracil DNA glycosylase. The term "self-immolative" referring to a linker is used in accordance with its well understood meaning in Chemistry and Biology as used in US 2007/0009980, US 2006/0003383, and US 2009/0047699, which are incorporated by reference in their entirety for any purpose. In embodiments "self-immolative" referring to a linker refers to a linker that is capable of additional cleavage following initial cleavage by an external stimuli. The term dendrimer is used in accordance with its well understood meaning in Chemistry. In embodiments, the term "self-immolative dendrimer" is used as described in US 2007/0009980, US 2006/0003383, and US 2009/0047699, which are incorporated by reference in their entirety for any purpose and in embodiments refers to a dendrimer that is capable of releasing all of its tail units through a self-immolative fragmentation following initial cleavage by an external stimulus. In embodiments, the cleavable linker is a linker described in U.S. Pat. No. 10,822,653 or U.S. Pat. No. 10,738,072, which is incorporated herein by reference in its entirety.

A "photocleavable linker" (e.g., including or consisting of an o-nitrobenzyl group) refers to a linker which is capable of being split in response to photo-irradiation (e.g., ultraviolet radiation). An acid-cleavable linker refers to a linker which is capable of being split in response to a change in the pH (e.g., increased acidity). A base-cleavable linker refers to a linker which is capable of being split in response to a change in the pH (e.g., decreased acidity). An oxidant-cleavable linker refers to a linker which is capable of being split in response to the presence of an oxidizing agent. A reductant-cleavable linker refers to a linker which is capable of being split in response to the presence of a reducing agent (e.g., tris(3-hydroxypropyl)phosphine). In embodiments, the cleavable linker is a dialkylketal linker (Binaulda S., et al., Chem. Commun., 2013, 49, 2082-2102; Shenoi R. A., et al., J. Am. Chem. Soc., 2012, 134, 14945-14957), an azo linker (Rathod, K. M., et al., Chem. Sci. Tran., 2013, 2, 25-28; Leriche G., et al., Eur. J. Org. Chem., 2010, 23, 4360-64), an allyl linker, a cyanoethyl linker, a 1-(4,4-dimethyl-2,6-dioxocyclohex-1-ylidene)ethyl linker, or a nitrobenzyl linker.

The term "orthogonally cleavable linker" or "orthogonal cleavable linker" as used herein refer to a cleavable linker that is cleaved by a first cleaving agent (e.g., enzyme, nucleophilic/basic reagent, reducing agent, photo-irradiation, electrophilic/acidic reagent, organometallic and metal reagent, oxidizing reagent) in a mixture of two or more different cleaving agents and is not cleaved by any other different cleaving agent in the mixture of two or more cleaving agents. For example, two different cleavable linkers are both orthogonal cleavable linkers when a mixture of the two different cleavable linkers are reacted with two different cleaving agents and each cleavable linker is cleaved by only one of the cleaving agents and not the other cleaving agent and the agent that cleaves each cleavable linker is different. In embodiments, an orthogonally is a cleavable linker that following cleavage the two separated entities (e.g., fluorescent dye, bioconjugate reactive group) do not further react and form a new orthogonally cleavable linker.

In embodiments, $L^{100}$ is a cleavable linker comprising an azido moiety, a disulfide moiety, or an alkoxyalkyl moiety. In embodiments, $L^{100}$ is

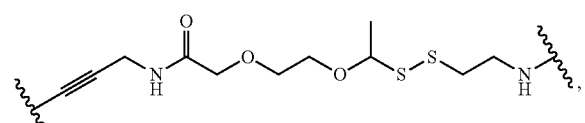

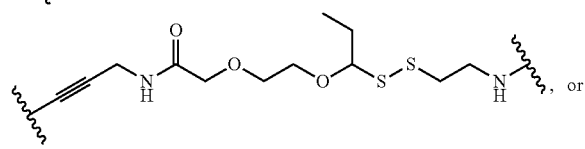

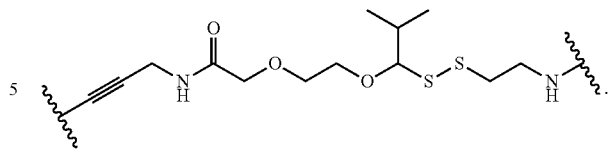

In embodiments, $L^{100}$ is

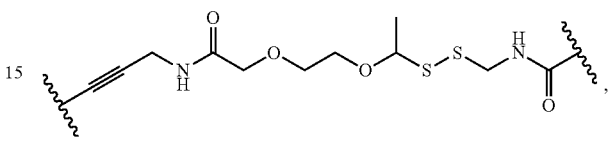

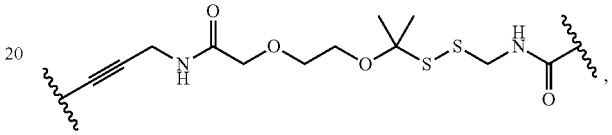

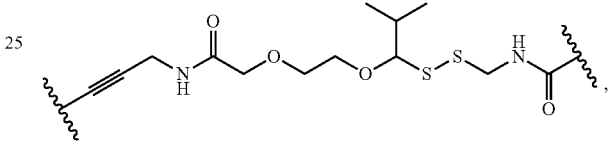

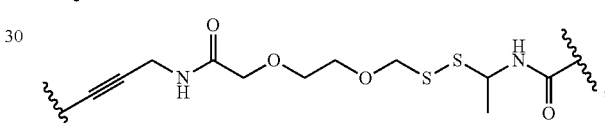

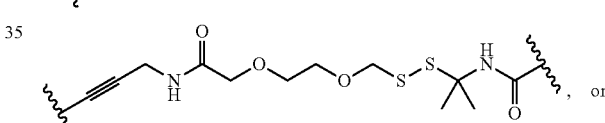, or

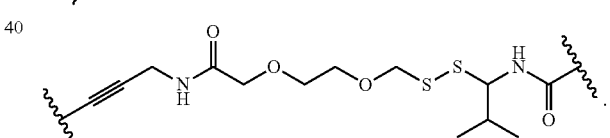

In embodiments, $L^{100}$ is

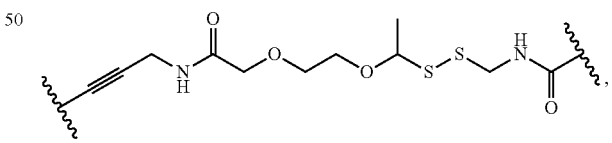

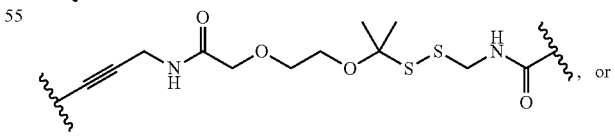, or

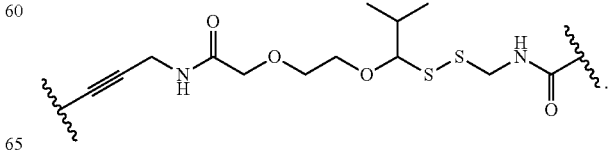

In embodiments, $L^{100}$ is
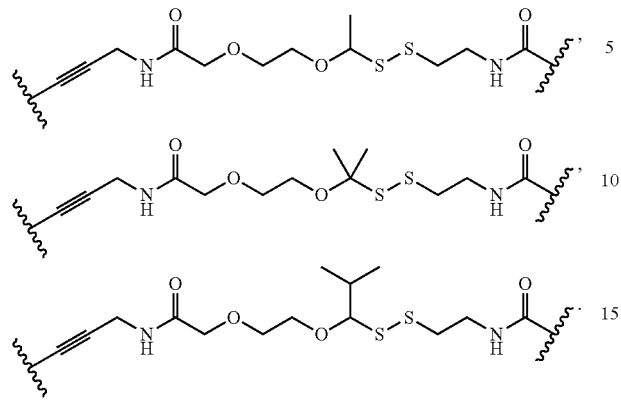
In embodiments, $L^{100}$ is
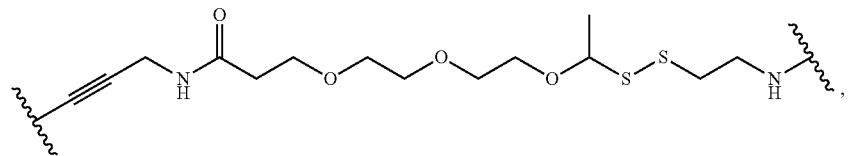
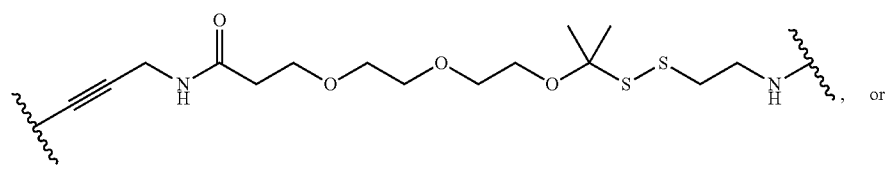, or
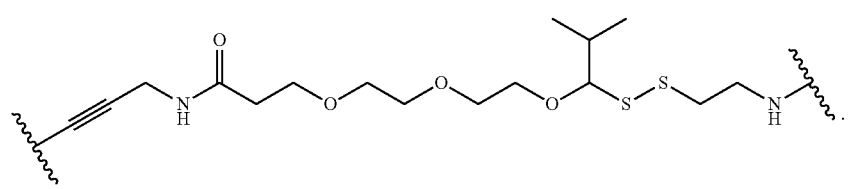.

In embodiments, $L^{100}$ is
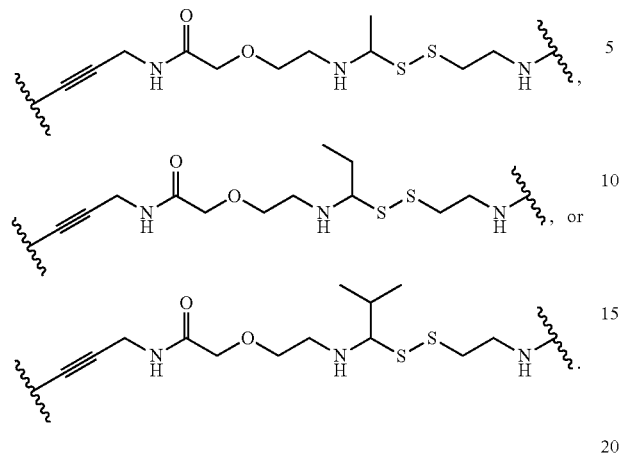
In embodiments, $L^{100}$ is
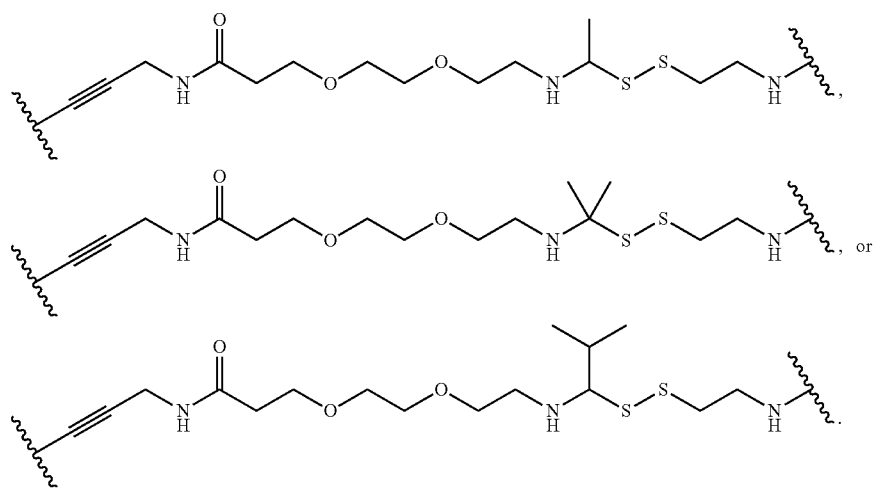
In embodiments, $L^{100}$ is
In embodiments, $L^{100}$ is
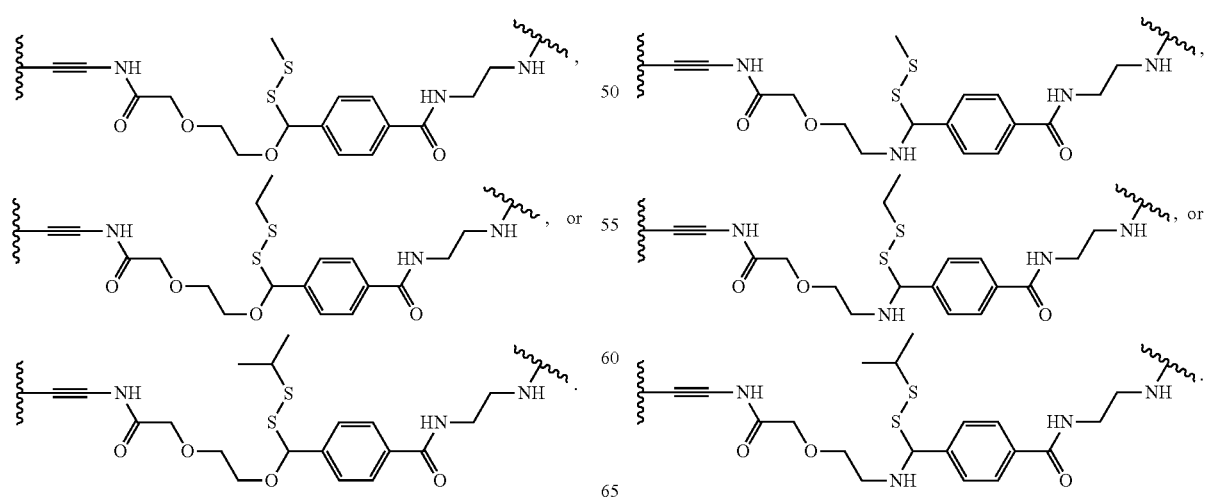

In embodiments, $L^{100}$ is
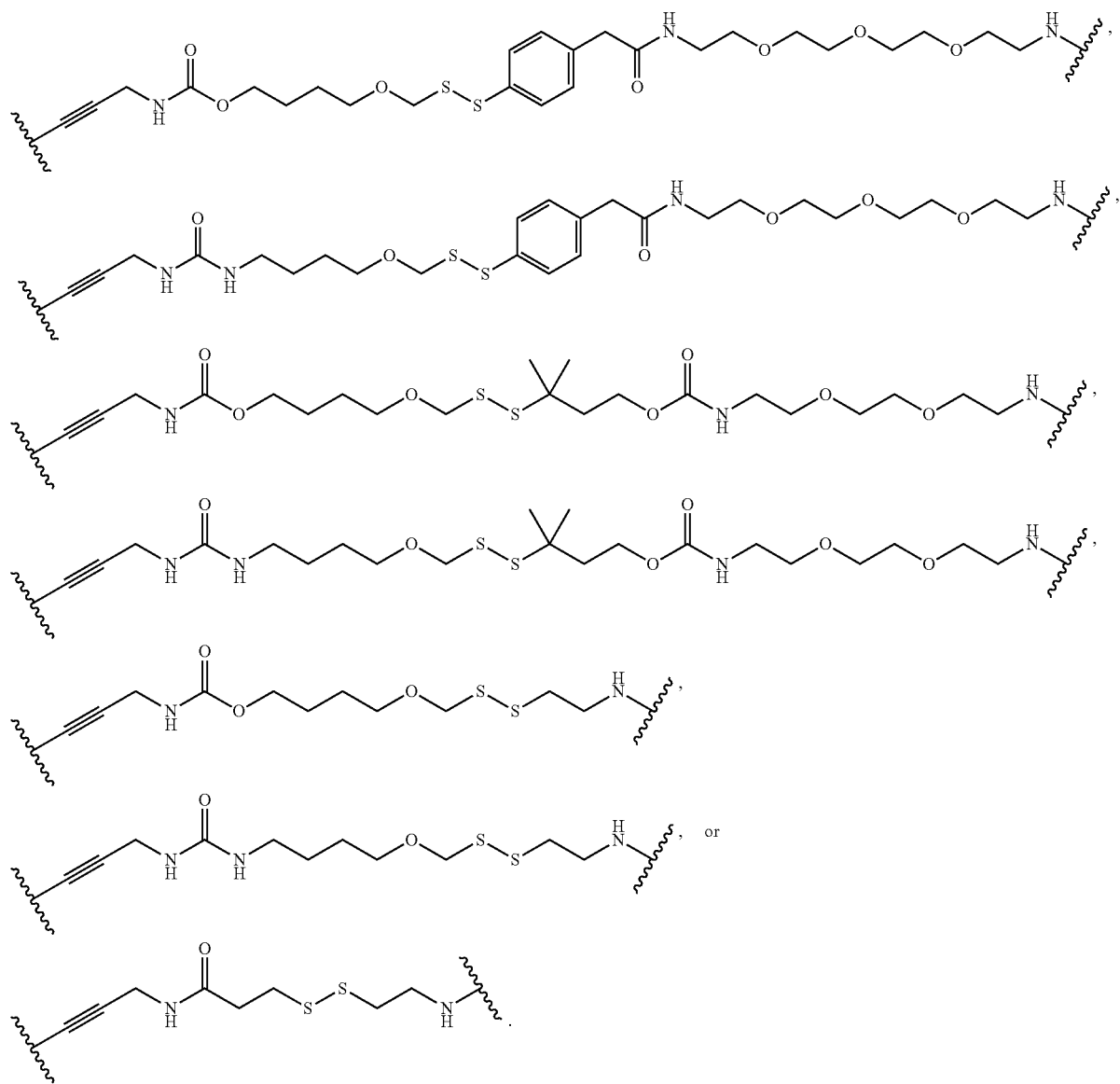
In embodiments, $L^{100}$ is
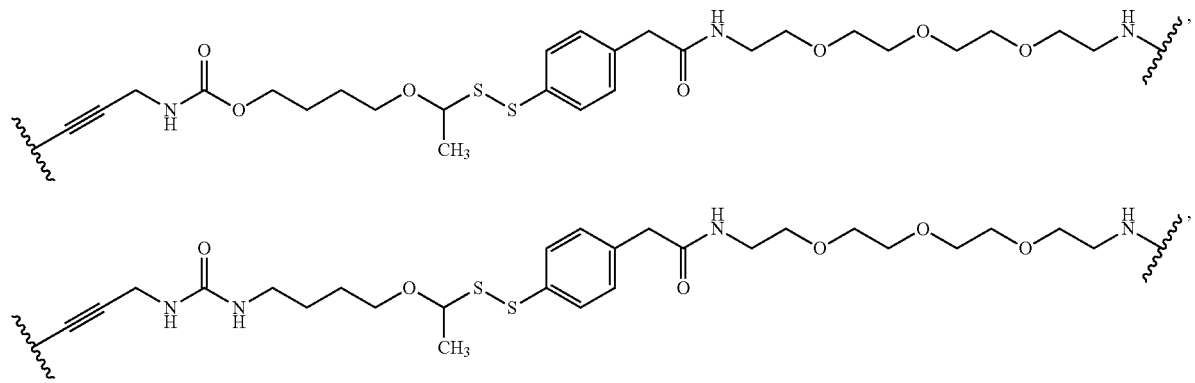

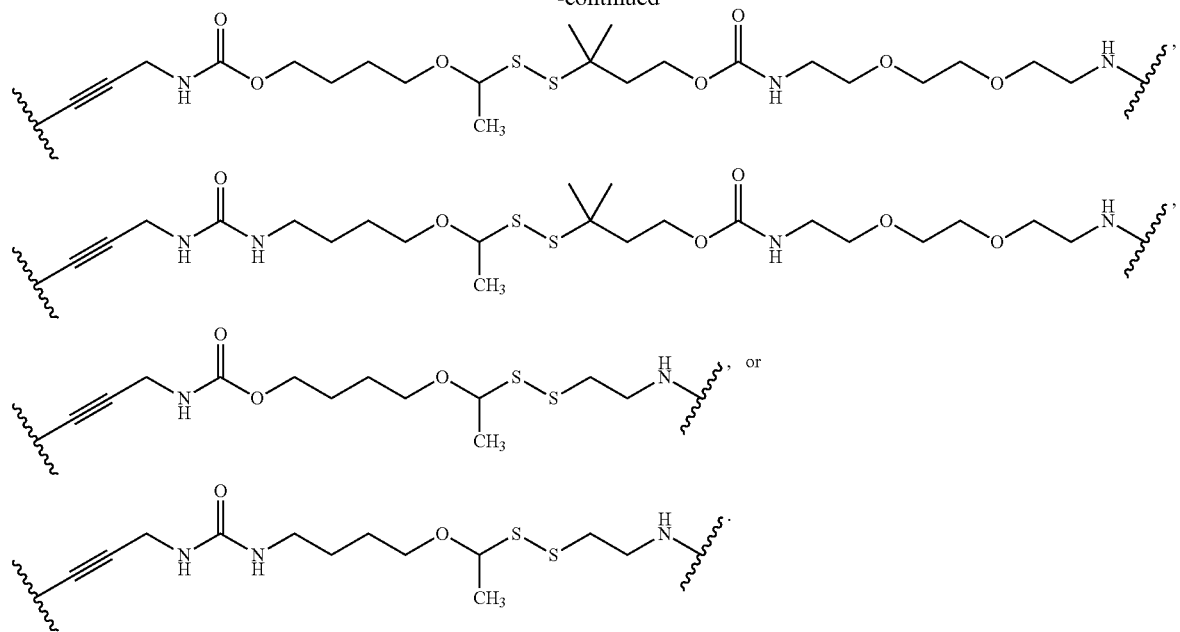
In embodiments, $L^{100}$ is
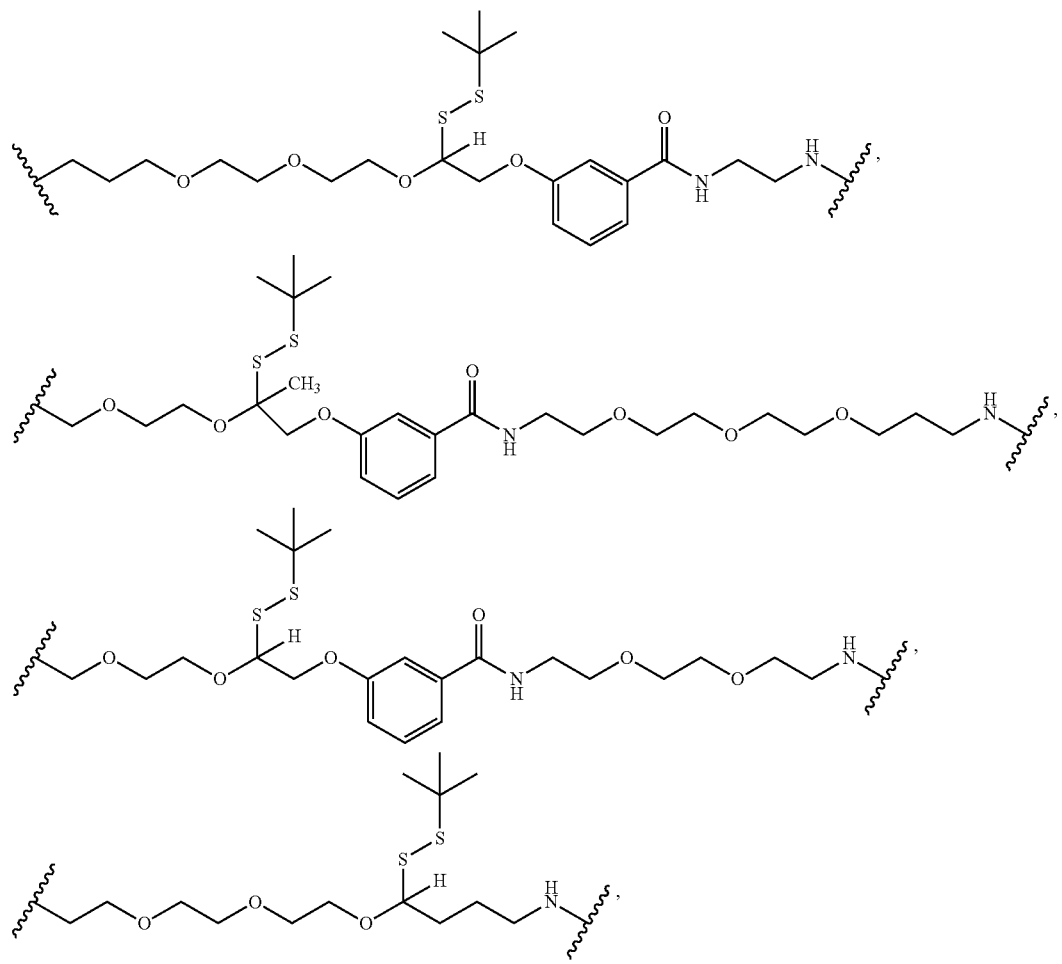

-continued
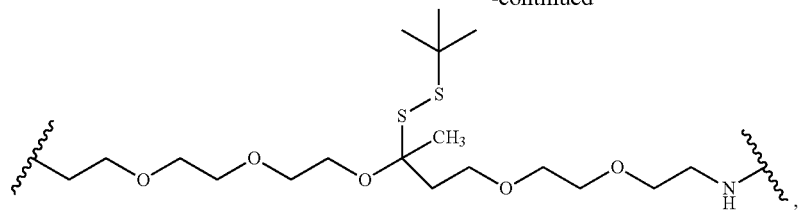
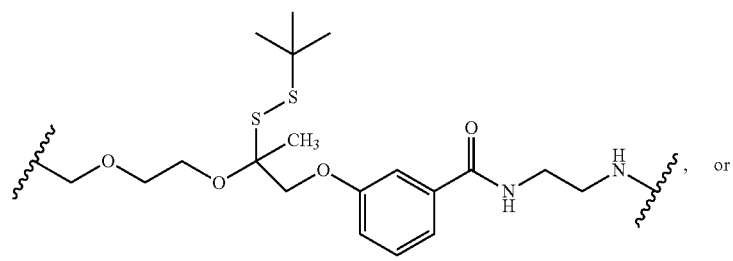, or
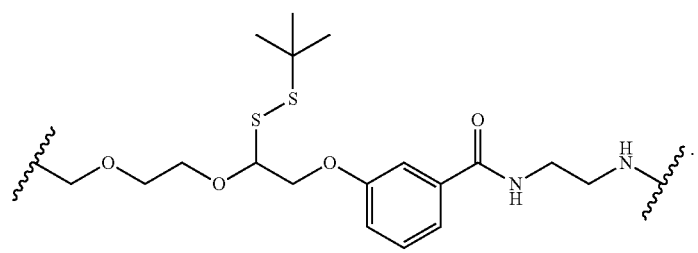 [SMILES: *COCCOC(COc1cccc(C(=O)NCCN*)c1)SSC(C)(C)C]
In embodiments, L$^{100}$ is
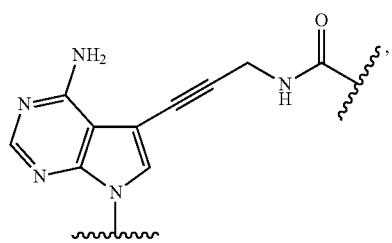
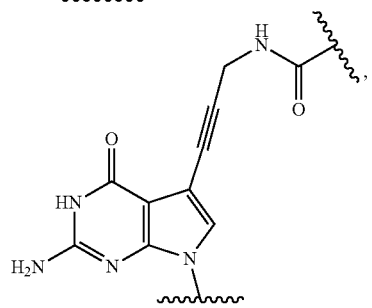
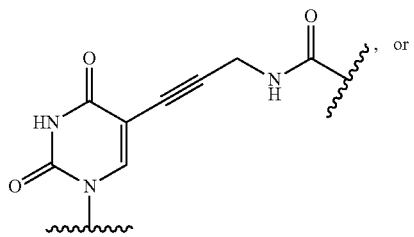, or
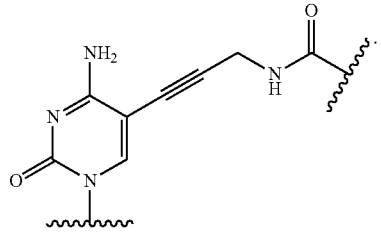
In embodiments, L$^{100}$ is
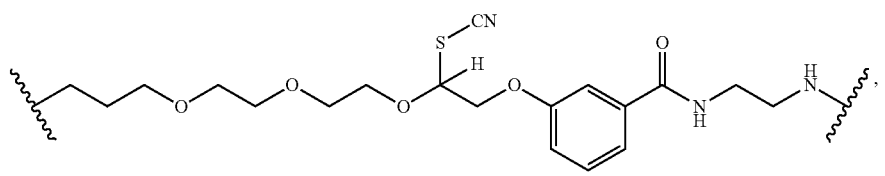

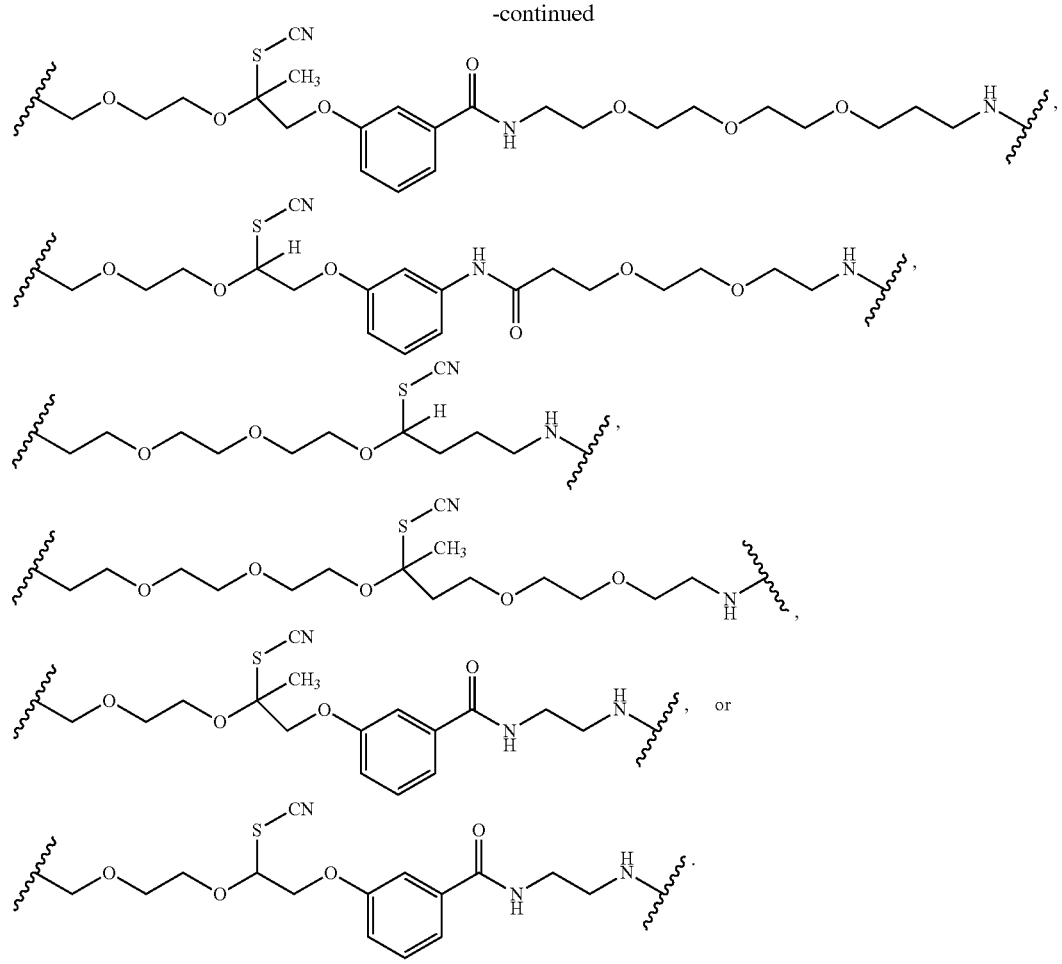
In embodiments, B is
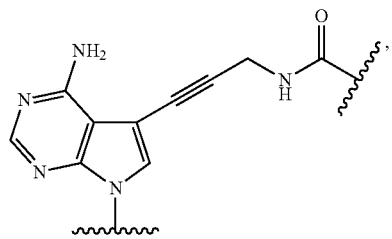
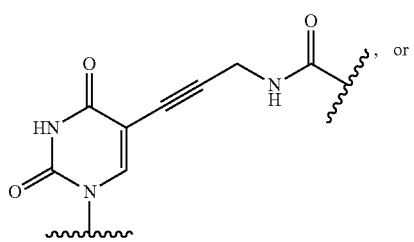
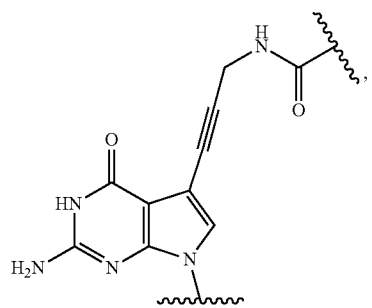
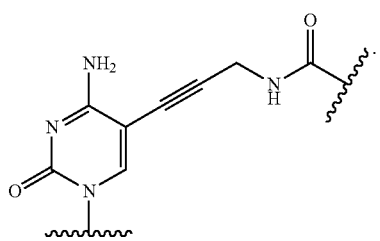

In embodiments, L$^{100}$ is
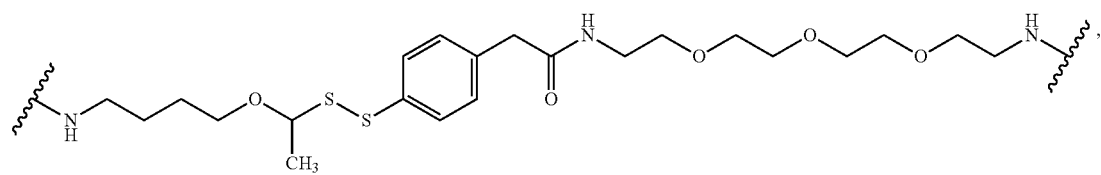
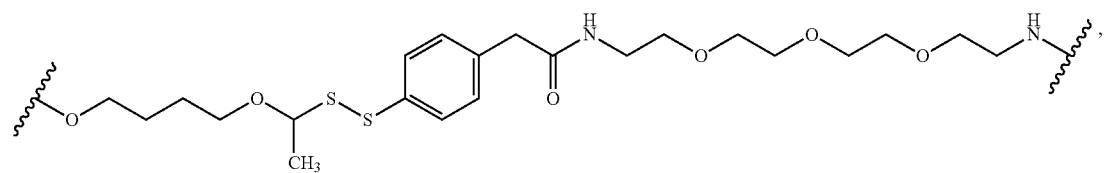
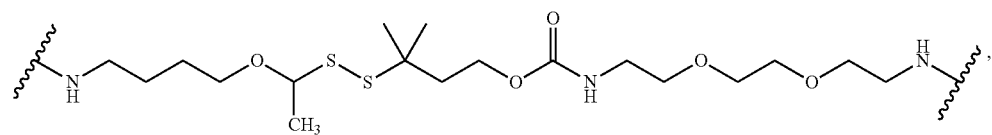
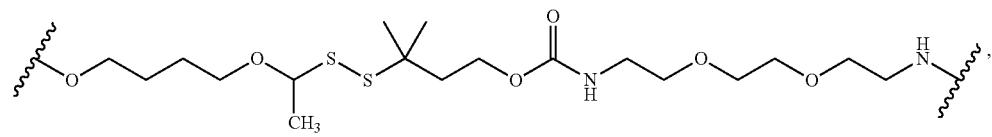
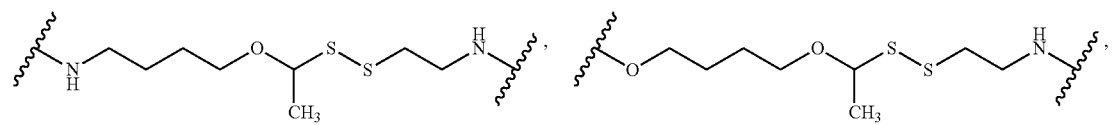
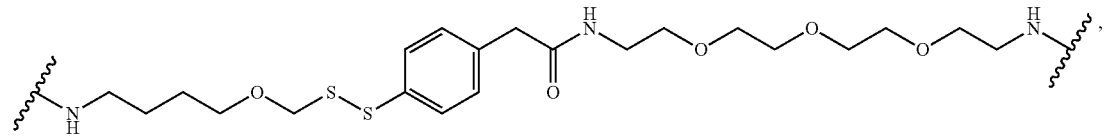
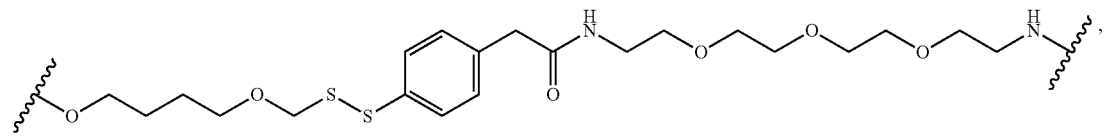
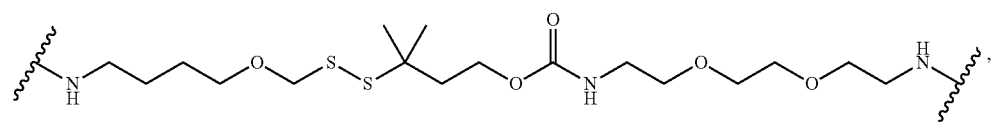
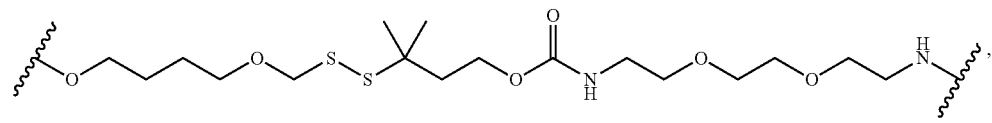
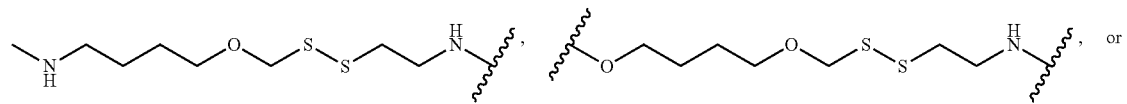
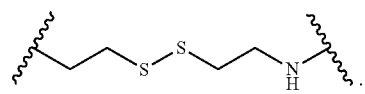

In embodiments, B is
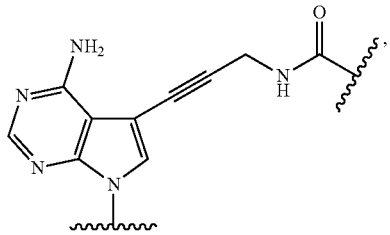
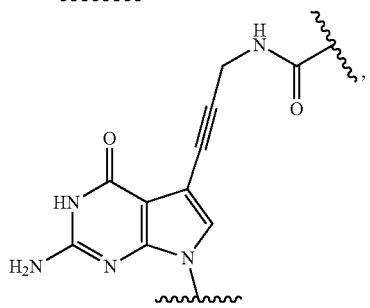
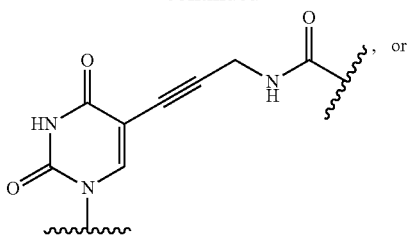
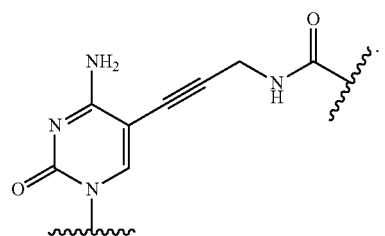
In embodiments, $L^{100}$ is
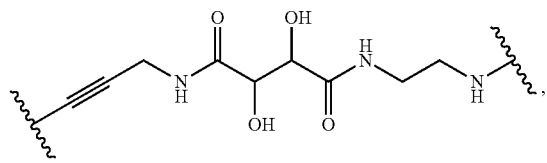
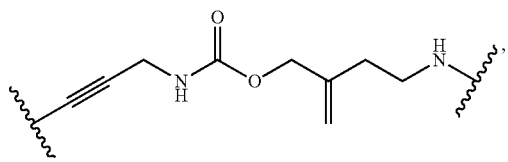
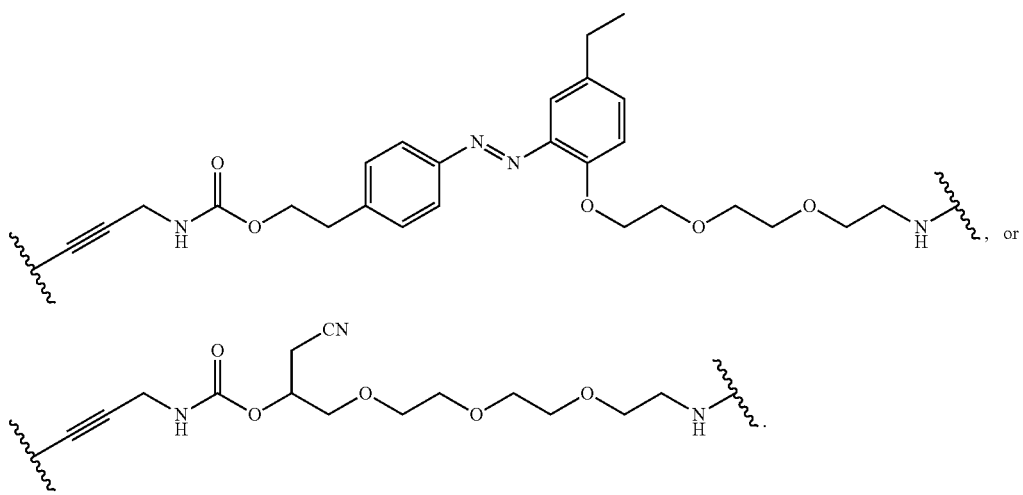

In embodiments, $L^{100}$ is
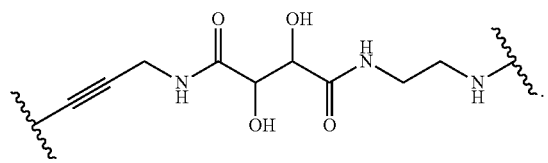 [SMILES: *C#CCNC(=O)C(O)C(O)C(=O)NCCN*]
In embodiments, $L^{100}$ is
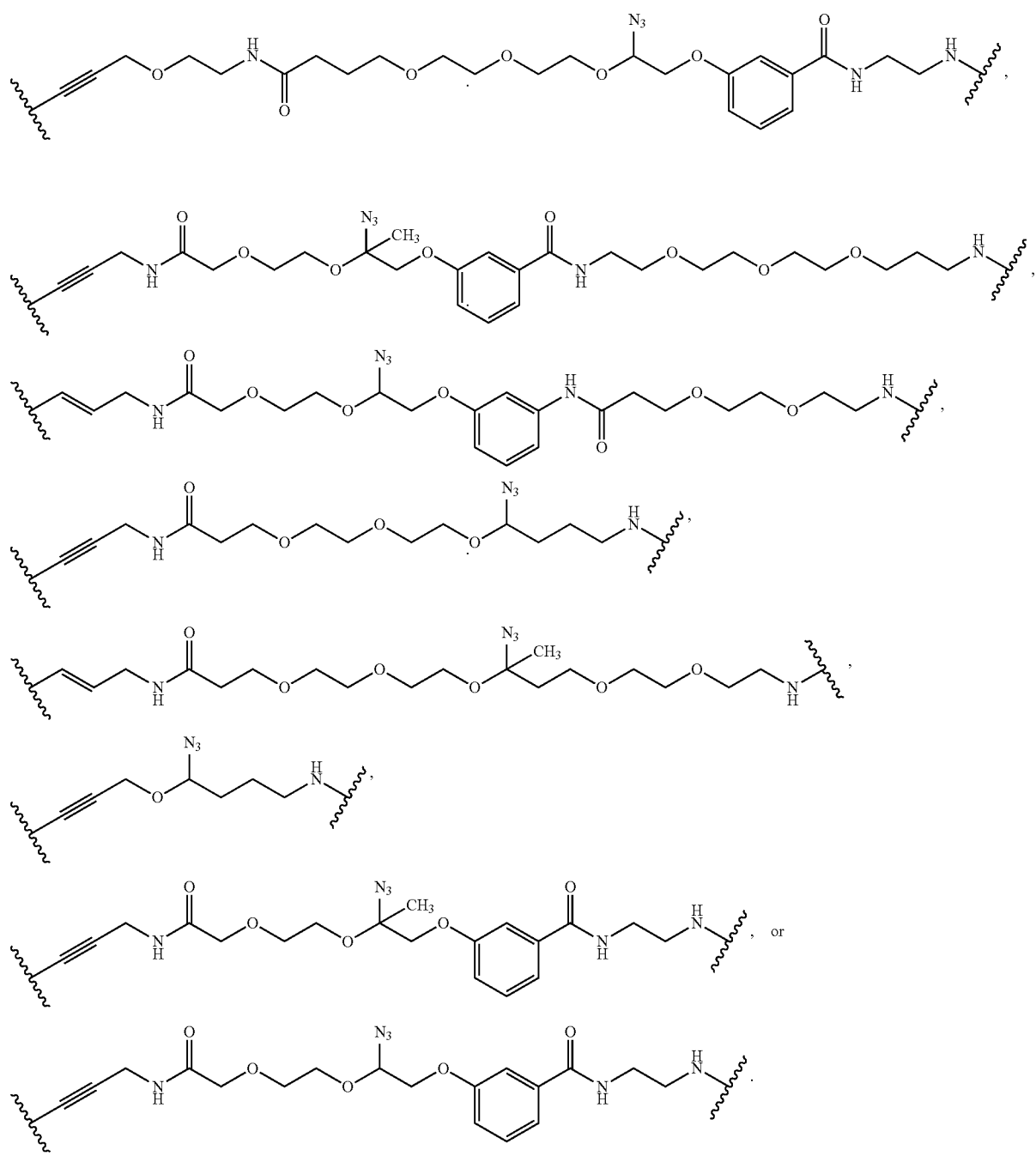

In embodiments, L¹⁰⁰

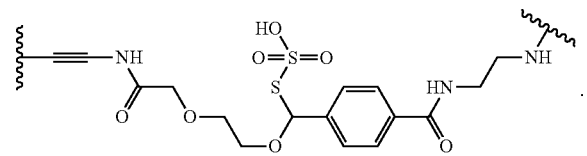 [SMILES: *C#CNC(=O)COCCOC(SS(=O)(=O)O)c1ccc(C(=O)NCCN*)cc1]

In embodiments, L¹⁰⁰ is

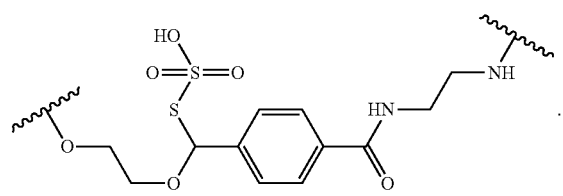 [SMILES: *NCCNC(=O)c1ccc(C(OCCO*)SS(=O)(=O)O)cc1]

Methods for cleaving the disulfide bond of —S—SO₃H bonds are known in the art, see for example Meguro et al. Tetrahedron Letters 61 (2020): 152198, which is incorporated herein by reference in its entirety. In embodiments, the cleaving agent is aqueous sodium sulfide (Na₂S). In embodiments, the cleaving agent is TCEP or THPP.

In embodiments, R¹ is a triphosphate moiety.

In embodiments, R² is hydrogen.

In embodiments, the reversible terminator includes an azido moiety, a disulfide moiety, or an alkoxyalkyl moiety. In embodiments, the reversible terminator moiety is

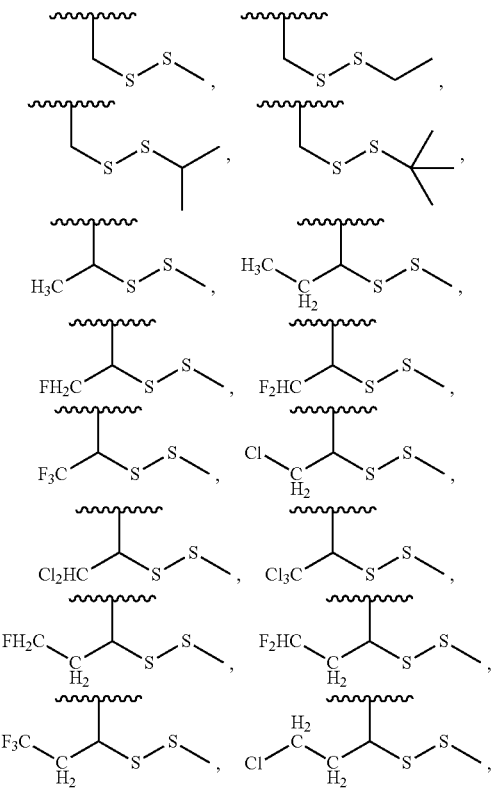

-continued

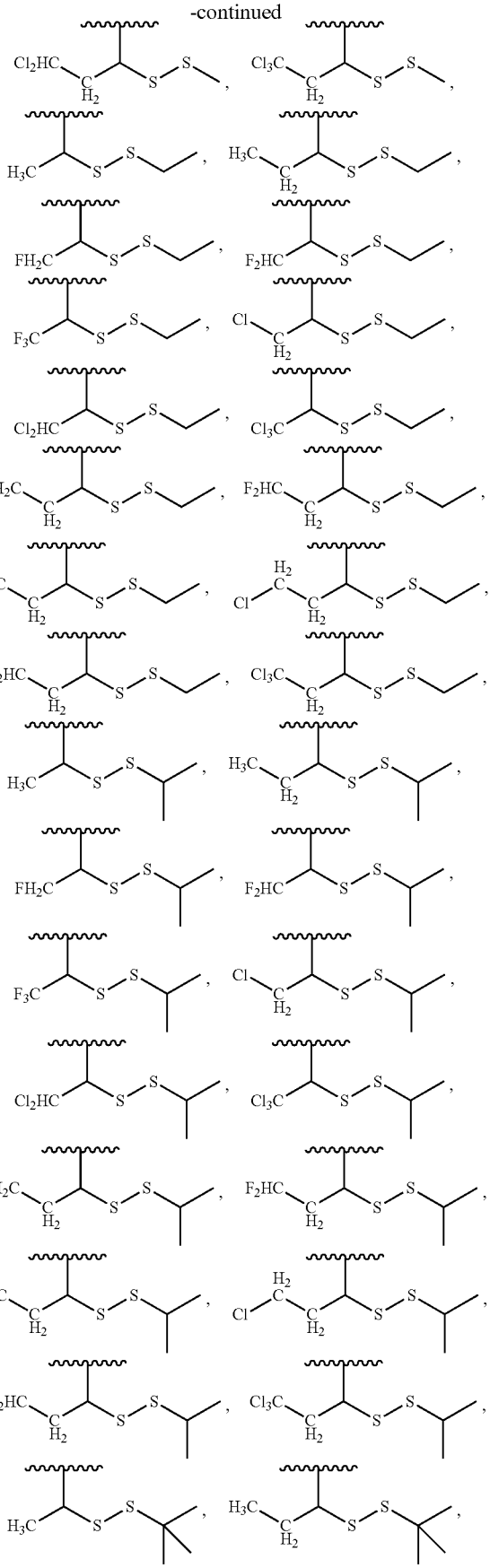

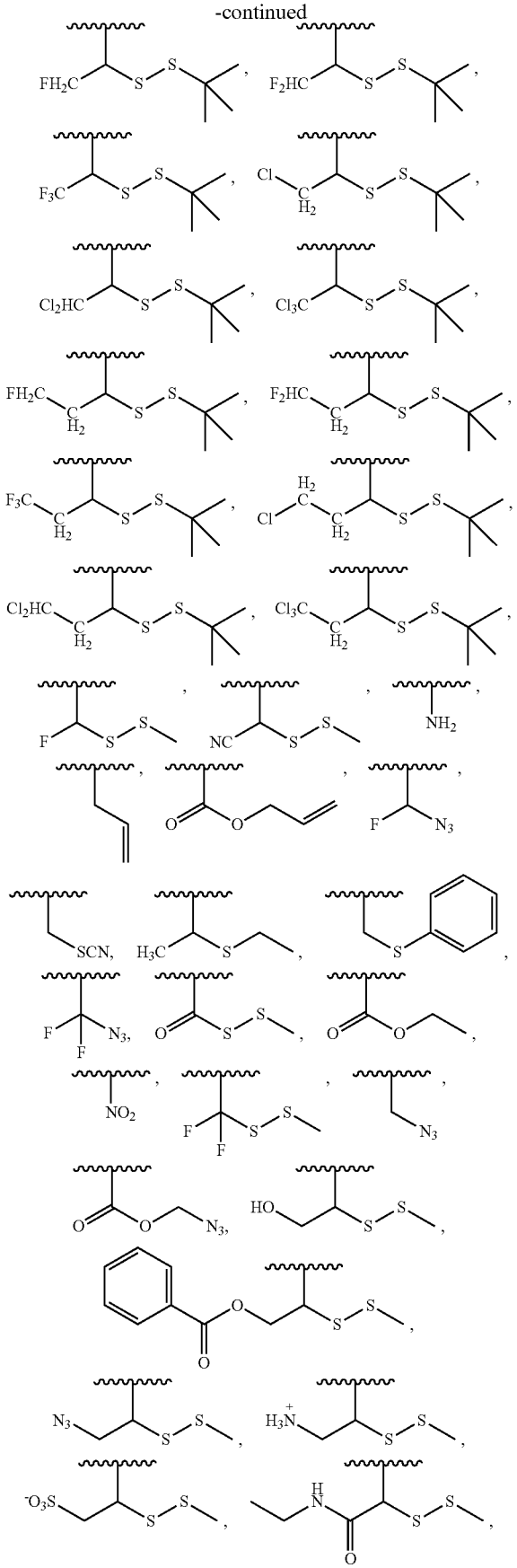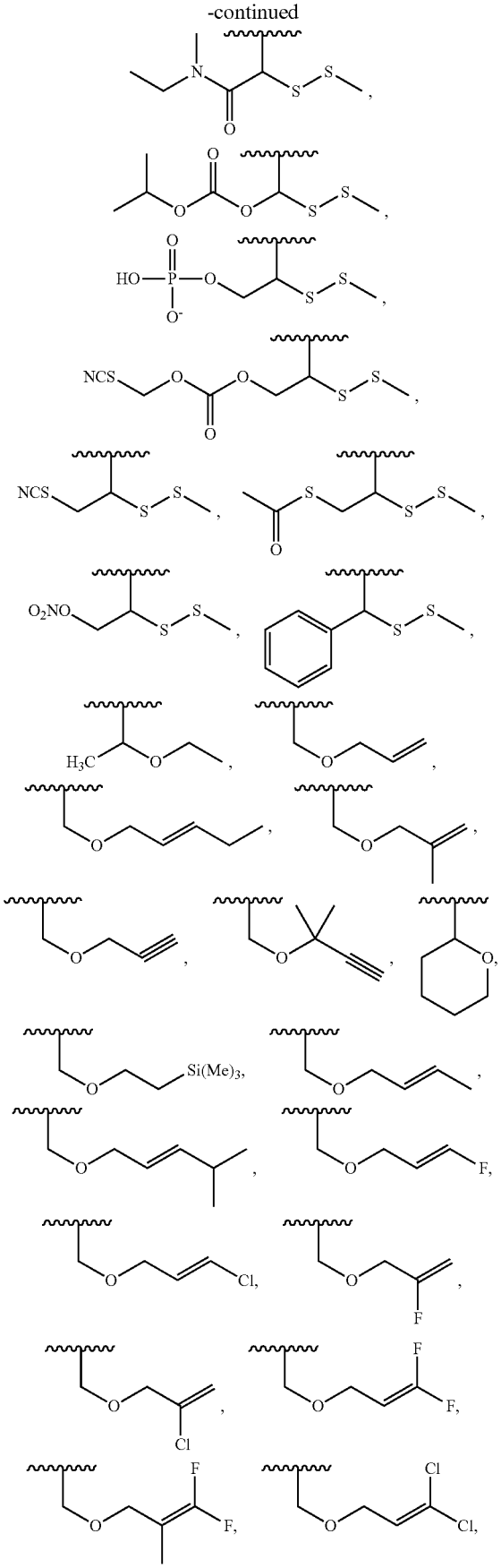

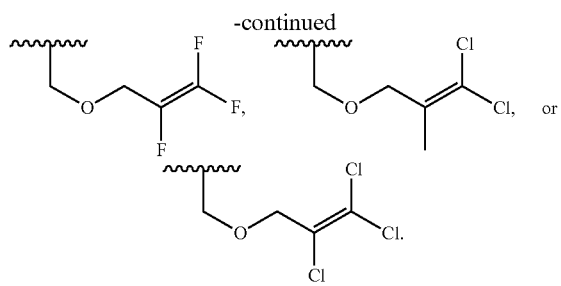

In embodiments, the nucleotides lacking a free 3'-OH include a detectable label. Typical modified nucleotides attach a unique detectable label to the specific location of the base using a cleavable linker and capping the 3'-OH group with a small reversible-terminating moiety so they are still recognized by DNA polymerase as substrates. Examples of detectable labels include imaging agents, including fluorescent and luminescent substances, molecules, or compositions, including, but not limited to, a variety of organic or inorganic small molecules commonly referred to as "dyes," "labels," or "indicators." Examples of fluorophores that may be included in the compounds and compositions described herein include fluorescent proteins, xanthene derivatives (e.g., fluorescein, rhodamine, Oregon green, eosin, or Texas red), cyanine and derivatives (e.g., cyanine, indocarbocyanine, oxacarbocyanine, thiacarbocyanine, or merocyanine), napththalene derivatives (e.g., dansyl or prodan derivatives), coumarin and derivatives, oxadiazole derivatives (e.g., pyridyloxazole, nitrobenzoxadiazole or benzoxadiazole), anthracene derivatives (e.g., anthraquinones, DRAQ5™ (Biostatus Limited), DRAQ7™ (Biostatus Limited), or CyTRAK Orange™ (Biostatus Limited), pyrene derivatives (e.g., cascade blue and derivatives), oxazine derivatives (e.g., Nile red, Nile blue, cresyl violet, or oxazine 170), acridine derivatives (e.g., proflavin, acridine orange, acridine yellow), arylmethine derivatives (e.g., auramine, crystal violet, or malachite green), tetrapyrrole derivatives (e.g., porphin, phthalocyanine, bilirubin), CF® dye, DRAQ™, CyTRAK™, BODIPY™, Alexa Fluor™, DyLight Fluor™, Atto™, Tracy™, FluoProbes™, Abberior Dyes™, DY™ dyes, MegaStokes Dyes™, Sulfo Cy™, Seta™ dyes, SeTau™ dyes, Square Dyes™, Quasar™ dyes, Cal Fluor™ dyes, SureLight Dyes™, PerCP™, Phycobilisomes™, APC™, APCXL™ RPE™, and/or BPE™. In embodiments, the detectable label is a label in Table 1. The emission from the fluorophores can be detected by any number of methods, including but not limited to, fluorescence spectroscopy, fluorescence microscopy, fluorimeters, fluorescent plate readers, infrared scanner analysis, laser scanning confocal microscopy, automated confocal nanoscanning, laser spectrophotometers, fluorescent-activated cell sorters (FACS), image-based analyzers and fluorescent scanners (e.g., gel/membrane scanners). In embodiments, the fluorophore is an aromatic (e.g., polyaromatic) moiety having a conjugated π-electron system. In embodiments, the detectable label is a fluorescent dye capable of exchanging energy with another fluorescent dye (e.g., fluorescence resonance energy transfer (FRET) chromophores).

In embodiments, the nucleotides lacking a free 3'-OH include a plurality of different nucleotides that are differently labeled. For example, the composition may include a plurality of nucleotide analogues covalently linked (e.g., covalently linked with a cleavable linker) to a first dye; a plurality of nucleotide analogues covalently linked (e.g., covalently linked with a cleavable linker) to a second dye; a plurality of nucleotide analogues covalently linked (e.g., covalently linked with a cleavable linker) to a third dye; a plurality of nucleotide analogues covalently linked (e.g., covalently linked with a cleavable linker) to a fourth dye; wherein each dye is spectrally distinct from each other. In embodiments, the composition includes a plurality of adenine or adenine analogues covalently linked (e.g., covalently linked with a cleavable linker) to a first dye; a plurality of thymine or thymine analogues covalently linked (e.g., covalently linked with a cleavable linker) to a second dye; a plurality of guanine or guanine analogues covalently linked (e.g., covalently linked with a cleavable linker) to a third dye; a plurality of cytosine or cytosine analogues covalently linked (e.g., covalently linked with a cleavable linker) to a fourth dye; wherein each dye is spectrally distinct from each other. Alternatively, the composition may be a two-color sequencing solution and contains only two dye types; see for example the compositions described in U.S. Pat. Nos. 9,222,132 and 9,453,258.

In embodiments, the composition further includes a sequencing primer, a target polynucleotide, and a sequencing polymerase, wherein the sequencing polymerase is active to extend the sequencing primer along the target polynucleotide by incorporating one of the nucleotides lacking a free 3'-OH. In embodiments, the sequencing polymerase is capable of incorporating nucleotides including a free 3'-OH and nucleotides lacking a free 3'-OH. In embodiments, the sequencing polymerase is mutated to favor incorporating nucleotides lacking a free 3'-OH over nucleotides including a free 3'-OH. In embodiments, the sequencing primer hybridizes to the target polynucleotide (e.g., a portion of the target polynucleotide complementary to the sequencing primer).

In embodiments a source nucleic acid (e.g., genomic template DNA) is treated to form target polynucleotide linear fragments (e.g., about 50 to 600 nucleotides). Treatment typically entails fragmentation, such as by chemical fragmentation, enzymatic fragmentation, or mechanical fragmentation, followed by denaturation to produce single stranded DNA fragments. In embodiments, the target polynucleotide includes an adapter. The adapter may have other functional elements including tagging sequences (i.e., a barcode), attachment sequences, palindromic sequences, restriction sites, sequencing primer binding sites, functionalization sequences, and the like. Barcodes can be any of a variety of lengths. In embodiments, the adapter includes a barcode that is 10-50, 20-30, or 4-12 nucleotides in length. In embodiments, the adapter includes a primer binding sequence that is complementary to at least a portion of the sequencing primer. Primer binding sites can be of any suitable length. In embodiments, a primer binding site is about or at least about 10, 15, 20, 25, 30, or more nucleotides in length. In embodiments, a primer binding site is 10-50, 15-30, or 20-25 nucleotides in length.

In embodiments, the composition includes a plurality of depletion templates. In embodiments, the depletion template includes a homopolymer sequence. In embodiments, the homopolymer sequence includes consecutive identical nucleotides (e.g., a 5-mer of C nucleotides). In embodiments, the homopolymer sequence includes 10 to 30 consecutive identical nucleotides. In embodiments, the homopolymer sequence includes 2 to 20 consecutive identical nucleotides. In embodiments, the homopolymer sequence includes 5 to 10 consecutive identical nucleotides. In embodiments, the homopolymer sequence includes poly (dA), poly (dT), poly (dC), poly (dG), or poly (dU) nucleotides. A depletion template can also include repeat sequences. Repeat sequences can be any of a variety of lengths including, for example, 2, 5, 10, 20, 30, 40, 50, 100, 250, 500, 1000 nucleotides or more. Repeat sequences can be repeated, either contiguously or non-contiguously, any of a variety of times including, for example, 2, 3, 4, 5, 6, 7, 8, 9, 10, 15, 20 times or more.

In embodiments, the depletion primer and the depletion template are portions of a single polynucleotide. In embodiments, the depletion primer and the depletion template are portions of a single polynucleotide including a loop structure. As used herein, the term "loop region" or "loop" refers to a region of a single polynucleotide that is between sequences of the depletion primer and the depletion template, and remains single-stranded when depletion primer and depletion template are hybridized to one another. In embodiments, the loop includes about 10 to about 20 random nucleotides. In embodiments, the loop includes a modified nucleotide (e.g., a nucleotide linked to an affinity tag) to facilitate pull-down or purification methods. In embodiments, the loop includes a biotinylated nucleotide (e.g., biotin-11-cytidine-5'-triphosphate). In embodiments, the depletion primer and the depletion template are portions of a single polynucleotide including a hairpin structure. In embodiments, the depletion primer and the depletion template are portions of a single polynucleotide including a hairpin structure and a 5' overhang. In embodiments, the depletion polymerase (e.g., TdT) is capable of incorporating nucleotides to the 3'-OH of a single polynucleotide, and thus only a depletion template is needed. In embodiments, the one or more depletion polynucleotides includes a depletion primer annealed to a depletion template.

In embodiments, the composition includes the depletion polymerase, and the nucleotides lacking a free 3'-OH include a modification that blocks strand incorporation by the depletion polymerase. In embodiments, the depletion polymerase is different than the sequencing polymerase. In embodiments, the depletion polymerase shares the same enzymatic backbone as the sequencing enzyme, however the depletion polymerase differs in the number or placement of amino acid mutations that may be present in the sequencing enzyme. For example, the depletion enzyme may be a native polymerase (e.g., a wild type *P. abyssi* enzyme) and the sequencing enzyme is a mutated polymerase such as, for example, a mutant *P. abyssi* polymerase described in WO 2018/148723 or WO 2020/056044, both of which are incorporated by reference herein.

In embodiments, the depletion polymerase is active at a temperature of about 2° C.-65° C., about 2° C.-10° C., or about 4° C.-37° C. In embodiments, the depletion polymerase is active at about 4° C. In embodiments, the depletion polymerase is active at about 37° C. In embodiments, the depletion polymerase is active at about 42° C. In embodiments, the depletion polymerase is not thermostable above 65° C. In embodiments, the depletion polymerase is not thermostable above 55° C. In embodiments, the depletion polymerase is not thermostable above 50° C. In embodiments, the depletion polymerase is not thermostable above 45° C. In embodiments, the depletion polymerase is not thermostable above 40° C. In embodiments, the depletion polymerase is active at a temperature of about 20° C.-40° C. In embodiments, the depletion polymerase is active at about 20° C. One having skill in the art would understand methods and protocols for evaluating enzymatic activity.

In embodiments, the depletion polymerase includes a Klenow fragment (e.g., Klenow (3'→5' exo-)) polymerase. In embodiments, the depletion polymerase is a Klenow fragment polymerase. In embodiments, the depletion polymerase is a Klenow polymerase. In embodiments, the depletion polymerase is a Klentaq polymerase. In embodiments, the depletion polymerase lacks exonuclease activity. In embodiments, the depletion polymerase is a Klenow Fragment (3'→5' exo-), which is an N-terminal truncation of DNA Polymerase I which retains polymerase activity, but has lost the 5'→3' exonuclease activity and has mutations (D355A, E357A) which removes the 3'→5' exonuclease activity. In embodiments, the depletion polymerase includes a mutant Klenow fragment. Mutant Klenow fragments have been described in the protein sequence of DNA polymerases I. For example, U.S. Pat. No. 6,329,178 mentions DNA polymerase mutants with altered catalytic activity in which there were mutations in the A motif (the highly conserved sequence DYSQIELR (SEQ ID NO:7), which is incorporated herein by reference in its entirety). Additionally, Minnick, T. et al., J. Biol. Chem. 274, 3067-3075 (1999), describe a wide variety of *E. coli* DNA polymerase I (Klenow fragment) mutants in which alanine exchanges have been performed. "Klenow fragment" as used herein means any C-terminal fragment of a family A DNA polymerase which has polymerase activity but no 5'→3' exonuclease activity. In embodiments, additional mutations may be introduced to remove 5'-3' exonuclease activity. In embodiments, the depletion polymerase is a Klenow fragment or mutant thereof, soluble guanylyl cyclase or mutant thereof, or a terminal deoxynucleotidyl transferase (TdT). In embodiments, the depletion polymerase is a polymerase including an amino acid sequence that is at least 80% identical to a continuous 500 amino acid sequence within SEQ ID NO: 5, at least one mutation at amino acid position 32 or an amino acid position functionally equivalent to amino acid position 32; a mutation at amino acid position 34 or an amino acid position functionally equivalent to amino acid position 34; or a mutation at amino acid position 584 or an amino acid position functionally equivalent to amino acid position 584.

In an aspect is provided a polymerase including an amino acid sequence that is at least 80% identical to a continuous 500 amino acid sequence within SEQ ID NO: 5, at least one mutation at amino acid position 32 or an amino acid position functionally equivalent to amino acid position 32; a mutation at amino acid position 34 or an amino acid position functionally equivalent to amino acid position 34; or a mutation at amino acid position 584 or an amino acid position functionally equivalent to amino acid position 584.

In embodiments, the polymerase is exo-/exo variant (i.e., does not include 3'-5' or 5'-3' exonuclease activity). Examples of mutations giving rise to an exo-/exo variants include mutations at positions in a parent polymerase corresponding to positions in SEQ ID NO: 5 identified as follows: 32 and 34. In embodiments, the polymerase includes a valine, threonine, glycine, or alanine at amino acid position 32. In embodiments, the polymerase includes a valine at amino acid position 32. In embodiments, the polymerase includes a threonine at amino acid position 32. In embodiments, the polymerase includes a glycine at amino acid position 32. In embodiments, the polymerase includes an alanine at amino acid position 32. In embodiments, the polymerase includes a serine at amino acid position 32. In embodiments, the polymerase includes a valine, threonine, glycine, or alanine at amino acid position 34. In embodiments, the polymerase includes a valine at amino acid position 34. In embodiments, the polymerase includes a threonine at amino acid position 34. In embodiments, the polymerase includes a glycine at amino acid position 34. In embodiments, the polymerase includes an alanine at amino acid position 34. In embodiments, the polymerase includes a serine at amino acid position 34.

In embodiments, the polymerase includes an amino acid substitution at position 584. The amino acid substitution at position 584 may be a serine, glycine, threonine, asparagine, or alanine substitution. The amino acid substitution at position 584 may be a serine substitution. In embodiments, the substitution at position 584 includes a polar amino acid (e.g., threonine, asparagine, or glutamine). In embodiments, the amino acid substitution at position 584 is a selenocysteine. In embodiments, the substitution at position 584 includes a serine at amino acid position 584. In embodiments, the substitution at position 584 includes a glycine at amino acid position 584. In embodiments, the substitution at position 584 includes a threonine at amino acid position 584. In embodiments, the substitution at position 584 includes an asparagine at amino acid position 584. In embodiments, the substitution at position 584 includes an alanine at amino acid position 584.

In embodiments, the nucleotide cyclase is a soluble guanylyl cyclase (also known as guanyl cyclase, guanylyl cyclase, or GC). In embodiments, the cyclase is soluble guanylyl cyclase (e.g., soluble guanylyl cyclase α1μ1, as described in Beste et al Biochemistry. 2012; 51(1):194-204), which has both purinyl and pyrimidinyl cyclase activity and can serve to cyclize all potential nucleotides present in a nucleotide solution (e.g., A, C, G, T/U).

In embodiments, the composition is in a sequencing flow cell. Flow cells provide a convenient format for housing an array of clusters produced by the methods described herein, in particular when subjected to an SBS or other detection technique that involves repeated delivery of reagents in cycles. For example, to initiate a first SBS cycle, one or more labeled nucleotides and a DNA polymerase in a buffer can be flowed into/through a flow cell that houses an array of clusters. The clusters of an array where primer extension causes a labeled nucleotide to be incorporated can then be detected. Optionally, the nucleotides can further include a reversible termination moiety that temporarily halts further primer extension once a nucleotide has been added to a primer. For example, a nucleotide analog having a reversible terminator moiety can be added to a primer such that subsequent extension cannot occur until a deblocking agent (e.g., a reducing agent) is delivered to remove the moiety. Thus, for embodiments that use reversible termination, a deblocking reagent (e.g., a reducing agent) can be delivered to the flow cell (before, during, or after detection occurs). Washes can be carried out between the various delivery steps as needed. The cycle can then be repeated N times to extend the primer by N nucleotides, thereby detecting a sequence of length N. Example SBS procedures, fluidic systems and detection platforms that can be readily adapted for use with an array produced by the methods of the present disclosure are described, for example, in Bentley et al., Nature 456: 53-59 (2008), US 2018/0274024, WO 2017/205336, US 2018/0258472, each of which are incorporated herein in their entirety for all purposes.

In an aspect is provided a kit. The kit includes one or more of the compositions as described herein. In embodiments, the includes one or more DNA polymerases. In embodiments, the kit includes additional components, such as one or more primers, modified and/or unmodified deoxynucleotide triphosphates (dNTPs), buffers, quantification reagents, e.g., intercalating reagents, or reagents binding to the minor groove, (e.g., PicoGreen® (Molecular Probes), Sybr® Green (Molecular Probes), ethidium bromide, Gelstar™ (Cambrex) and Vista Green (Amersham)). In embodiments, the individual components of the kit can be alternatively contained either together in one storage container or separately in two or more storage containers (e.g., separate bottles or vials).

In embodiments, the kit includes nucleotides in a buffer. In embodiments, the kit includes a buffer. For example, the sequencing solution and/or the chase solution may include a buffer such as ethanolamine (EA), tris(hydroxymethyl)aminomethane (Tris), glycine, a carbonate salt, a phosphate salt, a borate salt, 2-dimethyalaminomethanol (DMEA), 2-diethyalaminomethanol (DEEA), N,N,N',N'-tetramethylethylenediamine (TEMED), and N,N,N',N'-tetraethylethylenediamine (TEEDA), and combinations thereof. For example, the buffer may Tris-HCl (pH 9.2 at 25° C.), ammonium sulfate, MgCl2, 0.1% Tween® 20, and dNTPs.

In an aspect is provided a microfluidic device for sequencing a target polynucleotide. In embodiments, the microfluidic device includes a reaction vessel for receiving a composition as described herein; one or more reservoirs including the composition as described herein; flow paths from each reservoir to the reaction vessel; and a fluidics controller that controls the flow from the reservoir to the reaction vessel.

In an aspect is provided a microfluidic device that includes a heating element (e.g., surface heater, such as a thin-film surface heater) in contact with, within close proximity to, or otherwise thermally coupled to a reservoir within a fluidic manifold (e.g., a fluidic system); the reservoir including internal channels, tunnels, pathways, or other means for controlling fluid flow. As the reagent (e.g., a composition as described herein) is moved through a reservoir zone, the surface heater heats the reagent prior to entry into the reaction vessel. In embodiments, the reservoir is heated and/or maintained at a first temperature range. The fluid system may store fluids for washing or cleaning the fluidic network of the microfluidic device, and also for diluting the reactants. For example, the fluid system may include various reservoirs to store reagents, enzymes, other biomolecules, buffer solutions, aqueous, and non-polar solutions. Furthermore, the fluid system may also include waste reservoirs for receiving waste products. As used herein, fluids may be liquids, gels, gases, or a mixture of thereof. Also, a fluid can be a mixture of two or more fluids. The fluidic network may include a plurality of microfluidic components (e.g., fluid lines, pumps, flow cells or other fluidic devices, manifolds, reservoirs) configured to have one or more fluids flowing therethrough.

In another embodiment, the microfluidic device includes a heated tube that increases the temperature of the composition as it transits from the reservoir to the reaction vessel. In embodiments, the heating element is a heated tube. The tube may be rigid (i.e., fixed) or flexible. In embodiments, a wire is wrapped on the tube and then it is covered with insulation material (e.g., Kapton, polymer, steel wire or silicone). In embodiments, the heating element is a nickel inductive heater. A heating element that includes nickel may be selected as the induction heating element in the microfluidic device because of the relatively small influence of geometries and faster thermal response. A heating element provides heat (e.g., an increase in temperature). In embodiments, the microfluidic device is a nucleic acid sequencing device, which refers to an integrated system of one or more chambers, ports, and channels that are interconnected and in fluid communication and designed for carrying out an analytical reaction or process, either alone or in cooperation with an appliance or instrument that provides support functions, such as sample introduction, fluid and/or reagent driving means, temperature control, detection systems, data collection and/or integration systems, for the purpose of determining the nucleic acid sequence of a template polynucleotide. Nucleic acid sequencing devices may further include valves, pumps, and specialized functional coatings on interior walls.

To reduce the thermal gradients that arise in a heated reaction vessel at a given temperature, $T_{rxn}$, when introducing a composition at a lower temperature, i.e., $T_{composition} < T_{rxn}$, the composition within the heated tube is heated before the composition is introduced into the heated reaction vessel. The particular dimensions of the tube can be a balance of (i) the distance between reservoir containing the unheated solution and the reaction vessel; (ii) the desired or required flow rate; (iii) the available pressure differential ($\Delta P$); and (iv) the required temperature differential ($\Delta T$). Thus, the dimensions of the tube can be specific to the instrument requirements rather than some unique combination that achieves efficient heating.

Controlling the temperature may be carried out by a variety of means. For example, in embodiments, the temperature regulation apparatus is a thermoelectric temperature controller, e.g., a Peltier heater/cooler. Alternatively, the temperature regulation apparatus may incorporate a series of channels through which is flowed a recirculating temperature controlled fluid, e.g., water, ethylene glycol or oil, which is heated or cooled to a desired temperature, e.g., in an attached water bath. By way of example, some sequencing by synthesis methods include various cycles of extension, ligation, cleavage, and/or hybridization in which it may be desired to cycle the temperature. Further, in some sequencing techniques, temperatures may range from about 0° C. to about 20° C., to a higher temperature ranging from about 50° C. to about 95° C. for denaturation and/or other reaction stages.

In embodiments, the microfluidic device includes an imaging system or detection apparatus. Any of a variety of detection apparatus can be configured to detect the reaction vessel or solid support where reagents interact. Examples include luminescence detectors, surface plasmon resonance detectors and others known in the art. Exemplary systems having fluidic and detection components that can be readily modified for use in a system herein include, but are not limited to, those set forth in U.S. Pat. Nos. 8,241,573, 8,039,817; or US Pat. App. Pub. No. 2012/0270305 A1, each of which is incorporated herein by reference. In embodiments, the microfluidic device further includes one or more excitation lasers. In embodiments, the microfluidic device is a nucleic acid sequencing device. Nucleic acid sequencing devices utilize excitation beams to excite labeled nucleotides in the DNA containing sample to enable analysis of the base pairs present within the DNA. Many of the next-generation sequencing (NGS) technologies use a form of sequencing by synthesis (SBS), wherein modified nucleotides are used along with an enzyme to read the sequence of DNA templates in a controlled manner. In embodiments, sequencing includes a sequencing by synthesis event, where individual nucleotides are identified iteratively (e.g., incorporated and detected into a growing complementary strand), as they are polymerized to form a growing complementary strand. In embodiments, nucleotides added to a growing complementary strand include both a label and a reversible chain terminator that prevents further extension, such that the nucleotide may be identified by the label before removing the terminator to add and identify a further nucleotide. Such reversible chain terminators include removable 3' blocking groups, for example as described in U.S. Pat. Nos. 10,738,072, 7,541,444 and 7,057,026. Once such a modified nucleotide has been incorporated into the growing polynucleotide chain complementary to the region of the template being sequenced, there is no free 3'-OH group available to direct further sequence extension and therefore the polymerase cannot add further nucleotides. Once the identity of the base incorporated into the growing chain has been determined, the 3' reversible terminator may be removed to allow addition of the next successive nucleotide. In embodiments, the nucleic acid sequencing device utilizes the detection of four different nucleotides that comprise four different labels.

III. Methods

In an aspect is provided a method of sequencing a target polynucleotide. In embodiments, the method includes (a) incubating the target polynucleotide in a composition described herein (e.g., a reaction mixture including a sequencing primer, nucleotides including a free 3'-OH, nucleotides lacking a free 3'-OH, and a sequencing polymerase); (b) enzymatically decreasing the amount of the nucleotides including a free 3'-OH; (c) extending the sequencing primer along the target polynucleotide using the sequencing polymerase by incorporating one of the nucleotides lacking a free 3'-OH; and (d) identifying the incorporated nucleotide. In embodiments, steps (a)-(d) are performed in a sequencing flow cell. In embodiments, steps (c)-(d) are performed in a sequencing flow cell, whereas steps (a) and (b) are performed in a container (e.g., sequencing cartridge). In embodiments, the target polynucleotide is immobilized to a solid substrate.

In an aspect is provided a method of sequencing a target polynucleotide, the method including (a) generating a refined solution by contacting a composition including a plurality of labeled nucleotides including a free 3'-OH and a plurality of labeled nucleotides lacking a free 3'-OH with one or more depleting reagents, wherein the one or more depleting reagents include: (i) one or more depletion polynucleotides and a depletion polymerase that is active to selectively incorporate the nucleotides including a free 3'-OH, wherein the depletion polynucleotide is free in solution; or (ii) one or more nucleotide cyclases that is active to selectively cyclize the nucleotides including a free 3'-OH; (b) inactivating the depletion polymerase or the one or more nucleotide cyclases; (c) contacting a sequencing primer annealed to a target polynucleotide with the refined solution and detecting the label of the incorporated labeled nucleotide lacking a free 3'-OH. In embodiments, step (c) is performed in a sequencing flow cell. In embodiments, the target polynucleotide is immobilized to a solid substrate. In embodiments, the method further includes repeating step (c) for a plurality of sequencing cycles. In embodiments, the method includes one or more wash cycles (e.g., between repeating step (c)). In embodiments, generating a refined solution occurs at a first temperature range of about 1° C. to about 45° C. In embodiments, the method includes increasing the temperature to a second temperature range and reducing the activity of the depletion polymerase. In embodiments, the depletion polymerase and the one or more depleting reagents are not removed prior to step (c). In embodiments, the depletion polymerase and the one or more depleting reagents are present during step (c).

In an aspect is provided a method of decreasing the amount of 3'-OH nucleotide in a sequencing solution, said method including: (a) contacting a sequencing solution with a depleting solution, wherein said sequencing solution includes a 3'-OH nucleotide and a plurality of labeled 3-O-blocked reversible terminator nucleotides and wherein the depleting solution includes: (i) a depletion polynucleotide and a depletion polymerase, wherein the depletion polymerase incorporates the 3'-OH nucleotide into the depletion polynucleotide thereby producing an extended depletion polynucleotide; or (ii) a nucleotide cyclase, wherein the nucleotide cyclase cyclizes the 3'-OH nucleotide thereby producing a cyclized nucleotide; and (b) inactivating the depletion polymerase or the nucleotide cyclase.

In another aspect is provided a method of depleting labeled nucleotides including a free 3'-OH in a composition including (i) labeled nucleotides including a free 3'-OH and (ii) labeled nucleotides lacking a free 3'-OH, the method including: incubating the composition with a depletion polymerase at a first temperature range of about 1° C. to about 45° C., wherein the depletion polymerase is free in solution and capable of depleting the labeled nucleotides including a free 3'-OH in the composition by selectively incorporating the nucleotides including a free 3'-OH into one or more depletion polynucleotides; or selectively cyclizing the nucleotides including a free 3'-OH with a one or more nucleotide cyclases. In embodiments, the method further includes incorporating one or more labeled nucleotides lacking a free 3'-OH into a sequencing primer hybridized to a target polynucleotide. In embodiments, the method further includes detecting the one or more labeled nucleotides (e.g., detecting the incorporated labeled nucleotide).

As used herein, the term "3'-OH nucleotide" refers to a nucleotide with an unblocked hydroxyl, wherein the oxygen atom is at the 3' position of the pentose of the nucleotide. A 3'-OH nucleotide may be incorporated into, for example, the 3' end of a polynucleotide primer by formation of a phosphodiester bond that results in a DNA extension product. As used herein, the term "labeled 3'-O-blocked reversible terminator nucleotides" refers to single nucleobases with a labeled 3'-O-blocked reversible terminator that are substrates for sequencing reactions as described herein. In embodiments, the nucleotides including a free 3'-OH have the formula:

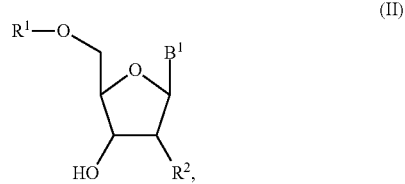

(II)

wherein $R^1$, $R^2$, and $B^1$ are as described herein, including embodiments. In embodiments, the nucleotides including a free 3'-OH have the formula (II) or (II-A).

As used herein, the term "depleting solution" is a solution that includes one or more depleting reagents (e.g., one or more depletion polynucleotides and a depletion polymerase that is active to selectively incorporate the nucleotides including a free 3'-OH, wherein the depletion polynucleotide is free in solution; or one or more nucleotide cyclases that is active to selectively cyclize the nucleotides including a free 3'-OH) used for reducing the amount of 3'-OH nucleotide in a sequencing solution.

As used herein, the term "depletion polynucleotide" refers to a polynucleotide capable of being extended by a depletion polymerase, wherein the depletion polymerase incorporates one or more 3'-OH nucleotide(s). In embodiments, the depletion polynucleotide includes a homopolymer sequence (e.g., a polyT sequence). In embodiments, the depletion polynucleotide is a single polynucleotide comprising a hairpin structure and a 5' overhang. In embodiments, the depletion polynucleotides include a depletion primer annealed to a depletion template, wherein the depletion primer has a free 3'-OH. Examples of depletion polynucleotides are provided in Table 2. A depletion polynucleotide may alternatively be referred to herein as a depletion oligonucleotide or depletion oligonucleotide template.

As used herein, the term "depletion polymerase" refers to a polymerase capable of incorporating 3'-OH nucleotides, an incapable of incorporating optionally labeled, 3'-O-blocked reversible terminator nucleotides. In embodiments, the depletion polymerase is a polymerase described herein. In embodiments, the depletion polymerase includes a Klenow fragment, or mutant thereof. In embodiments, the depletion polymerase includes a Klenow fragment. In embodiments, the depletion polymerase is a Klenow fragment, or a mutant thereof. In embodiments, the depletion polymerase is a bacterial DNA polymerase, eukaryotic DNA polymerase, archaeal DNA polymerase, viral DNA polymerase, or phage DNA polymerases.

As used herein, the term "nucleotide cyclase" refers to an enzyme capable of cyclizing a 3'-OH nucleotide, and incapable of cyclizing an optionally labeled, 3'-O-blocked reversible terminator nucleotide.

In embodiments, prior to incubating the composition is stored for at least 1 day, at least 2 days, at least 3 days, or at least 7 days. In embodiments, prior to incubating the composition is stored for about 1 week, about 2 weeks, about 3 weeks, about 4 weeks, about 5 weeks, about 6 weeks, about 7 weeks, or about 8 weeks. In embodiments, prior to incubating the composition is stored for about 1 month, about 2 months, about 3 months, about 4 months, about 5 months, about 6 months, about 7 months, about 8 months, about 9 months, about 10 months, about 11 months, or about 12 months. In embodiments, the composition is stored at about 2° C.-8° C., about 20° C.-30° C., or about 4° C.-37° C.

In embodiments, the method includes inactivating the depletion polymerase or the one or more nucleotide cyclases includes heat inactivation or chemical inactivation. In embodiments, the method includes inactivating the depletion polymerase by increasing the temperature (e.g., heat inactivation) to reduce and/or eliminate the activity of the depletion polymerase. For example, many depletion polymerases are adversely affected by high temperatures and become denatured at temperatures above 40° C. In embodiments, the method includes denaturing the depletion polymerase. Alternatively, the depletion polymerase may be rendered inactive via chemical inactivation (e.g., contacting the depletion polymerase with one or more chemical additives such as proteinase K, nonionic surfactants, SDS, or dithiothreitol). In embodiments, the method includes inactivating the depletion polymerase by contacting the depletion polymerase with a surfactant (e.g., sodium dodecyl sulfate, SDS) and a proteinase (e.g., proteinase K). SDS is a powerful anionic surfactant that at high concentrations denatures proteins by disturbing the noncovalent bonds that provide secondary protein structure. In embodiments, the chemical additive is dithiothreitol, guanidinium chloride, pronase, Triton™ X-100, or a combination of one or more of the foregoing additives.

In embodiments, the method includes incubating a composition including nucleotides including a free 3'-OH, nucleotides lacking a free 3'-OH, and one or more depletion reagents capable of decreasing the amount of the nucleotides including a free 3'-OH at a first temperature range (e.g., 1° C. to about 40° C.). In embodiments, the one or more reagents include a depletion polynucleotide (e.g., a double stranded DNA molecule). In embodiments, the one or more reagents include a depletion polynucleotide, which includes a depletion primer and a depletion template.

In embodiments, the one or more reagents include a depletion primer, a depletion template, and a depletion polymerase that is active at the first temperature range to extend the depletion primer along the depletion template by selectively incorporating the nucleotides including a free 3'-OH. In embodiments the method further includes increasing the temperature to a second temperature range (e.g., about 40° C. to about 70° C.) to reduce the activity of the depletion reagents. For example, in embodiments, the method includes incubating the mixture of nucleotides including a free 3'-OH, nucleotides lacking a free 3'-OH with a depletion primer, a depletion template, and a depletion polymerase at about 1° C. to about 25° C. While incubating at the first temperature range the amount of nucleotides including a free 3'-OH is decreased. Following incubation the temperature is increased to a second temperature range that inactivates the depletion polymerase. For example, temperature may be increased or decreased at a rate of about 0.1° C./s to about 5° C./s. In embodiments, temperature may be increased or decreased at a rate of about 0.1° C./s. In embodiments, temperature may be increased or decreased at a rate of about 0.2° C./s. In embodiments, temperature may be increased or decreased at a rate of about 0.3° C./s. In embodiments, temperature may be increased or decreased at a rate of about 0.4° C./s. In embodiments, temperature may be increased or decreased at a rate of about 0.5° C./s. In embodiments, temperature may be increased or decreased at a rate of about 0.5° C./s. In embodiments, temperature may be increased or decreased at a rate of about 0.75° C./s. In embodiments, temperature may be increased or decreased at a rate of about 1° C./s. In embodiments, temperature may be increased or decreased at a rate of about 1.25° C./s. In embodiments, temperature may be increased or decreased at a rate of about 1.5° C./s. In embodiments, temperature may be increased or decreased at a rate of about 1.75° C./s. In embodiments, temperature may be increased or decreased at a rate of about 2° C./s. In embodiments, temperature may be increased or decreased at a rate of about 2.25° C./s. In embodiments, temperature may be increased or decreased at a rate of about 2.5° C./s. In embodiments, temperature may be increased or decreased at a rate of about 2.75° C./s. In embodiments, temperature may be increased or decreased at a rate of about 3° C./s. In embodiments, temperature may be increased or decreased at a rate of about 3.25° C./s. In embodiments, temperature may be increased or decreased at a rate of about 3.5° C./s. In embodiments, temperature may be increased or decreased at a rate of about 3.75° C./s. In embodiments, temperature may be increased or decreased at a rate of about 4° C./s. In embodiments, temperature may be increased or decreased at a rate of about 4.25° C./s. In embodiments, temperature may be increased or decreased at a rate of about 4.5° C./s. In embodiments, temperature may be increased or decreased at a rate of about 4.75° C./s. In embodiments, temperature may be increased or decreased at a rate of about 5° C./s. For example, a sequencing reaction includes increasing the reaction temperature to about 55° C. to about 65° C.

In embodiments, enzymatically decreasing the amount of the nucleotides including a free 3'-OH includes a depletion polymerase extending a depletion primer along a depletion template by selectively incorporating the nucleotides including a free 3'-OH. In embodiments, enzymatically decreasing the amount of the nucleotides including a free 3'-OH includes selectively cyclizing the nucleotides including the free 3'-OH using a nucleotide cyclase. In embodiments, the nucleotide cyclase is a soluble guanylyl cyclase. In embodiments, the method decreases the amount of the nucleotides including a free 3'-OH relative to a control (e.g., the amount of nucleotides in the absence of the one or more depletion reagents).

In embodiments, the labeled nucleotide lacking a free 3'-OH has the formula:

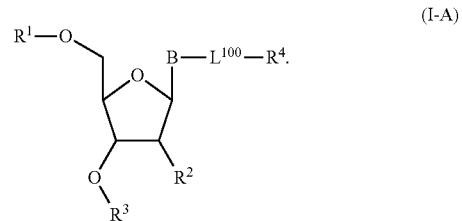

(I-A)

$R^1$ is a polyphosphate moiety, monophosphate moiety, or —OH. $R^2$ is hydrogen or —OH. $R^3$ is a reversible terminator moiety. $R^4$ is a detectable moiety. B is a divalent cytosine or a derivative thereof, divalent guanine or a derivative thereof, divalent adenine or a derivative thereof, divalent thymine or a derivative thereof, divalent uracil or a derivative thereof, divalent hypoxanthine or a derivative thereof, divalent xanthine or a derivative thereof, divalent 7-methylguanine or a derivative thereof, divalent 5,6-dihydrouracil or a derivative thereof, divalent 5-methylcytosine or a derivative thereof, or divalent 5-hydroxymethylcytosine or a derivative thereof. $L^{100}$ is a divalent linker.

In embodiments, the method includes the labeled nucleotide including a free 3'-OH has the formula:

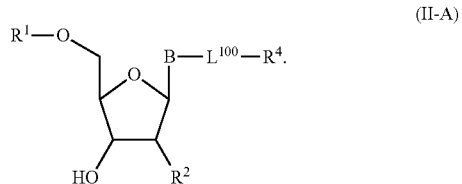

(II-A)

$R^1$ is a polyphosphate moiety, monophosphate moiety, or —OH. $R^2$ is hydrogen or —OH. $R^4$ is a detectable moiety. B is a divalent cytosine or a derivative thereof, divalent guanine or a derivative thereof, divalent adenine or a derivative thereof, divalent thymine or a derivative thereof, divalent uracil or a derivative thereof, divalent hypoxanthine or a derivative thereof, divalent xanthine or a derivative thereof, divalent 7-methylguanine or a derivative thereof, divalent 5,6-dihydrouracil or a derivative thereof, divalent 5-methylcytosine or a derivative thereof, or divalent 5-hydroxymethylcytosine or a derivative thereof. $L^{100}$ is a divalent linker.

In embodiments, $L^{100}$ is a cleavable linker. In embodiments, $L^{100}$ is a cleavable linker comprising an azido moiety, a disulfide moiety, or an alkoxyalkyl moiety.

In embodiments, $R^1$ is a triphosphate moiety.

In embodiments, $R^2$ is hydrogen. In embodiments, $R^2$ is —OH.

In embodiments, the reversible terminator includes an azido moiety, a disulfide moiety, or an alkoxyalkyl moiety.
In embodiments, the nucleotides lacking a free 3'-OH include a reversible terminator moiety (e.g., a reversible terminator moiety as described herein, including embodiments). In embodiments, the reversible terminator moiety is:
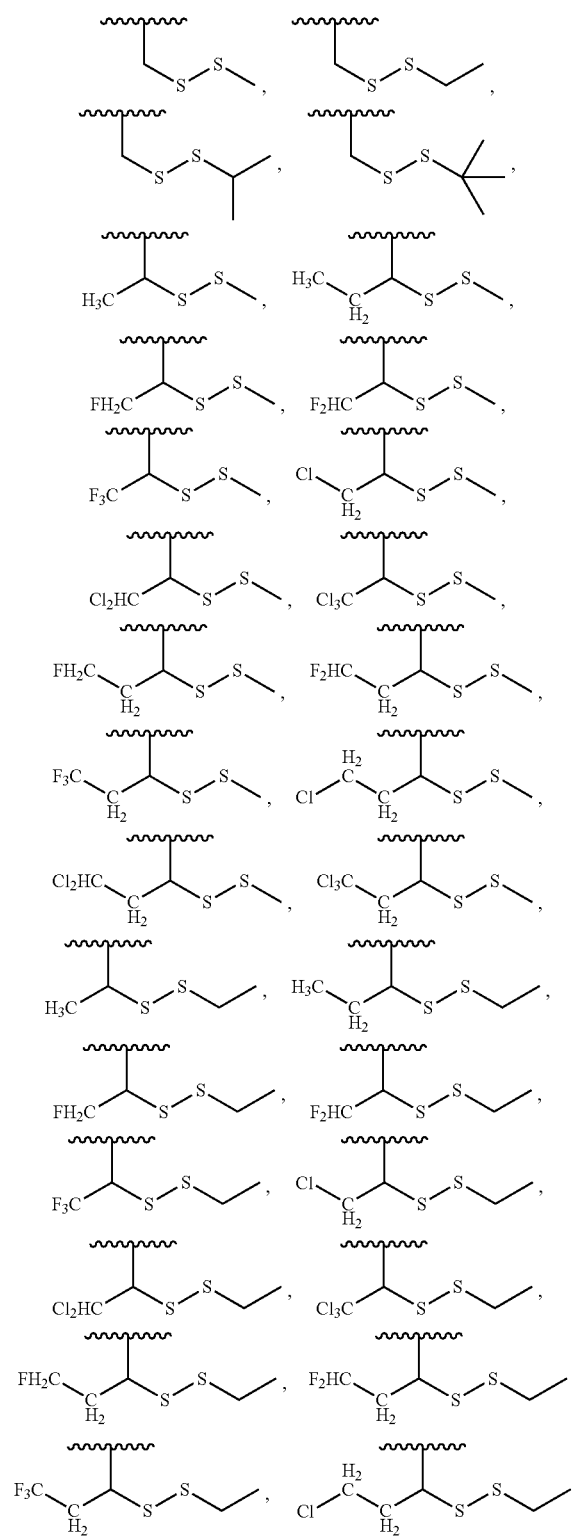
-continued
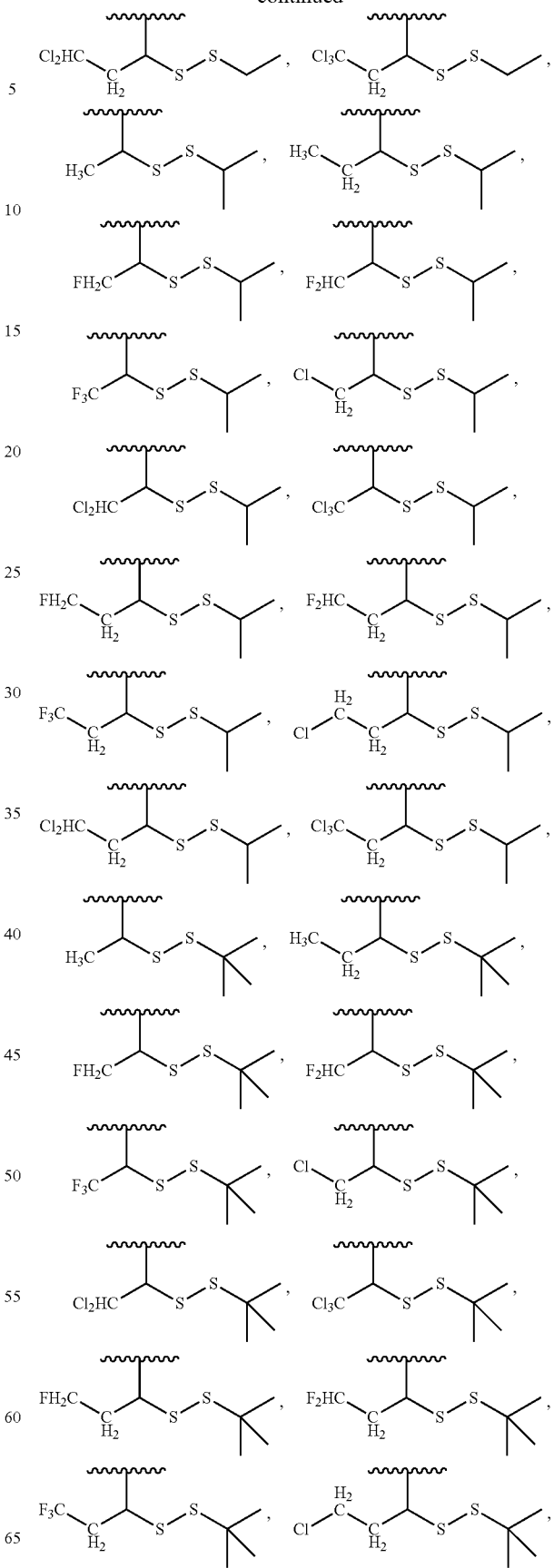

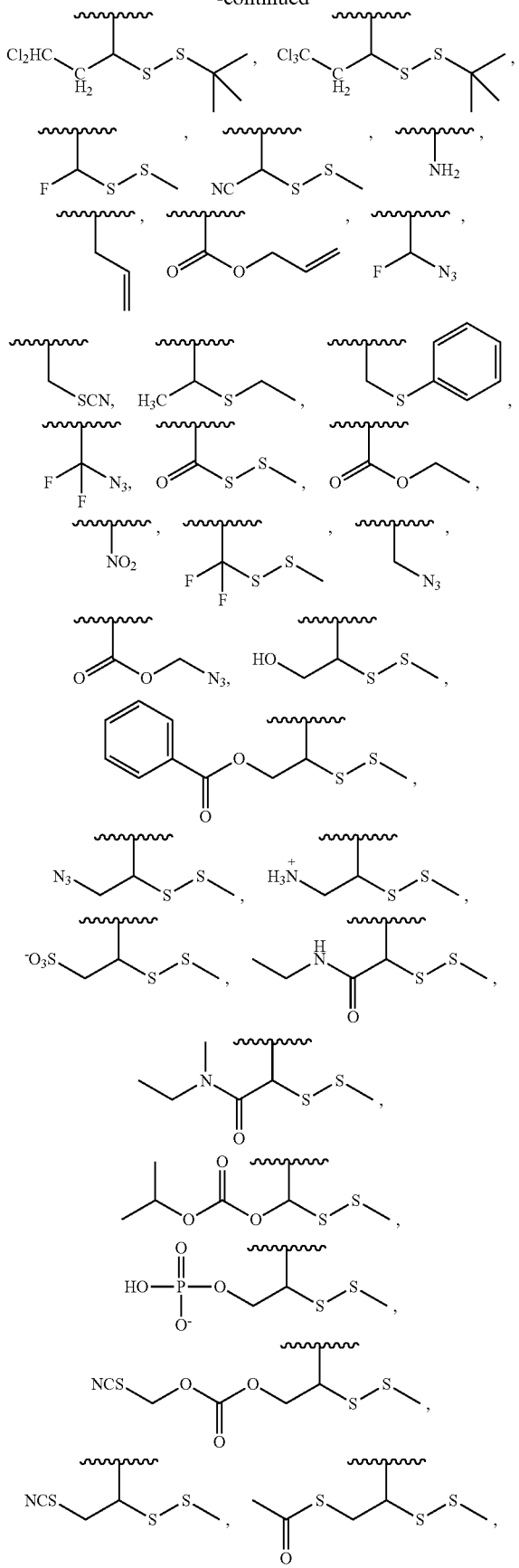

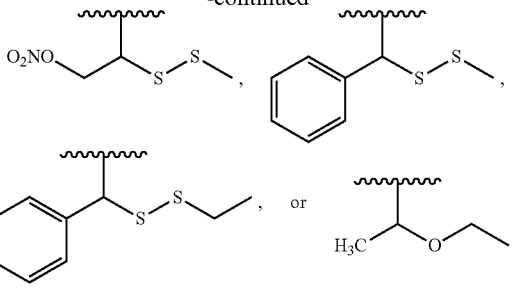

In embodiments, the reversible terminator moiety is

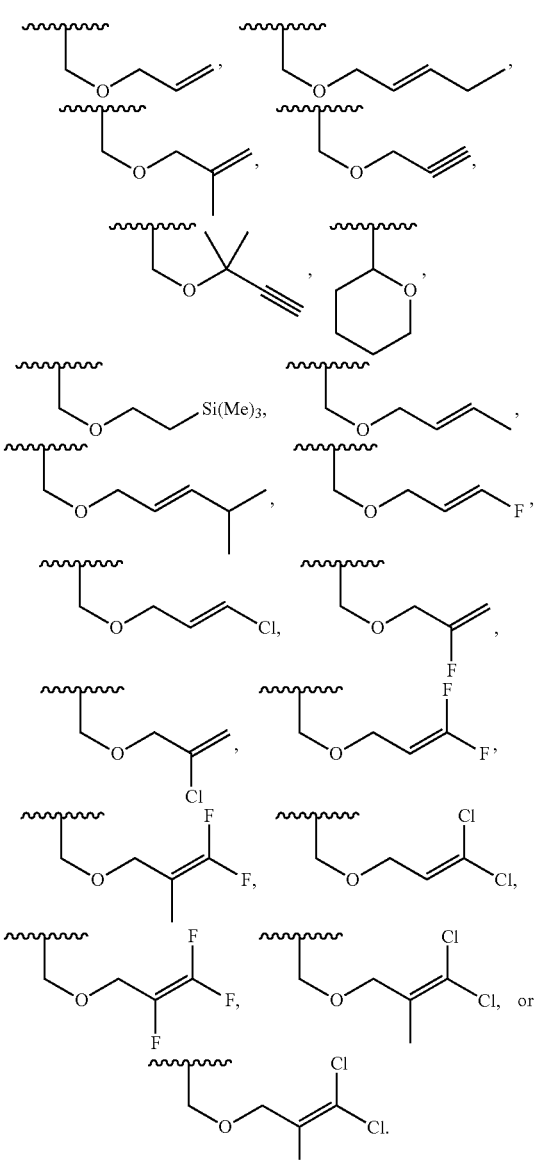

In embodiments, the nucleotides lacking a free 3'-OH include a detectable label. In embodiments, the nucleotides lacking a free 3'-OH include a plurality of different nucleotides that are differently labeled. The modified nucleotides may carry a label (e.g., a fluorescent label) to facilitate their detection. Each nucleotide type may carry a different fluorescent label. However, the detectable label need not be a fluorescent label. Any label can be used which allows the detection of an incorporated nucleotide. One method for detecting fluorescently labeled nucleotides includes using laser light of a wavelength specific for the labeled nucleotides, or the use of other suitable sources of illumination. The fluorescence from the label on the nucleotide may be detected (e.g., by a CCD camera or other suitable detection means).

In embodiments, the depletion template includes a homopolymer sequence. In embodiments, the homopolymer sequence includes consecutive identical nucleotides (e.g., a 5-mer of C nucleotides). In embodiments, the homopolymer sequence includes 10 to 30 consecutive identical nucleotides. In embodiments, the homopolymer sequence includes 2 to 20 consecutive identical nucleotides. In embodiments, the homopolymer sequence includes 5 to 10 consecutive identical nucleotides. In embodiments, the homopolymer sequence includes poly (dA), poly (dT), poly (dC), poly (dG), or poly (dU) nucleotides. A depletion template can also include repeat sequences. Repeat sequences can be any of a variety of lengths including, for example, 2, 5, 10, 20, 30, 40, 50, 100, 250, 500, 1000 nucleotides or more. Repeat sequences can be repeated, either contiguously or non-contiguously, any of a variety of times including, for example, 2, 3, 4, 5, 6, 7, 8, 9, 10, 15, 20 times or more.

In embodiments, the depletion primer and the depletion template are portions of a single polynucleotide. In embodiments, the depletion primer and the depletion template are portions of a single polynucleotide including a loop structure. As used herein, the term "loop region" or "loop" refers to a region of a single polynucleotide that is between sequences of the depletion primer and the depletion template, and remains single-stranded when the depletion primer and depletion template are hybridized to one another. In embodiments, the loop includes about 10 to about 20 random nucleotides. In embodiments, the loop includes a modified nucleotide (e.g., a nucleotide linked to an affinity tag) to facilitate pull-down or purification methods. In embodiments, the loop includes a biotinylated nucleotide (e.g., biotin-11-cytidine-5'-triphosphate). In embodiments, the depletion primer and the depletion template are portions of a single polynucleotide including a hairpin structure. In embodiments, the depletion primer and the depletion template are portions of a single polynucleotide including a hairpin structure and a 5' overhang.

In embodiments, the nucleotides lacking a free 3'-OH include a modification that blocks strand incorporation by the depletion polymerase (e.g., the nucleotides include a reversible terminator moiety).

In embodiments, the depletion polymerase is active at a temperature of about 2° C.-65° C., about 2° C.-10° C., or about 4° C.-37° C. In embodiments, the depletion polymerase is active at about 4° C. In embodiments, the depletion polymerase is active at about 37° C. In embodiments, the depletion polymerase is active at about 42° C. In embodiments, the depletion polymerase is not active during step c). In embodiments, the depletion polymerase is not thermostable above 65° C. In embodiments, the depletion polymerase is active at a temperature of about 20° C.-40° C. In embodiments, the depletion polymerase is active at about 20° C.

In embodiments, the depletion polymerase is a polymerase described herein. In embodiments, the depletion polymerase includes a Klenow fragment, or mutant thereof. In embodiments, the depletion polymerase includes a Klenow fragment. In embodiments, the depletion polymerase is a Klenow fragment, or a mutant thereof. In embodiments, the depletion polymerase is a bacterial DNA polymerase, eukaryotic DNA polymerase, archaeal DNA polymerase, viral DNA polymerase, or phage DNA polymerases. Bacterial DNA polymerases include *E. coli* DNA polymerases I, II and III, IV and V, the Klenow fragment of *E. coli* DNA polymerase, *Clostridium stercorarium* (Cst) DNA polymerase, *Clostridium thermocellum* (Cth) DNA polymerase and *Sulfolobus solfataricus* (Sso) DNA polymerase. Eukaryotic DNA polymerases include DNA polymerases α, β, γ, δ, ε, η, ζ, λ, σ, μ, and κ, as well as the Rev1 polymerase (terminal deoxycytidyl transferase) and terminal deoxynucleotidyl transferase (TdT). Viral DNA polymerases include T4 DNA polymerase, phi-29 DNA polymerase, GA-1, phi-29-like DNA polymerases, PZA DNA polymerase, phi-15 DNA polymerase, Cpl DNA polymerase, Cpl DNA polymerase, T7 DNA polymerase, and T4 polymerase. Other useful DNA polymerases include thermostable and/or thermophilic DNA polymerases such as *Thermus aquaticus* (Taq) DNA polymerase, *Thermus filiformis* (Tfi) DNA polymerase, *Thermococcus* zilligi (Tzi) DNA polymerase, *Thermus thermophilus* (Tth) DNA polymerase, *Thermus* flavusu (Tfl) DNA polymerase, *Pyrococcus* woesei (Pwo) DNA polymerase, *Pyrococcus furiosus* (Pfu) DNA polymerase and Turbo Pfu DNA polymerase, *Thermococcus litoralis* (Tli) DNA polymerase, *Pyrococcus* sp. GB-D polymerase, *Thermotoga maritima* (Tma) DNA polymerase, *Bacillus stearothermophilus* (Bst) DNA polymerase, *Pyrococcus Kodakaraensis* (KOD) DNA polymerase, Pfx DNA polymerase, *Thermococcus* sp. JDF-3 (JDF-3) DNA polymerase, *Thermococcus* gorgonarius (Tgo) DNA polymerase, *Thermococcus* acidophilium DNA polymerase; *Sulfolobus acidocaldarius* DNA polymerase; *Thermococcus* sp. go N-7 DNA polymerase; Pyrodictium occultum DNA polymerase; Methanococcus voltae DNA polymerase; Methanococcus thermoautotrophicum DNA polymerase; Methanococcus jannaschii DNA polymerase; Desulfurococcus strain TOK DNA polymerase (D. Tok Pol); *Pyrococcus abyssi* DNA polymerase; *Pyrococcus horikoshii* DNA polymerase; *Pyrococcus islandicum* DNA polymerase; *Thermococcus* fumicolans DNA polymerase; Aeropyrum pernix DNA polymerase; and the heterodimeric DNA polymerase DP1/DP2. In embodiments, the polymerase is 3PDX polymerase as disclosed in U.S. Pat. No. 8,703,461, the disclosure of which is incorporated herein by reference. In embodiments, the polymerase is a reverse transcriptase. Exemplary reverse transcriptases include, but are not limited to, HIV-1 reverse transcriptase from human immunodeficiency virus type 1 (PDB 1HMV), HIV-2 reverse transcriptase from human immunodeficiency virus type 2, M-MLV reverse transcriptase from the Moloney murine leukemia virus, AMV reverse transcriptase from the avian myeloblastosis virus, or Telomerase reverse transcriptase. In embodiments, the depletion polymerase is a nucleotide cyclase. In embodiments, the depletion polymerase is a terminal transferase (e.g., terminal deoxycytidyl transferase or terminal deoxynucleotidyl transferase (TdT)). In embodiments, the depletion polymerase is an RNA dependent polymerase. In embodiments, the depletion polymerase is a Klenow fragment or mutant thereof, soluble guanylyl cyclase or mutant thereof, or a terminal deoxynucleotidyl transferase (TdT).

In embodiments, the depletion polymerase is active at a temperature of about 1° C. to about 45° C. In embodiments, the depletion polymerase is active at a temperature of about 10° C. to about 40° C. In embodiments, the depletion polymerase is active at a temperature of about 4° C. to about 37° C. In embodiments, the depletion polymerase is not active above a temperature of about 45° C. (e.g., the thermostable polymerase does not have substantial measurable activity).

In embodiments, the target polynucleotide is within a cluster of amplicons. In embodiments, the target polynucleotide is an amplicon (i.e., the amplification product of a source nucleic acid). In embodiments, prior to step c) the method includes an amplification method. Suitable methods for amplification include, but are not limited to, the polymerase chain reaction (PCR), strand displacement amplification (SDA), transcription mediated amplification (TMA) and nucleic acid sequence based amplification (NASBA), for example, as described in U.S. Pat. No. 8,003,354, which is incorporated herein by reference in its entirety. The above amplification methods can be employed to amplify one or more nucleic acids of interest. For example, PCR, multiplex PCR, SDA, TMA, NASBA and the like can be utilized to amplify immobilized nucleic acid fragments. In embodiments, amplification includes thermal bridge polymerase chain reaction amplification; for example, as exemplified by the disclosures of U.S. Pat. Nos. 5,641,658; 7,115,400; 7,790,418; U.S. Patent Publ. No. 2008/0009420, each of which is incorporated herein by reference in its entirety. In general, bridge amplification uses repeated steps of annealing of primers to templates, primer extension, and separation of extended primers from templates. Because the forward and reverse primers are attached to the solid substrate, the extension products released upon separation from an initial template are also attached to the solid support. Both strands are immobilized on the solid substrate at the 5' end, preferably via a covalent attachment. The 3' end of an amplification product is then permitted to anneal to a nearby reverse primer, forming a "bridge" structure. The reverse primer is then extended to produce a further template molecule that can form another bridge. During bridge PCR, additional chemical additives may be included in the reaction mixture, in which the DNA strands are denatured by flowing a denaturant over the DNA, which chemically denatures complementary strands. This is followed by washing out the denaturant and reintroducing an amplification polymerase in buffer conditions that allow primer annealing and extension.

In embodiments, the amplifying includes rolling circle amplification (RCA) or rolling circle transcription (RCT) (see, e.g., Lizardi et al., Nat. Genet. 19:225-232 (1998), which is incorporated herein by reference in its entirety). Several suitable rolling circle amplification methods are known in the art. For example, RCA amplifies a circular polynucleotide (e.g., DNA) by polymerase extension of an amplification primer complementary to a portion of the input polynucleotide. This process generates copies of the circular polynucleotide template such that multiple complements of the template sequence arranged end to end in tandem are generated (i.e., a concatemer) locally preserved at the site of the circle formation. In embodiments, amplifying occurs at isothermal conditions. In embodiments, amplifying includes hybridization chain reaction (HCR). HCR uses a pair of complementary, kinetically trapped hairpin oligomers to propagate a chain reaction of hybridization events, as described in Dirks, R. M., & Pierce, N. A. (2004) PNAS USA, 101(43), 15275-15278, which is incorporated herein by reference for all purposes. In embodiments, the amplifying includes branched rolling circle amplification (BRCA); e.g., as described in Fan T, Mao Y, Sun Q, et al. Cancer Sci. 2018; 109:2897-2906, which is incorporated herein by reference in its entirety. In embodiments, the amplifying includes hyberbranched rolling circle amplification (HRCA). Hyperbranched RCA uses a second primer complementary to the first amplification product. This allows products to be replicated by a strand-displacement mechanism, which yields drastic amplification within an isothermal reaction (Lage et al., Genome Research 13:294-307 (2003), which is incorporated herein by reference in its entirety). In embodiments, amplifying includes polymerase extension of an amplification primer with an amplification polymerase.

In embodiments, the sequencing polymerase is a Taq polymerase, Therminator™ 7, 9° N polymerase (exo-), Therminator™ II, Therminator™ III, or Therminator™ IX. In embodiments, the sequencing polymerase is Therminator™ 7. In embodiments, the sequencing polymerase is 9° N polymerase (exo-). In embodiments, the sequencing polymerase is Therminator™ II. In embodiments, the sequencing polymerase is Therminator™ III. In embodiments, the sequencing polymerase is Therminator™ IX. In embodiments, the sequencing polymerase is a Taq polymerase. In embodiments, the sequencing polymerase is a sequencing polymerase. In embodiments, the sequencing polymerase is 9° N and mutants thereof. In embodiments, the sequencing polymerase is Phi29 and mutants thereof. In embodiments, the DNA polymerase is a modified archaeal DNA polymerase. In embodiments, the polymerase is a reverse transcriptase. In embodiments, the polymerase is a mutant *P. abyssi* polymerase (e.g., such as a mutant *P. abyssi* polymerase described in WO 2018/148723 or WO 2020/056044, both of which are incorporated by reference herein). In embodiments, the polymerase is DNA polymerase, a terminal deoxynucleotidyl transferase, or a reverse transcriptase. In embodiments, the enzyme is a DNA polymerase, such as DNA polymerase 812 (Pol 812) or DNA polymerase 1901 (Pol 1901), e.g., a polymerase described in US 2020/0131484, and US 2020/0181587, both of which are incorporated by reference herein.

In embodiments, the sequencing polymerase is a bacterial DNA polymerase, eukaryotic DNA polymerase, archaeal DNA polymerase, viral DNA polymerase, or phage DNA polymerases. Bacterial DNA polymerases include *E. coli* DNA polymerases I, II and III, IV and V, the Klenow fragment of *E. coli* DNA polymerase, *Clostridium stercorarium* (Cst) DNA polymerase, *Clostridium thermocellum* (Cth) DNA polymerase and *Sulfolobus solfataricus* (Sso) DNA polymerase. Eukaryotic DNA polymerases include DNA polymerases α, β, γ, δ, €, η, ζ, λ, σ, μ, and κ, as well as the Rev1 polymerase (terminal deoxycytidyl transferase) and terminal deoxynucleotidyl transferase (TdT). Viral DNA polymerases include T4 DNA polymerase, phi-29 DNA polymerase, GA-1, phi-29-like DNA polymerases, PZA DNA polymerase, phi-15 DNA polymerase, Cpl DNA polymerase, Cpl DNA polymerase, T7 DNA polymerase, and T4 polymerase. Other useful DNA polymerases include thermostable and/or thermophilic DNA polymerases such as *Thermus aquaticus* (Taq) DNA polymerase, *Thermus filiformis* (Tfi) DNA polymerase, *Thermococcus zilligi* (Tzi) DNA polymerase, *Thermus thermophilus* (Tth) DNA polymerase, *Thermus flavusu* (Tfl) DNA polymerase, *Pyrococcus woesei* (Pwo) DNA polymerase, *Pyrococcus furiosus* (Pfu) DNA polymerase and Turbo Pfu DNA polymerase, *Thermococcus litoralis* (Tli) DNA polymerase, *Pyrococcus* sp. GB-D polymerase, *Thermotoga maritima* (Tma) DNA polymerase, *Bacillus stearothermophilus* (Bst) DNA polymerase, *Pyrococcus Kodakaraensis* (KOD) DNA polymerase, Pfx DNA polymerase, *Thermococcus* sp. JDF-3 (JDF-3) DNA polymerase, *Thermococcus gorgonarius* (Tgo) DNA polymerase, *Thermococcus acidophilium* DNA polymerase; *Sulfolobus acidocaldarius* DNA polymerase; *Ther-*

*mococcus* sp. go N-7 DNA polymerase; Pyrodictium occultum DNA polymerase; Methanococcus voltae DNA polymerase; Methanococcus thermoautotrophicum DNA polymerase; Methanococcus jannaschii DNA polymerase; Desulfurococcus strain TOK DNA polymerase (D. Tok Pol); *Pyrococcus abyssi* DNA polymerase; *Pyrococcus horikoshii* DNA polymerase; *Pyrococcus islandicum* DNA polymerase; *Thermococcus* fumicolans DNA polymerase; Aeropyrum pernix DNA polymerase; and the heterodimeric DNA polymerase DP1/DP2. In embodiments, the polymerase is 3PDX polymerase as disclosed in U.S. Pat. No. 8,703,461, the disclosure of which is incorporated herein by reference. In embodiments, the polymerase is a reverse transcriptase. Exemplary reverse transcriptases include, but are not limited to, HIV-1 reverse transcriptase from human immunodeficiency virus type 1 (PDB 1HMV), HIV-2 reverse transcriptase from human immunodeficiency virus type 2, M-MLV reverse transcriptase from the Moloney murine leukemia virus, AMV reverse transcriptase from the avian myeloblastosis virus, or Telomerase reverse transcriptase.

A variety of sequencing methodologies can be used such as sequencing-by synthesis (SBS), pyrosequencing, sequencing by ligation (SBL), or sequencing by hybridization (SBH). In SBS, extension of a nucleic acid primer along a nucleic acid template is monitored to determine the sequence of nucleotides in the template. The underlying chemical process can be catalyzed by a polymerase, wherein fluorescently labeled nucleotides are added to a primer (thereby extending the primer) in a template dependent fashion such that detection of the order and type of nucleotides added to the primer can be used to determine the sequence of the template. A plurality of different nucleic acid fragments that have been attached at different locations of an array can be subjected to an SBS technique under conditions where events occurring for different templates can be distinguished due to their location in the array. In embodiments, the sequencing step includes annealing and extending a sequencing primer to incorporate a detectable label that indicates the identity of a nucleotide in the target polynucleotide, detecting the detectable label, and repeating the extending and detecting of steps. In embodiments, the methods include sequencing one or more bases of a target polynucleotide by extending a sequencing primer hybridized to a target polynucleotide. In embodiments, the sequencing step may be accomplished by a sequencing-by-synthesis (SBS) process. In embodiments, sequencing comprises a sequencing by synthesis process, where individual nucleotides are identified iteratively, as they are polymerized to form a growing complementary strand. In embodiments, nucleotides added to a growing complementary strand include both a label and a reversible chain terminator that prevents further extension, such that the nucleotide may be identified by the label before removing the terminator to add and identify a further nucleotide. Such reversible chain terminators include removable 3' blocking groups, for example as described in U.S. Pat. Nos. 7,541,444 and 7,057,026. Once such a modified nucleotide has been incorporated into the growing polynucleotide chain complementary to the region of the template being sequenced, there is no free 3'-OH group available to direct further sequence extension and therefore the polymerase cannot add further nucleotides. Once the identity of the base incorporated into the growing chain has been determined, the 3' block may be removed to allow addition of the next successive nucleotide. By ordering the products derived using these modified nucleotides it is possible to deduce the DNA sequence of the DNA template. Sequencing can be carried out using any suitable sequencing-by-synthesis (SBS) technique, wherein modified nucleotides are added successively to a free 3' hydroxyl group, typically initially provided by a sequencing primer, resulting in synthesis of a polynucleotide chain in the 5' to 3' direction. In embodiments, sequencing includes detecting a sequence of signals. In embodiments, sequencing includes extension of a sequencing primer with labeled nucleotides. Examples of sequencing include, but are not limited to, sequencing by synthesis (SBS) processes in which reversibly terminated nucleotides carrying fluorescent dyes are incorporated into a growing strand, complementary to the target strand being sequenced. In embodiments, the nucleotides are labeled with up to four unique fluorescent dyes. In embodiments, the nucleotides are labeled with at least two unique fluorescent dyes. In embodiments, the readout is accomplished by epifluorescence imaging.

In embodiments, sequencing includes a plurality of sequencing cycles. In embodiments, sequencing includes 20 to 100 sequencing cycles. In embodiments, sequencing includes 50 to 100 sequencing cycles. In embodiments, sequencing includes 50 to 300 sequencing cycles. In embodiments, sequencing includes 150 to 300 sequencing cycles. In embodiments, sequencing includes 200 to 300 sequencing cycles. In embodiments, sequencing includes 200 to 300 sequencing cycles. In embodiments, sequencing includes 50 to 500 sequencing cycles. In embodiments, sequencing includes 100 to 1000 sequencing cycles. In embodiments, sequencing includes 50 to 150 sequencing cycles. In embodiments, sequencing includes at least 10, 20, 30, 40, or 50 sequencing cycles. In embodiments, sequencing includes at least 50, 60, 70, 80, 90, or 100 sequencing cycles. In embodiments, sequencing includes at least 10 sequencing cycles. In embodiments, sequencing includes 10 to 20 sequencing cycles. In embodiments, sequencing includes 10, 11, 12, 13, 14, or 15 sequencing cycles. In embodiments, sequencing includes (a) extending a sequencing primer by incorporating a labeled nucleotide, or labeled nucleotide analogue and (b) detecting the label to generate a signal for each incorporated nucleotide or nucleotide analogue.

In embodiments, sequencing includes extending a sequencing primer to generate a sequencing read. In embodiments, sequencing includes extending a sequencing primer by incorporating a labeled nucleotide, or labeled nucleotide analogue and detecting the label to generate a signal for each incorporated nucleotide or nucleotide analogue. In embodiments, the labeled nucleotide or labeled nucleotide analogue includes a reversible terminator moiety. In embodiments, the method includes repeating the cycle of extending a sequencing primer with a labeled nucleotide analogue containing a reversible terminator moiety, detecting the labeled nucleotide analogue and removing the reversible terminator moiety and detectable label. In embodiments, the method includes one or more wash steps between each cycle to facilitate removal of the label and reversible terminator moiety from the reaction vessel (e.g., flow cell).

Use of the sequencing method outlined above is a non-limiting example, as essentially any sequencing methodology which relies on successive incorporation of nucleotides into a polynucleotide chain can be used. Suitable alternative techniques include, for example, pyrosequencing methods, FISSEQ (fluorescent in situ sequencing), MPSS (massively parallel signature sequencing), or sequencing by ligation-based methods.

In an aspect is provided a method of increasing storage stability (alternatively referred to as shelf-life) of modified nucleotides. In embodiments, the modified nucleotides are for use in a sequencing reaction. In embodiments, the method of increasing the storage stability includes (a) storing the modified nucleotides in solution at about 2° C.-65° C. for at least 12 hours, wherein the modified nucleotides include nucleotides lacking a free 3'-OH, and wherein the solution includes nucleotides including a free 3'-OH; and (b) depleting the nucleotides including a free 3'-OH during storage. In embodiments, depleting the nucleotides including a free 3'-OH during storage includes extending a depletion primer along a depletion template using a depletion polymerase that selectively incorporates the nucleotides including a free 3'-OH, wherein the depletion primer and the depletion template are free in solution. In embodiments, depleting the nucleotides including a free 3'-OH during storage includes selectively cyclizing the nucleotides including the free 3'-OH using a nucleotide cyclase. In embodiments, the method of increasing storage stability of modified nucleotides is measured relative to a control (e.g., modified nucleotides not subjected to depleting the nucleotides including a free 3'-OH during storage). In embodiments, any of the various components of the solution (e.g., the nucleotides, primer, template, polymerase, and/or nucleotide cyclase) are as described herein, such as with regard to any of the various aspects disclosed herein.

In embodiments, the method of increasing the storage stability includes (a) storing the modified nucleotides in solution at about 1° C.-40° C. for one or more minutes, wherein the modified nucleotides include nucleotides lacking a free 3'-OH, and wherein the solution includes nucleotides including a free 3'-OH; and (b) depleting the nucleotides including a free 3'-OH during storage. In embodiments, step (a) includes maintaining the modified nucleotides in solution at about 15° C.-30° C. for one or more minutes. In embodiments, step (a) includes maintaining the modified nucleotides in solution at about 15° C.-30° C. for 1, 2, 3, 4, 5, 6, 7, 8, 9, 10 or more minutes. In embodiments, step (a) includes maintaining the modified nucleotides in solution at about 15° C.-30° C. for 1, 2, 3, 4, 5, 6, 7, 8, 9, 10 or more hours.

In embodiments, the storing is for at least 1 day, 2 days, 3 days, or 7 days. In embodiments, the storing is for between at least 1 day to about 2 days. In embodiments, the storing is for at least 1 day to about 3 days. In embodiments, the storing is for at least 1 day to about 7 days. In embodiments, the storing is for more than 7 days. In embodiments, the storing is for more than 1 month.

In embodiments, the storing is at about 2° C.-8° C., about 20° C.-30° C., or about 4° C.-37° C. In embodiments, the storing is at about 2° C.-8° C. In embodiments, the storing is at about 20° C.-30° C. In embodiments, the storing is at about 4° C.-37° C. In embodiments, the storing is at about 2° C. In embodiments, the storing is at about 4° C. In embodiments, the storing is at about 8° C. In embodiments, the storing is at about 20° C. In embodiments, the storing is at about 30° C. In embodiments, the storing is at about 37° C.

In embodiments, the storing is at about 2° C.-8° C. for at least 1 day. In embodiments, the storing is at about 2° C. for at least 1 day. In embodiments, the storing is at about 4° C. for at least 1 day. In embodiments, the storing is at about 8° C. for at least 1 day.

In embodiments, the storing is at about 20° C.-30° C. for at least 1 day. In embodiments, the storing is at about 20° C. for at least 1 day. In embodiments, the storing is at about 25° C. for at least 1 day. In embodiments, the storing is at about 25° C. for at least 1, 2, 3, 4, 5 or more days. In embodiments, the storing is at about 25° C. for at least 1 day. In embodiments, the storing is at about 25° C. for at least 1 day. In embodiments, the storing is at about 25° C. for at least 1, 2, 3, 4, 5 or more weeks. In embodiments, the storing is at about 25° C. for at least 1, 2, 3, 4, 5 or more months. In embodiments, the storing is at about 30° C. for at least 1 day.

In an aspect is provided a method of increasing the shelf life of a composition including modified nucleotides, the method including: (a) storing the composition as described herein at about 1° C. to about 40° C. for one or more minutes; and (b) depleting the labeled nucleotides including a free 3'-OH during the storing, wherein the depleting includes: (i) incorporating with a depleting polymerase the nucleotides including a free 3'-OH into one or more depletion polynucleotides in solution; or (ii) selectively cyclizing the nucleotides including the free 3'-OH using a nucleotide cyclase; wherein depleting the nucleotides including a free 3'-OH increases the shelf life of the kit including modified nucleotides relative to a control (e.g., the same kit without contacting the composition one or more depleting reagents).

In embodiments, the method of increasing storage stability (i.e., the shelf life) of modified nucleotides further includes sequencing a target polynucleotide in a reaction mixture, wherein the reaction mixture includes the target polynucleotide, a sequencing primer, a sequencing polymerase, and at least a portion of the stored solution of modified nucleotides.

In embodiments, the portion of the stored solution of modified nucleotides is an unfractionated portion of the stored solution.

In an aspect is provided a method of decreasing one or more sequencing errors in a plurality of sequencing cycles, the method including (a) contacting a composition including a plurality of labeled nucleotides including a free 3'-OH and a plurality of labeled nucleotides lacking a free 3'-OH with one or more depleting reagents to generate a refined solution, wherein the one or more depleting reagents include: (i) a depletion polynucleotide and a depletion polymerase that is active to selectively incorporating the nucleotides including a free 3'-OH, wherein the depletion polynucleotide is free in solution; or (ii) one or more nucleotide cyclases that is active to selectively cyclize the nucleotides including a free 3'-OH; (b) inactivating the depletion polymerase or the one or more nucleotide cyclases; (c) contacting a sequencing primer annealed to a target polynucleotide with the refined solution and detecting the label of the incorporated labeled nucleotide lacking a free 3'-OH; and repeating step (c), wherein the sequencing errors is reduced relative to a control (e.g., the same composition without contacting one or more depleting reagents). In embodiments, the one or more sequencing errors includes a carry forward error. In embodiments, the carry forward error is reduced relative to a control.

In embodiments, the carry forward error is less than 0.2% for the plurality of sequencing cycles (e.g., 100, 150, 200, 250, 300, or more sequencing cycles). In embodiments, the carry forward error is less than 0.15% for the plurality of sequencing cycles (e.g., 100, 150, 200, 250, 300, or more sequencing cycles). In embodiments, the carry forward error is less than 0.1% for the plurality of sequencing cycles (e.g., 100, 150, 200, 250, 300, or more sequencing cycles). In embodiments, the carry forward error is less than 0.05% for the plurality of sequencing cycles (e.g., 100, 150, 200, 250, 300, or more sequencing cycles). In embodiments, the carry forward error is 0.2% for the plurality of sequencing cycles (e.g., 100, 150, 200, 250, 300, or more sequencing cycles). In embodiments, the carry forward error is 0.15% for the plurality of sequencing cycles (e.g., 100, 150, 200, 250, 300, or more sequencing cycles). In embodiments, the carry forward error is 0.1% for the plurality of sequencing cycles (e.g., 100, 150, 200, 250, 300, or more sequencing cycles). In embodiments, the carry forward error is 0.05% for the plurality of sequencing cycles (e.g., 100, 150, 200, 250, 300, or more sequencing cycles). In embodiments, the carry forward error is not greater than 0.2% for the plurality of sequencing cycles (e.g., 100, 150, 200, 250, 300, or more sequencing cycles). In embodiments, the carry forward error is not greater than 0.15% for the plurality of sequencing cycles (e.g., 100, 150, 200, 250, 300, or more sequencing cycles). In embodiments, the carry forward error is not greater than 0.1% for the plurality of sequencing cycles (e.g., 100, 150, 200, 250, 300, or more sequencing cycles). In embodiments, the carry forward error is not greater than 0.05% for the plurality of sequencing cycles (e.g., 100, 150, 200, 250, 300, or more sequencing cycles).

EXAMPLES

Example 1. Depleting Nucleotide Impurities

Sequencing-by-synthesis (SBS) methodologies employ serial incorporation and detection of labeled nucleotide analogues. For example, high-throughput SBS technology uses cleavable fluorescent nucleotide reversible terminator (NRT) sequencing chemistry. Nucleotides (e.g., A, C, G, T, and/or U) are modified by attaching a unique cleavable fluorophore to the specific location of the nucleobase and capping the 3'-OH group of the nucleotide sugar with a small reversible moiety (also referred to herein as a reversible terminator) so that they are still recognized by DNA polymerase as substrates. The reversible terminator temporarily halts the polymerase reaction after nucleotide incorporation while the fluorophore signal is detected. After incorporation and signal detection, the fluorophore and the reversible terminator are cleaved to resume the polymerase reaction in the next cycle. Ensemble-based SBS includes sequencing collections of identical sequences (i.e., monoclonal clusters of amplicons) and determining their sequence by synthesis of the complement in a stepwise, synchronous fashion. This results in an average sequence signal from all the amplicons present in a cluster per incorporation event.

A challenge of using reversible terminators in NGS technologies is the presence of impurities, such as natural nucleotides or non-reversible terminator-containing nucleotides. DNA polymerases generally discriminate against modified nucleotides in favor of 3'-OH bearing nucleotide counterparts when presented as a mixture. This typically leads to the clusters of monoclonal amplicons being out-of-phase, reducing sequencing accuracy and limiting sequencing read lengths. Long read lengths require an effective solution to the synchrony problems in ensemble-based SBS. One such phase loss effect relates to an "incomplete extension" (IE) event or error (also referred to herein as a "lag error"). An IE event may occur as a result of a failure of a sequencing reaction to incorporate one or more nucleotide species into one or more nascent molecules for a given extension round of the sequence, for example, which may result in subsequent reactions being at a sequence position that is out of phase with the sequence position for the majority of the population (e.g., certain template extensions fall behind the main template population). IE events may arise, for example, due to a lack of nucleotide availability to a portion of the template/polymerase complexes of a population. Alternatively, or in addition, IE events may be caused by a defective or absent polymerase, or an incorporated nucleotide that does not have a 3' OH available (e.g., retains a reversible terminator) for nucleotide polymerization.

Another such phase loss effect relates to a "carry forward" (CF) event or error (also referred to herein as a "lead error"). A CF event may occur as a result of an improper additional extension of a nascent molecule by incorporation of one or more nucleotide species in a sequence or strand position that is ahead and thus out of phase with the sequence or strand position of the rest of the population. CF events may arise, for example, because of the misincorporation of a nucleotide species, or in certain instances, because of contamination from nucleotides remaining from a previous cycle (e.g., which may result from an insufficient or incomplete washing of the reaction chamber). For example, a small fraction of a "dT" nucleotide cycle may be present or carry forward to a "dC" nucleotide cycle. The presence of both nucleotides may lead to an undesirable extension of a fraction of the growing strands where the "dT" nucleotide is incorporated in addition to the "dC" nucleotide such that multiple different nucleotide incorporations events take place where only a single type of nucleotide incorporation would normally be expected. Alternatively, some strands may extend faster when the reversible terminator of the nucleotide to be incorporated is removed prematurely, or the solution of reversibly terminated nucleotides contains impurities (e.g., natural nucleotides or modified nucleotides bearing a 3' hydroxyl group). CF events may also arise because of a polymerase error (e.g., there may be an improper incorporation of a nucleotide species into the nascent molecule that is not complementary to the nucleotide species on the template molecule).

Errors or phasing issues related to IE and CF events (alternatively referred to as phasing and/or prephasing errors) may be exacerbated over time because of the accumulation of such events, which may cause degradation of sequence signal or quality over time and an overall reduction in the practical read length of the system (e.g., the number of nucleotides that can be sequenced for a given template). The present disclosure reflects the discovery that sequencing performance (e.g., efficiency and/or accuracy of sequencing) may be improved by utilizing the methods described herein.

Sequencing by synthesis of nucleic acids ideally requires the controlled (i.e. one at a time), yet rapid, incorporation of the correct complementary nucleotide opposite the oligonucleotide being sequenced. For example, using nucleotides bearing a 3' reversible terminator allows for successive nucleotides to be incorporated into a polynucleotide chain in a controlled manner. Following detection, the removal of the reversible terminator leaves a free 3' hydroxyl group for addition of the next nucleotide (see FIG. 1).

Figure 2:
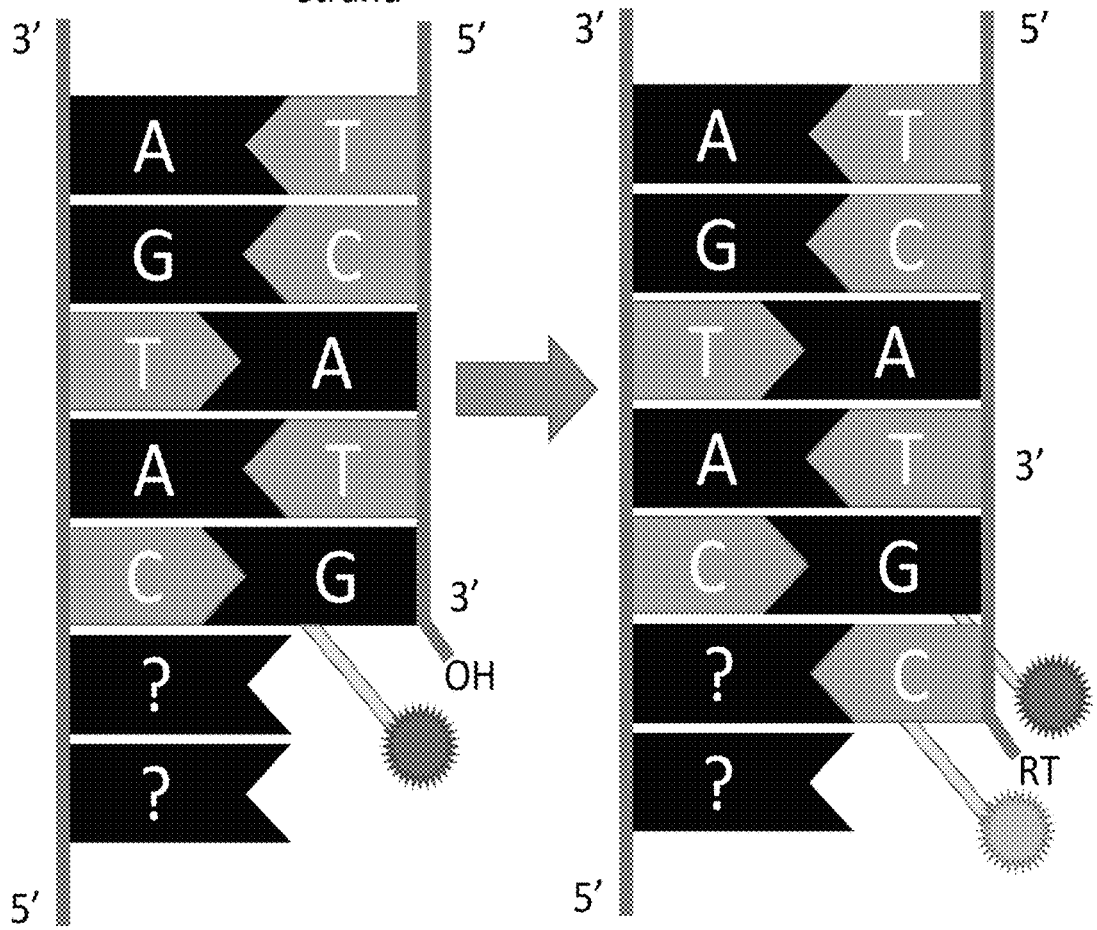
FIG. 2. A simplified depiction of an undesired out-of-phase nucleotide incorporation and detection event. The complementary strand is extended by adding a modified G nucleotide, wherein the G nucleotide contains a label, but is unterminated (i.e., does not contain a 3'-RT, rather a free 3'-OH). An additional modified nucleotide present in solution (shown as a modified C in the illustration) may then extend the complementary strand further. During the detection event, the labels for both the first incorporated nucleotide (G) and the second incorporated nucleotide (C) are detected; both labels are then removed, optionally simultaneously along with the RT. The resulting complementary strand is out of phase with the surrounding amplicons.

Typically, many polynucleotides are confined to an area of a discrete region (referred to as a cluster) and are synchronized in their nucleotide incorporation and detection. For example, at the start of a sequencing reaction, after hybridization of the sequencing primer, 100% of the strands within the cluster are synchronized. As the strands are extended, individual strands may fall behind or extend faster than the majority of the strands. This loss of synchronization is amplified as the number of sequencing rounds increases and eventually, the background noise from the unsynchronized strands becomes too great to accurately call the correct base. Some strands may extend faster when the reversible terminator of the nucleotide to be incorporated is removed prematurely, or the solution of reversibly terminated nucleotides contains impurities (e.g., natural nucleotides or modified nucleotides bearing a 3' hydroxyl group), resulting in the clusters of monoclonal amplicons being out-of-phase. For example, see FIG. 2 for an overview of the undesired process.

Without a reversible terminator present on the nucleotide, an additional nucleotide is capable of being incorporated and detected, resulting in dephasing from surrounding amplicons in the cluster. This asynchronization event results in a lower quality individual base calls and less accurate sequencing reads. The nucleotide solutions and methods described herein results in faster SBS cycle times, lower out-of-phase values, and permit longer sequencing read lengths.

Improvements to modified nucleotide stability or methods of removing unterminated nucleotides from nucleotide solutions remains a challenge. Impurities may be present immediately following manufacturing and purification. Although high-performance liquid chromatography (HPLC) can purify immediately following manufacturing 3'-O-modified-nucleotides, the quantity of 3'-OH bearing nucleotides remains high enough to cause asynchronization events in sequencing. Additionally, stored nucleotide solutions may degrade over time, resulting in premature cleaving of the reversible terminator, leading to an increased concentration of 3'-OH bearing nucleotides in a stored nucleotide solution.

An enzymatic mop-up strategy was described in Metzker et al (BioTechniques 25:814-817 (1998)), where streptavidin containing beads, a biotinylated primer and mop-up template is added to a solution. In the presence of a polymerase, non-terminated nucleotides are incorporated into the mop-up template. The beads containing the now incorporated non-terminated nucleotides are then isolated and discarded. The mop-up strategy was originally developed for non-labeled 3'-O-modified nucleotides. In the context of SBS, nucleotides (e.g., A, C, G, T, and/or U) are typically modified by attaching a unique fluorophore to the nucleobase and capping the 3'-OH group of the nucleotide sugar with a reversible terminator. When following the procedure outlined in Metzker, the fluorophores non-specifically interact with the streptavidin coated beads, saturating the remaining functional groups and preventing the beads from reducing the labeled non-terminated nucleotides and limiting the efficacy of this technique. Additionally, separating the beads within a microfluidic device is nontrivial and resulted in coagulated structures arresting fluid flow.

Figure 3A:
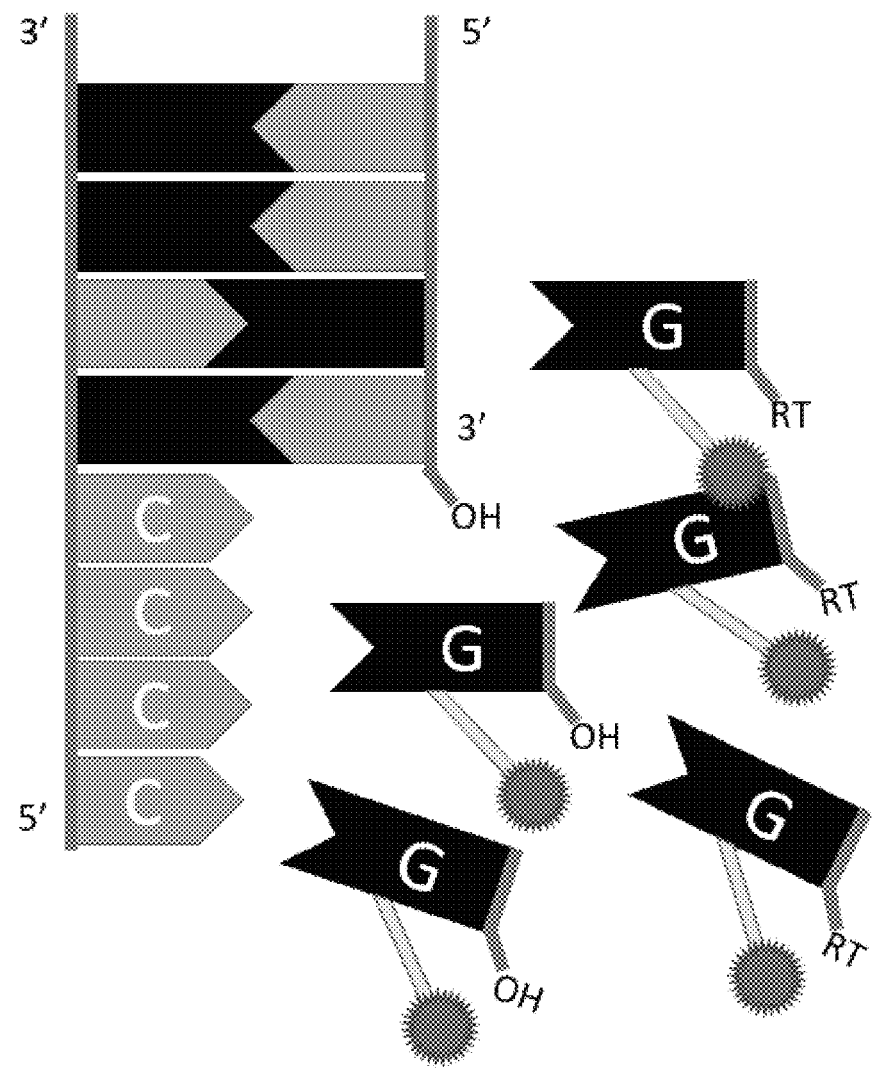
FIGS. 3A-3B. Depicted in FIG. 3A is an embodiment of removing non-terminated (i.e., nucleotides without 3'-RTs) from a nucleotide solution. The nucleotide solution includes labeled nucleotides containing a 3'-RT moiety, and nucleotides containing 3'-hydroxyl moieties. In the presence of a depletion template and a depletion polymerase not capable of incorporating modified nucleotides (e.g., Klenow), the non-terminated nucleotides are incorporated into the depletion template (not shown). The resulting depleted nucleotide solution no longer contains non-terminated nucleotides (as depicted in FIG. 3B).
Figure 3B:
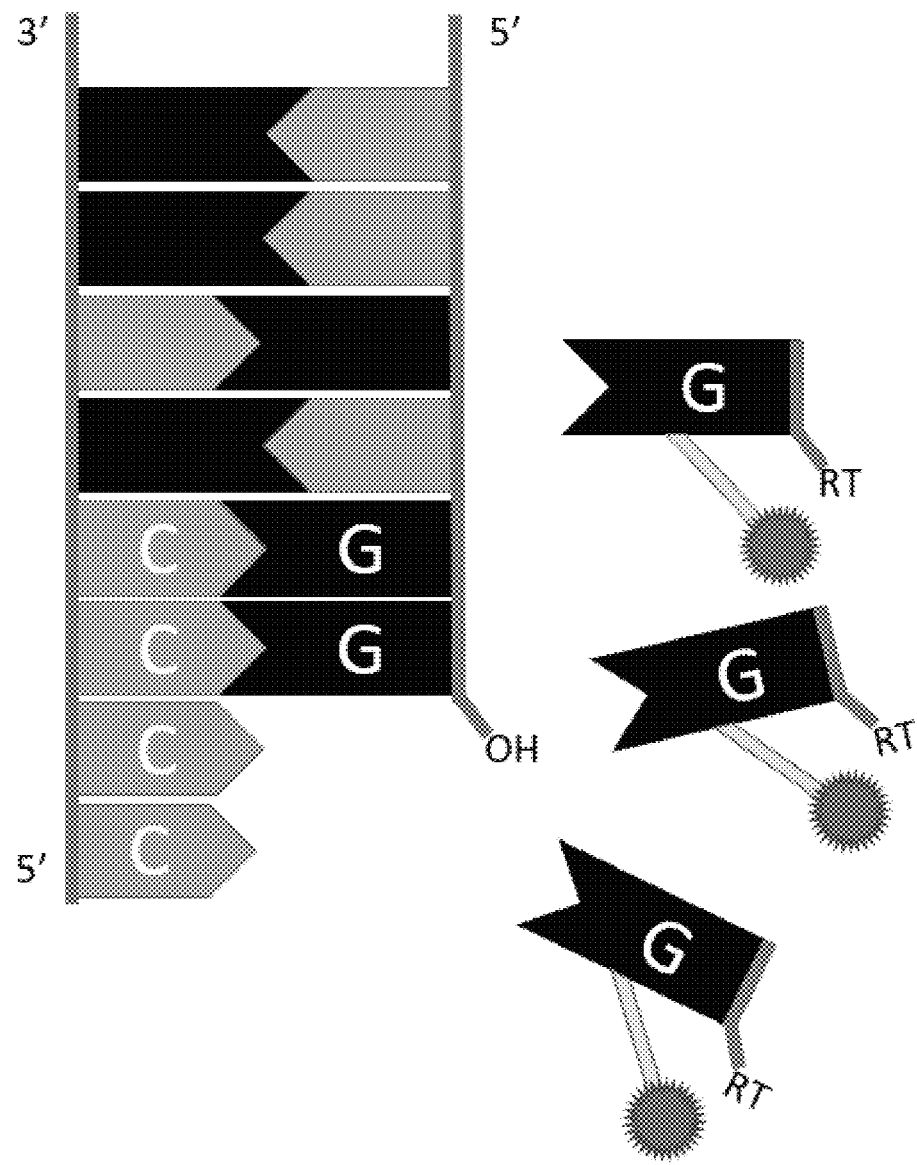

Applicants developed processes to remove non-terminated nucleotides from solutions (e.g., nucleotide solutions and sequencing solutions) capable of being used directly in a microfluidic device, such as a sequencing device, referred to herein as "live-polishing" or "nucleotide impurity depletion". For example, one method to live-polish a nucleotide solution includes incubating the solution with a depletion polymerase (e.g., Klenow (3'→5' exo-)) and an oligo template (e.g., a depletion template) in solution, depicted in FIGS. 3A-3B. While incubating, the non-terminated nucleotides (i.e., nucleotides having a 3'-OH moiety) are incorporated into the depletion template. The resulting polished nucleotide solution no longer contains non-terminated nucleotides (as depicted in FIG. 3B). Because a "live-polished" solution in accordance with some embodiments can be used directly, it does not require clean-up to remove the depletion polymerase or depletion template. As such, the beads of Metzker are not needed, and both the depletion primer and depletion template may instead be free in solution.

Alternatively, the nucleotide solution is incubated with a nucleotide cyclase. For example, incubating a nucleotide solution containing non-terminated nucleotides with an adenylyl cyclase, guanylyl cyclase, or cytidylyl cyclase converts the non-terminated nucleotides to cyclic monophosphates, rendering them non-incorporable by a sequencing enzyme in a subsequent sequencing reaction. In embodiments, the cyclase is soluble guanylyl cyclase (e.g., soluble guanylyl cyclase alpl, as described in see Beste et al *Biochemistry*. 2012; 51(1):194-204), which has both purinyl and pyrimidinyl cyclase activity and can serve to cyclize all potential nucleotides present in a nucleotide solution (e.g., A, C, G, T/U).

These depletion protocols are capable of removing non-terminated nucleotides from solutions containing a mixture of reversibly-terminated modified nucleotides and non-terminated nucleotides, and can be implemented immediately after manufacturing and purifying the modified nucleotides. For example, a nucleotide solution containing the necessary components for live-polishing may then be stored in a vessel (e.g., stored at 4° C.) and is continually removing non-terminated nucleotides from the solution as they form within the vessel. Live-polishing continues while the nucleotide solution is stored until ready to be used in a microfluidic device, which often is weeks to months following initial nucleotide production. Live-polishing may allow an extension of the expiration date relative to non-polished nucleotide solutions, and may also allow expired nucleotide solutions to be salvaged and used in a sequencing reaction. The quantity of non-terminated nucleotides is reduced relative to a non live-polished nucleotide solution.

Alternatively, a sequencing solution (e.g., a nucleotide solution contained in a commercial kits) may also be live-polished while being used on a microfluidic device. For example, a commercial kit containing a sequencing solution may be mixed with a depletion enzyme in a microfluidic device, prior to entry into a flow cell. In embodiments, the solution is mixed with a depletion enzyme while in transit to the flow cell. In embodiments, the solution is mixed with a depletion enzyme and maintained at a suitable reaction temperature, prior to entry into the flow cell. Importantly, this process can be performed within a microfluidic device, such as a sequencing instrument such that all contaminating non-terminated modified nucleotides are removed from the solution immediately prior to a sequencing event.

The presence of the depletion enzyme does not negatively affect the sequencing quality. Upon entry into the flow cell, which contains a nucleic acid to be sequenced and typically includes clusters of nucleic acids to be sequenced, the solution (e.g., nucleotide solution or sequencing solution) contains a depletion enzyme. The reaction temperatures for a sequencing reaction may inactivate the depletion enzyme. Moreover, the depletion enzyme is selected such that it is incapable of incorporating 3'-O-modified nucleotides so if it is active at the sequencing reaction temperatures it is not competitive with the sequencing enzyme (i.e., an enzyme which is capable of incorporating 3'-O-modified nucleotides).

To establish the depletion protocol, each labeled reversibly-terminated nucleotide (C, T, A, and G) solution is isolated in separate containers. Alternatively, a nucleotide solution containing a mixture of all four labeled reversibly-terminated nucleotides with C, T, A, and G nucleotides may be used. The methods and solutions described herein are applicable to any reversibly terminated nucleotide, for example, at the 3' position of the nucleotide and may be a chemically cleavable moiety such as an allyl group, an azidomethyl group or a methoxymethyl group, or may be an enzymatically cleavable group such as a phosphate ester. For the purposes of this experiment we used reversible terminated nucleotides described in U.S. Pat. No. 10,738,072, which is incorporated herein by reference for all purposes. To each nucleotide solution, 40 μL of Klenow buffer and 8 μL of a specific depletion oligonucleotide template is added. The sequences of the depletion oligonucleotide templates are described in Table 2. The depletion oligonucleotide templates are each self-priming hairpins with a 5'-overhang with a poly(N) sequence, where N is T, G, C, or A. For example, the G-capture depletion oligonucleotide template has a $(C)_{15}$ 5'-overhang such that when added to a nucleotide solution containing non-terminated (i.e., free 3'-OH) deoxyguanosine triphosphate (dGTP) nucleotides they are incorporated by the depletion enzyme into the G-capture template; this is partially illustrated in FIGS. 3A-3B. Alternatively, a primer can anneal to the depletion template. Note, to minimize any secondary structures and ease depletion oligonucleotide template synthesis for the C-capture depletion oligonucleotide template, the 5'-overhang terminates with a poly-T tail. Klenow exo- is added to each nucleotide solution and incubated at 37° C. for about 90 minutes. The depleted nucleotide solutions were then quantified and stored at 4° C.

TABLE 2

Depletion oligonucleotide templates

| Oligo name | Sequence |
|---|---|
| A-capture (SEQ ID NO: 1) | 5'-TTTTTTTTTTTTTTTGGAGGTGACAGGTTTTTCCT GTCACCTCC-3' |
| C-capture (SEQ ID NO: 2) | 5'-TTTGGGGGGGGGACGTGACAGGTTTTTCCTGTCAC CTCC-3' |
| G-capture (SEQ ID NO: 3) | 5'-CCCCCCCCCCCCCCCGGAGGTGACAGGTTTTTCCT GTCACCTCC-3' |
| T-capture (SEQ ID NO: 4) | 5'-AAAAAAAAAAAAAAAGGAGGTGACAGGTTTTTCCT GTCACCTCC-3' |

Experiments to quantify the lead percentage were carried out to determine the percent of non-terminated nucleotides in a bulk nucleotide solution. Performing the lead assay determines whether depletion has been effective in reducing the amount of non-terminated nucleotides. In this example, the efficiency of depletion in removing non-terminated nucleotides was assessed using depleted nucleotide solutions (with a dye-labeled G nucleotide) stored at either 4° C. or 37° C. for 1 day, 3 days, or 1 week to simulate depletion during long-term nucleotide storage, with fresh Klenow enzyme added at time 0. An additional set of tests were included wherein supplemental depletion oligonucleotide template was added to the depleted nucleotide solution at time 0. All tests were performed in duplicate.

The lead assay was performed in a streptavidin-coated multi-well plate. Template nucleic acids were bound to streptavidin-coated beads, and the bead-template complexes were then attached to the bottom of each well, with a single template present per well. The lead extension enzyme was diluted in incorporation buffer, and 40 uL of the enzyme solution was added to each well to pre-bind the enzyme to the template/primer duplex. The lead extension enzyme does not accept modified nucleotides (i.e., does not incorporate reversibly-terminated nucleotides). The plates were then incubated for 5 minutes at 65° C. Wells were then washed and imaged.

As described supra, the depleted nucleotide solutions tested were stored at either 4° C. or 37° C. for 1 day, 3 days, or 1 week prior to use in the lead assay. A nucleotide solution which had not live-polished was used as a no-storage control. Prior to testing, the nucleotide solutions were pre-warmed at 55° C. Nucleotide solutions were added to each well and incubated at 55° C. for 10 minutes. The wells were then washed with EDTA Wash Buffer to inactivate the enzyme, and the wells were imaged.

Figure 4A:
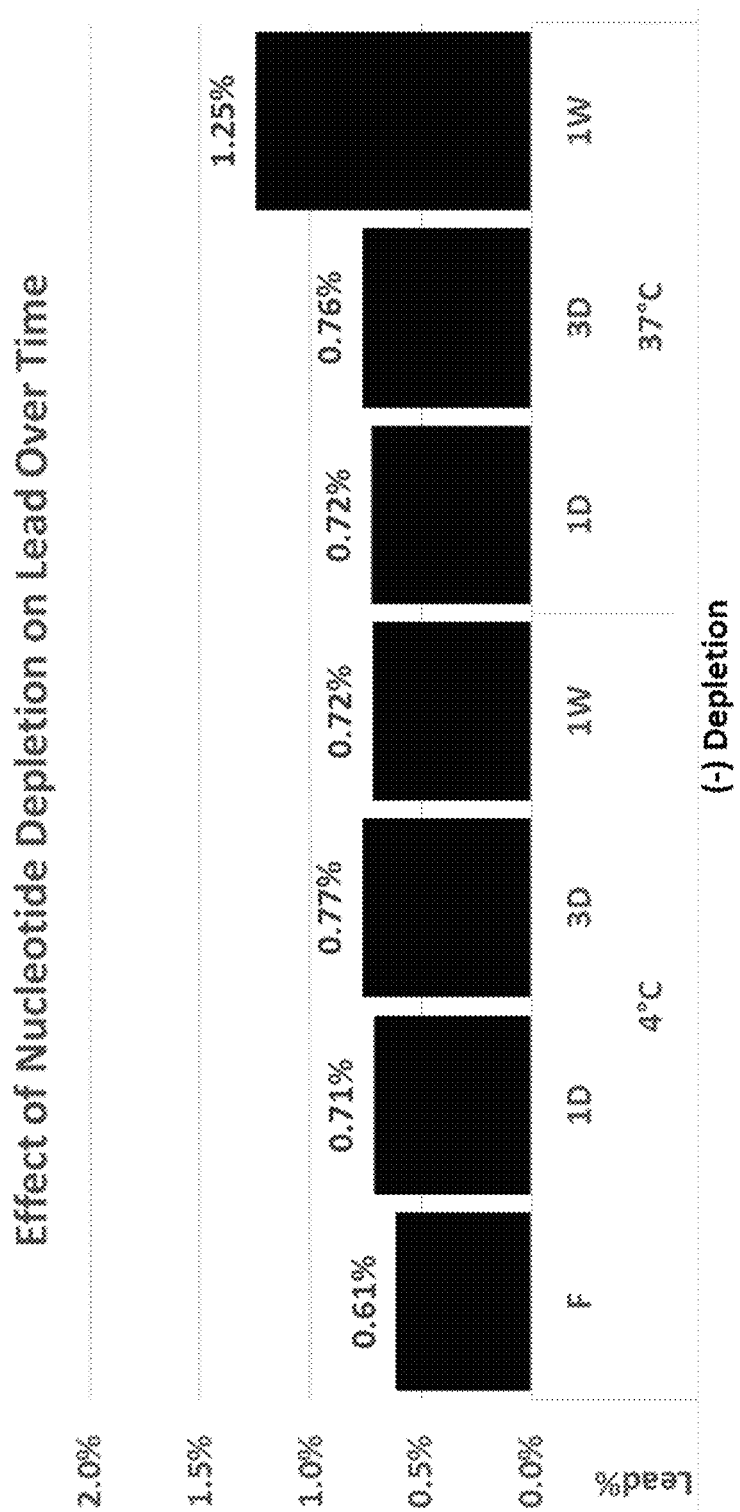

Results for the experiment assessing the effect of depletion on lead over time are summarized in FIG. 4. Generally, storing the non-depleted modified nucleotides (reported as (−) Depletion in FIG. 4A) results in approximately 0.1% lead increase relative to a fresh nucleotide solution, referred to as "F" in FIG. 4A. Unpolished modified nucleotide solutions are stable at 4° C. and maintain approximately 0.73% lead for 1-day, 3-day, and 7-day old nucleotide solutions. Storing the unpolished modified nucleotides at 37° C., however, results in a dramatic increase in lead over time. The lead % increases from 0.72% to 1.25% following a week of storage at 37° C., as reported in FIG. 4A.

With the depletion protocols as described herein, the lead % is significantly reduced. For example, storing the polished modified nucleotides (reported as (+) Depletion in FIG. 4B) at both 4° C. and 37° C. results in approximately 0.19% lead for 1-day, 3-day, and 7-day old nucleotide solutions. Taken together, these results show a benefit from live-polishing on the reduction in non-terminated nucleotides across a range of storage conditions. For a solution containing 2000 modified nucleotides stored at 37° C. for at least a week without polishing, approximately 25 of the modified nucleotides will not contain a reversible terminator. In contrast when live polished nucleotide solutions are used, a solution containing 2000 modified nucleotides stored at 37° C. for at least a week, approximately 4 of the modified nucleotides will not contain a reversible terminator.

Example 2. Depletion Enzyme in a Sequencing Reaction

Figure 5:
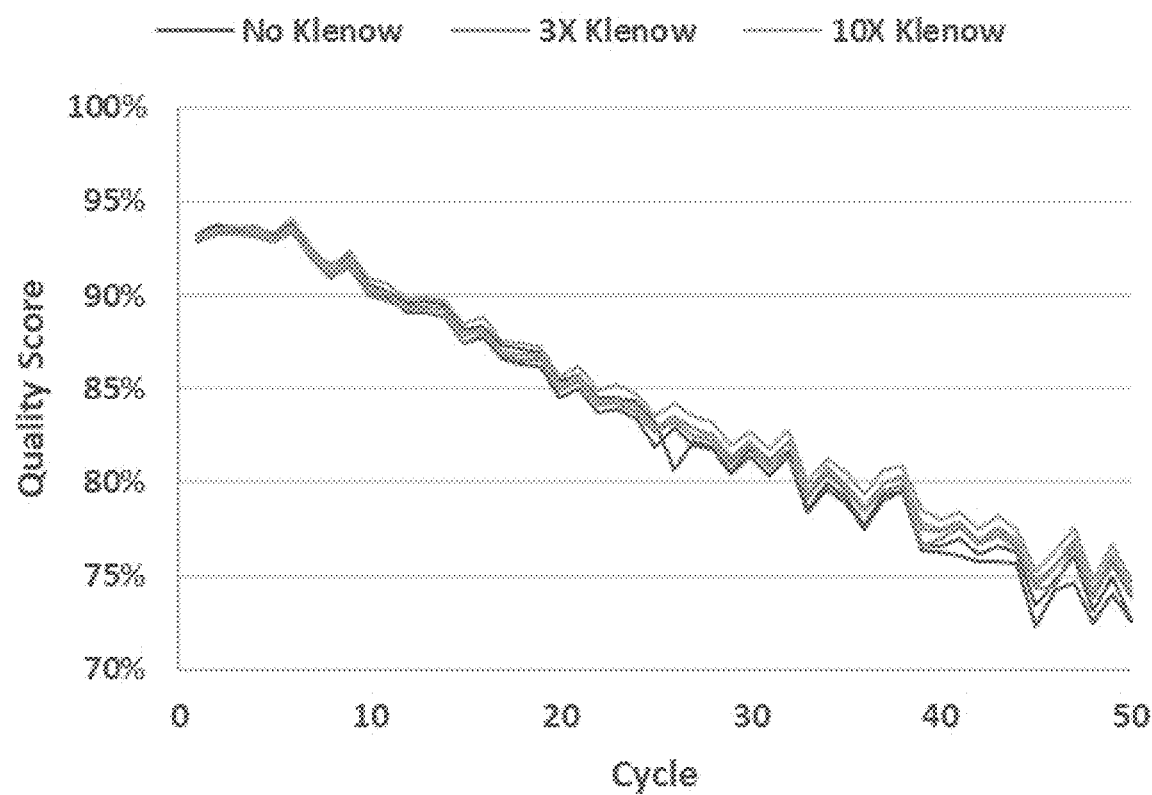
FIG. 5. The quality score plotted per cycle of nucleotide incorporation from a 50-cycle sequencing run comparing no Klenow enzyme to a 3× and 10× concentration of Klenow enzyme.

A 50-cycle sequencing run was conducted in the presence of various concentrations of a depletion enzyme. Nucleic acid templates were hybridized to surface immobilized primers. A sequencing solution containing components necessary for sequencing, including a nucleotide solution containing labeled reversibly-terminated nucleotides, a buffer, salts (e.g., magnesium sulfate, potassium chloride) was mixed with a depletion polymerase, Klenow Fragment (3'→5' exo-) (NEB Catalog #M0407B) and depletion templates. The concentrations of the depletion polymerase were varied: 0 μL, 120 μL, and 400 μL of a stock solution containing 5U/μL, corresponding to control, 3× (0.00204 U/ul), and 10× (0.0068 U/ul) depletion enzyme concentrations. Following a 50-cycle sequencing experiment at different concentrations of a depletion enzyme, no significant difference in the quality score was observed (see FIG. 5). Taken together with the results presented in Example 1, depletion is effective at reducing non-terminated nucleotide populations, and the presence of depletion components (e.g., Klenow enzyme) does not impact sequencing quality during a sequencing reaction.

Modified nucleotides that contain a unique cleavably-linked fluorophore and a reversible-terminating moiety capping the 3'-OH group, for example, those described in U.S. 2017/0130051, WO 2017/058953, WO 2019/164977, and U.S. Pat. No. 10,738,072, have shown sensitivity to cysteines present in sequencing polymerases. The cysteines normally form a disulfide bridge, however in the presence of sequencing solutions and conditions, the disulfide bridge may break to form two reactive thiols. These thiols may act to prematurely cleave the linker and/or reversible terminator, acting as a weak reducing agent, increasing asynchronous shifts in sequencing runs that are detrimental to sequencing accuracy. Protocols were adjusted to remove any thiol containing reagents. For example, enzymes are commonly stored in DTT (referred to as dithiothreitol and/or Clelands reagent) which is used to stabilize enzymes and other proteins.

There is a need for a depletion polymerase that has reduced interference with the modified nucleotides used in sequencing applications. Provided herein are novel polymerases wherein the cysteine amino acid was mutated (C584S in SEQ ID NO:5). While serine was chosen as an initial mutation, any amino acid that eliminates the ability to form free thiols and does not perturb the stability nor function of the polymerase is envisioned (e.g., glycine, threonine, selenocysteine or alanine). Variants lacking a cysteine were capable of incorporating nucleotides, and advantageously, the remaining modified nucleotides exhibited greater stability (i.e., did not prematurely deblock or lose the detectable moiety) relative to a polymerase that contained one or more cysteines.

```
The wild-type enzyme has the sequence (SEQ ID NO: 5):
VISYDNYVTILDEETLKAWIAKLEKAPVFAFDTETDSLDNISANLVGLSFAIEPGVAA

YIPVAHDYLDAPDQISRERALELLKPLLEDEKALKVGQNLKYDRGILANYGIELRGIA

FDTMLESYILNSVAGRHDMDSLAERWLKHKTITFEEIAGKGKNQLTFNQIALEEAGR

YAAEDADVTLQLHLKMWPDLQKHKGPLNVFENIEMPLVPVLSRIERNGVKIDPKVL

HNHSEELTLRLAELEKKAHEIAGEEFNLSSTKQLQTILFEKQGIKPLKKTPGGAPSTSE

LSSTDPNLQNIPVRNEEGRRIRQAFIAPEDYVIVSADYSQIELRIMAHLSRDKGLLTAF

AEGKDIHRATAAEVFGLPLETVTSEQRRSAKAINFGLIYGMSAFGLARQLNIPRKEAQ

KYMDLYFERYPGVLEYMERTRAQAKEQGYVETLDGRRLYLPDIKSSNGARRAAAE

RAAINAPMQGTAADIIKRAMIAVDAWLQAEQPRVRMIMQVHDELVFEVHKDDVDA

VAKQIHQLMENCTRLDVPLLVEVGSGENWDQAH.

The in-house mutant includes the sequence (SEQ ID NO: 6):
MVISYDNYVTILDEETLKAWIAKLEKAPVFAFATATDSLDNISANLVGLSFAIEPGVA

AYIPVAHDYLDAPDQISRERALELLKPLLEDEKALKVGQNLKYDRGILANYGIELRGI

AFDTMLESYILNSVAGRHDMDSLAERWLKHKTITFEEIAGKGKNQLTFNQIALEEAG

RYAAEDADVTLQLHLKMWPDLQKHKGPLNVFENIEMPLVPVLSRIERNGVKIDPKV

LHNHSEELTLRLAELEKKAHEIAGEEFNLSSTKQLQTILFEKQGIKPLKKTPGGAPSTS

EEVLEELALDYPLPKVILEYRGLAKLKSTYTDKLPLMINPKTGRVHTSYHQAVTATG

RLSSTDPNLQNIPVRNEEGRRIRQAFIAPEDYVIVSADYSQIELRIMAHLSRDKGLLTA

FAEGKDIHRATAAEVFGLPLETVTSEQRRSAKAINFGLIYGMSAFGLARQLNIPRKEA

QKYMDLYFERYPGVLEYMERTRAQAKEQGYVETLDGRRLYLPDIKSSNGARRAAA

ERAAINAPMQGTAADIIKRAMIAVDAWLQAEQPRVRMIMQVHDELVFEVHKDDVD

AVAKQIHQLMENSTRLDVPLLVEVGSGENWDQAH.
```

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

P-Embodiments

The present disclosure provides the following illustrative embodiments.

Embodiment P1. A composition comprising: (a) nucleotides comprising a free 3'-OH, (b) nucleotides lacking a free 3'-OH, and (c) one or more reagents for decreasing the amount of the nucleotides comprising a free 3'-OH, wherein the one or more reagents comprise: (i) a depletion primer, a depletion template, and a depletion polymerase that is active to extend the depletion primer along the depletion template by selectively incorporating the nucleotides comprising a free 3'-OH, wherein the depletion primer and the depletion template are free in solution; or (ii) one or more nucleotide cyclases active to selectively cyclize the nucleotides comprising a free 3'-OH.

Embodiment P2. The composition of Embodiment P1, wherein the nucleotides lacking a free 3'-OH comprise a reversible terminator moiety.

Embodiment P3. The composition of Embodiment P1 or Embodiment P2, wherein the nucleotides lacking a free 3'-OH comprise a detectable label.

Embodiment P4. The composition of Embodiment P3, wherein the nucleotides lacking a free 3'-OH comprise a plurality of different nucleotides that are differently labeled.

Embodiment P5. The composition of any one of Embodiment P1-Embodiment P4, wherein the depletion template comprises a homopolymer sequence.

Embodiment P6. The composition of any one of Embodiment P1-Embodiment P5, wherein the depletion primer and the depletion template are portions of a single polynucleotide comprising a hairpin structure and a 5' overhang.

Embodiment P7. The composition of any one of Embodiment P1-Embodiment P6, wherein the composition comprises the depletion polymerase, and the nucleotides lacking a free 3'-OH comprise a modification that blocks strand incorporation by the depletion polymerase.

Embodiment P8. The composition of any one of Embodiment P1-Embodiment P7, wherein the depletion polymerase is active at a temperature of about 2° C.-65° C., about 2° C.-10° C., or about 4° C.-37° C.

Embodiment P9. The composition of any one of Embodiment P1-Embodiment P8, wherein the depletion polymerase is not thermostable above 65° C.

Embodiment P10. The composition of any one of Embodiment P1-Embodiment P9, wherein the depletion polymerase comprises a Klenow fragment.

Embodiment P11. The composition of any one of Embodiment P1-Embodiment P10, further comprising a sequencing primer, a target polynucleotide, and a sequencing polymerase, wherein the sequencing polymerase is active to extend the sequencing primer along the target polynucleotide by incorporating one of the nucleotides lacking a free 3'-OH.

Embodiment P12. The composition of any one of Embodiment P1-Embodiment P11, wherein the composition is in a sequencing flow cell.

Embodiment P13. The composition of any one of Embodiment P1-Embodiment P4, Embodiment P11, or Embodiment P12, wherein the nucleotide cyclase is a soluble guanylyl cyclase.

Embodiment P14. A method of sequencing a target polynucleotide, the method comprising: (a) incubating the target polynucleotide in a reaction mixture comprising a sequencing primer, nucleotides comprising a free 3'-OH, nucleotides lacking a free 3'-OH, and a sequencing polymerase; (b) enzymatically decreasing the amount of the nucleotides comprising a free 3'-OH; (c) extending the sequencing primer along the target polynucleotide using the sequencing polymerase by incorporating one of the nucleotides lacking a free 3'-OH; and (d) identifying the incorporated nucleotide.

Embodiment P15. The method of Embodiment P14, wherein enzymatically decreasing the amount of the nucleotides comprising a free 3'-OH comprises a depletion polymerase extending a depletion primer along a depletion template by selectively incorporating the nucleotides comprising a free 3'-OH.

Embodiment P16. The method of Embodiment P14 or Embodiment P15, wherein the nucleotides lacking a free 3'-OH comprise a reversible terminator moiety.

Embodiment P17. The method of any one of Embodiment P14-Embodiment P16, wherein the nucleotides lacking a free 3'-OH comprise a detectable label.

Embodiment P18. The method of Embodiment P17, wherein the nucleotides lacking a free 3'-OH comprise a plurality of different nucleotides that are differently labeled.

Embodiment P19. The method of any one of Embodiment P15-Embodiment P18, wherein the depletion template comprises a homopolymer sequence.

Embodiment P20. The method of any one of Embodiment P15-Embodiment P19, wherein the depletion primer and the depletion template are portions of a single polynucleotide comprising a hairpin structure and a 5' overhang.

Embodiment P21. The method of any one of Embodiment P15-Embodiment P20, wherein the nucleotides lacking a free 3'-OH comprise a modification that blocks strand incorporation by the depletion polymerase.

Embodiment P22. The method of any one of Embodiment P15-Embodiment P21, wherein the depletion polymerase is active at a temperature of about 2° C.-65° C., about 2° C.-10° C., or about 4° C.-37° C.

Embodiment P23. The method of any one of Embodiment P15-Embodiment P22, wherein the depletion polymerase is not thermostable above 65° C.

Embodiment P24. The method of any one of Embodiment P15-Embodiment P23, wherein the depletion polymerase comprises a Klenow fragment.

Embodiment P25. The method of any one of Embodiment P14-Embodiment P24, wherein steps (a)-(d) are performed in a sequencing flow cell.

Embodiment P26. The method of any one of Embodiment P14, Embodiment P16-Embodiment P18, or Embodiment P25, wherein the enzymatically decreasing the amount of the nucleotides comprising a free 3'-OH comprises selectively cyclizing the nucleotides comprising the free 3'-OH using a nucleotide cyclase.

Embodiment P27. The method of Embodiment P26, wherein the nucleotide cyclase is a soluble guanylyl cyclase.

Embodiment P28. A method of increasing storage stability of modified nucleotides for use in a sequencing reaction, the method comprising: (a) storing the modified nucleotides in solution at about 2° C.-65° C. for at least 12 hours, wherein the modified nucleotides comprise nucleotides lacking a free 3'-OH, and wherein the solution comprises nucleotides comprising a free 3'-OH; and (b) depleting the nucleotides comprising a free 3'-OH during said storing, wherein said depleting comprises: (i) extending a depletion primer along a depletion template using a depletion polymerase that selectively incorporates the nucleotides comprising a free 3'-OH, wherein the depletion primer and the depletion template are free in solution; or (ii) selectively cyclizing the nucleotides comprising the free 3'-OH using a nucleotide cyclase.

Embodiment P29. The method of Embodiment P28, wherein the nucleotides lacking a free 3'-OH comprise a reversible terminator moiety.

Embodiment P30. The method of Embodiment P28 or Embodiment P29, wherein the nucleotides lacking a free 3'-OH comprise a detectable label.

Embodiment P31. The method of Embodiment P30, wherein the nucleotides lacking a free 3'-OH comprise a plurality of different nucleotides that are differently labeled.

Embodiment P32. The method of any one of Embodiment P28-Embodiment P31, wherein the depletion template comprises a homopolymer sequence.

Embodiment P33. The method of any one of Embodiment P28-Embodiment P32, wherein the depletion primer and the depletion template are portions of a single polynucleotide comprising a hairpin structure and a 5' overhang.

Embodiment P34. The method of any one of Embodiment P28-Embodiment P33, wherein the nucleotides lacking a free 3'-OH comprise a modification that blocks strand incorporation by the depletion polymerase.

Embodiment P35. The method of any one of Embodiment P28-Embodiment P34, wherein said storing is at about 2° C.-8° C., about 20° C.-30° C., or about 4° C.-37° C.

Embodiment P36. The method of any one of Embodiment P28-Embodiment P35, wherein said storing is for at least 1 day, 2 days, 3 days, or 7 days.

Embodiment P37. The method of Embodiment P36 wherein said storing is at about 2° C.-8° C. for at least 1 day.

Embodiment P38. The method of Embodiment P36 wherein said storing is at about 20° C.-30° C. for at least 1 day.

Embodiment P39. The method of any one of Embodiment P28-Embodiment P38, wherein the depletion polymerase is not thermostable above 65° C.

Embodiment P40. The method of any one of Embodiment P28-Embodiment P39, wherein the depletion polymerase comprises a Klenow fragment.

Embodiment P41. The method of any one of Embodiment P28-Embodiment P31 or Embodiment P35-Embodiment P38, wherein the nucleotide cyclase is a soluble guanylyl cyclase.

Embodiment P42. The method of any one of Embodiment P28-Embodiment P41, the method further comprising sequencing a target polynucleotide in a reaction mixture, wherein the reaction mixture comprises the target polynucleotide, a sequencing primer, a sequencing polymerase, and at least a portion of the stored solution of modified nucleotides.

Embodiment P43. The method of Embodiment P42, wherein the portion of the stored solution of modified nucleotides is an unfractionated portion of the stored solution.

Additional Embodiments

The present disclosure provides the following additional illustrative embodiments.

Embodiment 1. A method of sequencing a target polynucleotide, said method comprising: (a) generating a refined solution by contacting a composition comprising a plurality of labeled nucleotides comprising a free 3'-OH and a plurality of labeled nucleotides lacking a free 3'-OH with one or more depleting reagents, wherein the one or more depleting reagents comprise: (i) one or more depletion polynucleotides and a depletion polymerase that is active to selectively incorporate the nucleotides comprising a free 3'-OH, wherein the depletion polynucleotide is free in solution; or (ii) one or more nucleotide cyclases that is active to selectively cyclize the nucleotides comprising a free 3'-OH; (b) inactivating the depletion polymerase or the one or more nucleotide cyclases; and (c) contacting a sequencing primer annealed to a target polynucleotide with the refined solution and detecting the label of the incorporated labeled nucleotide lacking a free 3'-OH.

Embodiment 2. The method of embodiment 1, further comprising repeating step (c).

Embodiment 3. The method of embodiment 1 or 2, wherein inactivating the depletion polymerase or the one or more nucleotide cyclases comprises heat inactivation or chemical inactivation.

Embodiment 4. The method of any one of embodiments 1 to 3, wherein the depletion polymerase comprises a Klenow fragment, or mutant thereof.

Embodiment 5. The method of any one of embodiments 1 to 3, wherein the depletion polymerase is a Klenow fragment or mutant thereof, soluble guanylyl cyclase or mutant thereof, or a terminal deoxynucleotidyl transferase (TdT).

Embodiment 6. The method of any one of embodiments 1 to 3, wherein the depletion polymerase is active at a temperature of about 1° C. to about 45° C.

Embodiment 7. The method of any one of embodiments 1 to 3, wherein the depletion polymerase is active at a temperature of about 4° C. to about 37° C.

Embodiment 8. The method of any one of embodiments 1 to 3, wherein the depletion polymerase is not active above a temperature of about 45° C.

Embodiment 9. The method of any one of embodiments 1 to 8, wherein the one or more depletion polynucleotides comprise a homopolymer sequence.

Embodiment 10. The method of any one of embodiments 1 to 8, wherein the one or more depletion polynucleotides comprises a single polynucleotide comprising a hairpin structure and a 5' overhang.

Embodiment 11. The method of any one of embodiments 1 to 8, wherein the one or more depletion polynucleotides comprises a depletion primer annealed to a depletion template.

Embodiment 12. The method of any one of embodiments 1 to 11, wherein generating a refined solution occurs at a first temperature range of about 1° C. to about 45° C.

Embodiment 13. The method of any one of embodiments 1 to 12, further comprising increasing the temperature to a second temperature range and reducing the activity of the depletion polymerase.

Embodiment 14. The method of any one of embodiments 1 to 13, wherein the nucleotides lacking a free 3'-OH comprise a reversible terminator moiety.

Embodiment 15. The method of any one of embodiments 1 to 14, wherein the labeled nucleotide lacking a free 3'-OH has the formula:

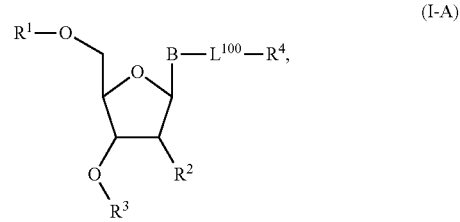

(I-A)

wherein $R^1$ is a polyphosphate moiety, monophosphate moiety, or —OH; $R^2$ is hydrogen or —OH; $R^3$ is a reversible terminator moiety; $R^4$ is a detectable moiety; B is a divalent cytosine or a derivative thereof, divalent guanine or a derivative thereof, divalent adenine or a derivative thereof, divalent thymine or a derivative thereof, divalent uracil or a derivative thereof, divalent hypoxanthine or a derivative thereof, divalent xanthine or a derivative thereof, divalent 7-methylguanine or a derivative thereof, divalent 5,6-dihydrouracil or a derivative thereof, divalent 5-methylcytosine or a derivative thereof, or divalent 5-hydroxymethylcytosine or a derivative thereof, and $L^{100}$ is a divalent linker.

Embodiment 16. The method of any one of embodiments 1 to 15, wherein the labeled nucleotide comprising a free 3'-OH has the formula:

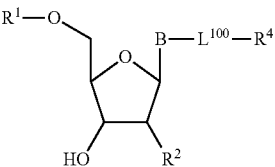

(II-A), wherein $R^1$ is a polyphosphate moiety, monophosphate moiety, or —OH; $R^2$ is hydrogen or —OH; $R^4$ is a detectable moiety; B is a divalent cytosine or a derivative thereof, divalent guanine or a derivative thereof, divalent adenine or a derivative thereof, divalent thymine or a derivative thereof, divalent uracil or a derivative thereof, divalent hypoxanthine or a derivative thereof, divalent xanthine or a derivative thereof, divalent 7-methylguanine or a derivative thereof, divalent 5,6-dihydrouracil or a derivative thereof, divalent 5-methylcytosine or a derivative thereof, or divalent 5-hydroxymethylcytosine or a derivative thereof; and $L^{100}$ is a divalent linker.

Embodiment 17. The method of embodiment 15 or 16, wherein $L^{100}$ is a cleavable linker.

Embodiment 18. The method of any one of embodiments 15 to 17, wherein $R^1$ is a triphosphate moiety.

Embodiment 19. The method of any one of embodiments 15 to 18, wherein $R^2$ is hydrogen.

Embodiment 20. The method of any one of embodiments 14 to 19, wherein the reversible terminator comprises an azido moiety, a disulfide moiety, or an alkoxyalkyl moiety.

Embodiment 21. A method of depleting labeled nucleotides comprising a free 3'-OH in a composition comprising (i) labeled nucleotides comprising a free 3'-OH and (ii) labeled nucleotides lacking a free 3'-OH, said method comprising: incubating the composition with a depletion polymerase at a first temperature range of about 1° C. to about 45° C., wherein the depletion polymerase is free in solution and capable of depleting the labeled nucleotides comprising a free 3'-OH in the composition by selectively incorporating the nucleotides comprising a free 3'-OH into one or more depletion polynucleotides; or selectively cyclizing the nucleotides comprising a free 3'-OH with a one or more nucleotide cyclases.

Embodiment 22. The method of embodiment 21, further comprising incorporating one or more labeled nucleotides lacking a free 3'-OH into a sequencing primer hybridized to a target polynucleotide.

Embodiment 23. The method of embodiment 22, further comprising detecting the one or more labeled nucleotides.

Embodiment 24. The method of any one of embodiments 21 to 23, wherein prior to incubating the composition is stored for at least 1 day, at least 2 days, at least 3 days, or at least 7 days.

Embodiment 25. The method of any one of embodiments 21 to 23, wherein prior to incubating the composition is stored for about 1 week, about 2 weeks, about 3 weeks, about 4 weeks, about 5 weeks, about 6 weeks, about 7 weeks, or about 8 weeks.

Embodiment 26. The method of any one of embodiments 21 to 23, wherein prior to incubating the composition is stored for about 1 month, about 2 months, about 3 months, about 4 months, about 5 months, about 6 months, about 7 months, about 8 months, about 9 months, about 10 months, about 11 months, or about 12 months.

Embodiment 27. The method of any one of embodiments 24 to 26, wherein the composition is stored at about 2° C.-8° C., about 20° C.-30° C., or about 4° C.-37° C.

Embodiment 28. The method of any one of embodiments 21 to 27, further comprising inactivating the depletion polymerase or the one or more nucleotide cyclases.

Embodiment 29. The method of embodiment 28, wherein inactivating the depletion polymerase or the one or more nucleotide cyclases comprises heat inactivation or chemical inactivation.

Embodiment 30. The method of any one of embodiments 21 to 29, wherein the depletion polymerase comprises a Klenow fragment, or mutant thereof.

Embodiment 31. The method of any one of embodiments 21 to 29, wherein the depletion polymerase is a Klenow fragment or mutant thereof, soluble guanylyl cyclase or mutant thereof, or a terminal deoxynucleotidyl transferase (TdT).

Embodiment 32. The method of any one of embodiments 21 to 29, wherein the depletion polymerase is active at a temperature of about 1° C. to about 45° C.

Embodiment 33. The method of any one of embodiments 21 to 29, wherein the depletion polymerase is active at a temperature of about 4° C. to about 37° C.

Embodiment 34. The method of any one of embodiments 21 to 29, wherein the depletion polymerase is not active above a temperature of about 45° C.

Embodiment 35. The method of any one of embodiments 21 to 34, wherein the one or more depletion polynucleotides comprise a homopolymer sequence.

Embodiment 36. The method of any one of embodiments 21 to 34, wherein the one or more depletion polynucleotides comprises a single polynucleotide comprising a hairpin structure and a 5' overhang.

Embodiment 37. The method of any one of embodiments 21 to 34, wherein the depletion polynucleotide comprises depletion primer annealed to a depletion template.

Embodiment 38. The method of any one of embodiments 21 to 37, further comprising increasing the temperature to a second temperature range and reducing the activity of the depletion enzyme.

Embodiment 39. The method of any one of embodiments 21 to 38, wherein the nucleotides lacking a free 3'-OH comprise a reversible terminator moiety.

Embodiment 40. The method of any one of embodiments 21 to 39, wherein the labeled nucleotide lacking a free 3'-OH has the formula:

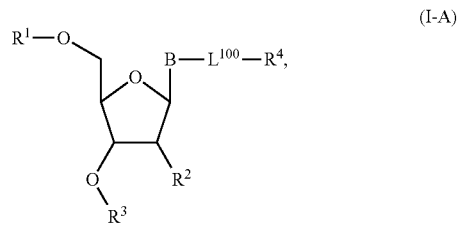

(I-A)

wherein $R^1$ is a polyphosphate moiety, monophosphate moiety, or —OH; $R^2$ is hydrogen or —OH; $R^3$ is a reversible terminator moiety; $R^4$ is a detectable moiety; B is a divalent cytosine or a derivative thereof, divalent guanine or a derivative thereof, divalent adenine or a derivative thereof, divalent thymine or a derivative thereof, divalent uracil or a derivative thereof, divalent hypoxanthine or a derivative thereof, divalent xanthine or a derivative thereof, divalent 7-methylguanine or a derivative thereof, divalent 5,6-dihydrouracil or a derivative thereof, divalent 5-methylcytosine or a derivative thereof, or divalent 5-hydroxymethylcytosine or a derivative thereof, and $L^{100}$ is a divalent linker.

Embodiment 41. The method of any one of embodiments 21 to 40, wherein the labeled nucleotide comprising a free 3'-OH has the formula:

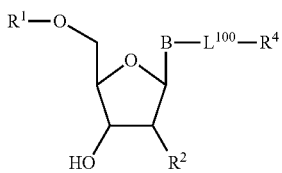

(II-A), wherein $R^1$ is a polyphosphate moiety, monophosphate moiety, or —OH; $R^2$ is hydrogen or —OH; $R^4$ is a detectable moiety; B is a divalent cytosine or a derivative thereof, divalent guanine or a derivative thereof, divalent adenine or a derivative thereof, divalent thymine or a derivative thereof, divalent uracil or a derivative thereof, divalent hypoxanthine or a derivative thereof, divalent xanthine or a derivative thereof, divalent 7-methylguanine or a derivative thereof, divalent 5,6-dihydrouracil or a derivative thereof, divalent 5-methylcytosine or a derivative thereof, or divalent 5-hydroxymethylcytosine or a derivative thereof; and $L^{100}$ is a divalent linker.

Embodiment 42. The method of embodiment 40 or 41, wherein $L^{100}$ is a cleavable linker.

Embodiment 43. The method of any one of embodiments 40 to 42, wherein $R^1$ is a triphosphate moiety.

Embodiment 44. The method of any one of embodiments 40 to 43, wherein $R^2$ is hydrogen.

Embodiment 45. The method of any one of embodiments 39 to 44, wherein the reversible terminator comprises an azido moiety, a disulfide moiety, or an alkoxyalkyl moiety.

Embodiment 46. A composition comprising: (a) labeled nucleotides comprising a free 3'-OH, (b) labeled nucleotides lacking a free 3'-OH, and (c) one or more depleting reagents for decreasing the amount of the nucleotides comprising a free 3'-OH, wherein the one or more depleting reagents comprise: (i) one or more depletion polynucleotides and a depletion polymerase that is active to selectively incorporating the nucleotides comprising a free 3'-OH, wherein the depletion polynucleotide is free in solution; or (ii) one or more nucleotide cyclases active to selectively cyclize the nucleotides comprising a free 3'-OH.

Embodiment 47. The composition of embodiment 46, wherein the composition is stored in a single container.

Embodiment 48. The composition of embodiment 46 or 47, wherein the composition is stored at about 2° C.-8° C., about 20° C.-30° C., or about 4° C.-37° C.

Embodiment 49. The composition of embodiment 46 or 47, wherein the composition is stored at about 4° C. to about 30° C.

Embodiment 50. The composition of any one of embodiments 46 to 49, wherein the depletion polymerase comprises a Klenow fragment, or mutant thereof.

Embodiment 51. The composition of any one of embodiments 46 to 49, wherein the depletion polymerase is a Klenow fragment or mutant thereof, soluble guanylyl cyclase or mutant thereof, or a terminal deoxynucleotidyl transferase (TdT).

Embodiment 52. The composition of any one of embodiments 46 to 49, wherein the depletion polymerase is active at a temperature of about 1° C. to about 45° C.

Embodiment 53. The composition of any one of embodiments 46 to 49, wherein the depletion polymerase is active at a temperature of about 4° C. to about 37° C.

Embodiment 54. The composition of any one of embodiments 46 to 49, wherein the depletion polymerase is not active above a temperature of about 45° C.

Embodiment 55. The composition of any one of embodiments 46 to 54, wherein the one or more depletion polynucleotides comprise a homopolymer sequence.

Embodiment 56. The composition of any one of embodiments 46 to 54, wherein the one or more depletion polynucleotides comprises a single polynucleotide comprising a hairpin structure and a 5' overhang.

Embodiment 57. The composition of any one of embodiments 46 to 53, wherein the one or more depletion polynucleotides comprises depletion primer annealed to a depletion template.

Embodiment 58. The composition of any one of embodiments 46 to 57, further comprising increasing the temperature to a second temperature range and reducing the activity of the depletion enzyme.

Embodiment 59. The composition of any one of embodiments 46 to 57, wherein the nucleotides lacking a free 3'-OH comprise a reversible terminator moiety.

Embodiment 60. The composition of any one of embodiments 46 to 59, wherein the labeled nucleotide lacking a free 3'-OH has the formula:

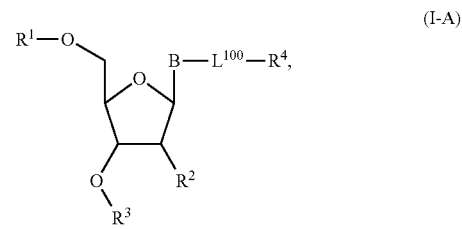

(I-A)

wherein $R^1$ is a polyphosphate moiety, monophosphate moiety, or —OH; $R^2$ is hydrogen or —OH; $R^3$ is a reversible terminator moiety; $R^4$ is a detectable moiety; B is a divalent cytosine or a derivative thereof, divalent guanine or a derivative thereof, divalent adenine or a derivative thereof, divalent thymine or a derivative thereof, divalent uracil or a derivative thereof, divalent hypoxanthine or a derivative thereof, divalent xanthine or a derivative thereof, divalent 7-methylguanine or a derivative thereof, divalent 5,6-dihydrouracil or a derivative thereof, divalent 5-methylcytosine or a derivative thereof, or divalent 5-hydroxymethylcytosine or a derivative thereof, and $L^{100}$ is a divalent linker.

Embodiment 61. The composition of any one of embodiments 46 to 60, wherein the labeled nucleotide comprising a free 3'-OH has the formula:

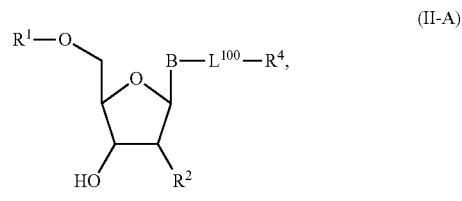

(II-A)

wherein $R^1$ is a polyphosphate moiety, monophosphate moiety, or —OH; $R^2$ is hydrogen or —OH; $R^4$ is a detectable moiety; B is a divalent cytosine or a derivative thereof, divalent guanine or a derivative thereof, divalent adenine or a derivative thereof, divalent thymine or a derivative thereof, divalent uracil or a derivative thereof, divalent hypoxanthine or a derivative thereof, divalent xanthine or a derivative thereof, divalent 7-methylguanine or a derivative thereof, divalent 5,6-dihydrouracil or a derivative thereof, divalent 5-methylcytosine or a derivative thereof, or divalent 5-hydroxymethylcytosine or a derivative thereof, and $L^{100}$ is a divalent linker.

Embodiment 62. The composition of embodiment 60 or 61, wherein $L^{100}$ is a cleavable linker.

Embodiment 63. The composition of any one of embodiments 60 to 62, wherein $R^1$ is a triphosphate moiety.

Embodiment 64. The composition of any one of embodiments 60 to 63, wherein $R^2$ is hydrogen.

Embodiment 65. The composition of any one of embodiments 59 to 64, wherein the reversible terminator comprises an azido moiety, a disulfide moiety, or an alkoxyalkyl moiety.

Embodiment 66. A kit comprising the composition of any one of embodiments 46 to 65.

Embodiment 67. A microfluidic device for sequencing a target polynucleotide, comprising: i) a reaction vessel for receiving a composition of any one of embodiments 46 to 65; ii) one or more reservoirs comprising the composition of any one of embodiments 46 to 65; iii) flow paths from each reservoir to the reaction vessel; and iv) a fluidics controller that controls the flow from the reservoir to the reaction vessel.

Embodiment 68. A method of increasing the shelf life of a composition comprising modified nucleotides, the method comprising: (a) storing the composition of any one of embodiments 46 to 65 at about 1° C. to about 40° C. for one or more minutes; and (b) depleting the labeled nucleotides comprising a free 3'-OH during said storing, wherein said depleting comprises: (i) incorporating with a depleting polymerase the nucleotides comprising a free 3'-OH into one or more depletion polynucleotides in solution; or (ii) selectively cyclizing the nucleotides comprising the free 3'-OH using a nucleotide cyclase; wherein depleting the nucleotides comprising a free 3'-OH increases the shelf life of the kit comprising modified nucleotides relative to a control.

Embodiment 69. A method of decreasing one or more sequencing errors in a plurality of sequencing cycles, said method comprising: (a) contacting a composition comprising a plurality of labeled nucleotides comprising a free 3'-OH and a plurality of labeled nucleotides lacking a free 3'-OH with one or more depleting reagents to generate a refined solution, wherein the one or more depleting reagents comprise: (i) a depletion polynucleotide and a depletion polymerase that is active to selectively incorporating the nucleotides comprising a free 3'-OH, wherein the depletion polynucleotide is free in solution; or (ii) one or more nucleotide cyclases that is active to selectively cyclize the nucleotides comprising a free 3'-OH; (b) inactivating the depletion polymerase or the one or more nucleotide cyclases; (c) contacting a sequencing primer annealed to a target polynucleotide with the refined solution and detecting the label of the incorporated labeled nucleotide lacking a free 3'-OH; and repeating step (c), wherein the sequencing errors is reduced relative to a control.

SEQUENCE LISTING

```
Sequence total quantity: 7
SEQ ID NO: 1            moltype = DNA  length = 44
FEATURE                 Location/Qualifiers
source                  1..44
                        mol_type = other DNA
                        organism = synthetic construct
SEQUENCE: 1
tttttttttt tttttggagg tgacaggttt ttcctgtcac ctcc                44

SEQ ID NO: 2            moltype = DNA  length = 39
FEATURE                 Location/Qualifiers
source                  1..39
                        mol_type = other DNA
                        organism = synthetic construct
SEQUENCE: 2
tttgggggggg ggacgtgaca ggtttttcct gtcacctcc                     39

SEQ ID NO: 3            moltype = DNA  length = 44
FEATURE                 Location/Qualifiers
source                  1..44
                        mol_type = other DNA
                        organism = synthetic construct
SEQUENCE: 3
cccccccccc cccccggagg tgacaggttt ttcctgtcac ctcc                44

SEQ ID NO: 4            moltype = DNA  length = 44
FEATURE                 Location/Qualifiers
source                  1..44
                        mol_type = other DNA
                        organism = synthetic construct
SEQUENCE: 4
aaaaaaaaaa aaaaaggagg tgacaggttt ttcctgtcac ctcc                44

SEQ ID NO: 5            moltype = AA   length = 605
FEATURE                 Location/Qualifiers
source                  1..605
                        mol_type = protein
                        organism = synthetic construct
SEQUENCE: 5
VISYDNYVTI LDEETLKAWI AKLEKAPVFA FDTETDSLDN ISANLVGLSF AIEPGVAAYI  60
PVAHDYLDAP DQISRERALE LLKPLLEDEK ALKVGQNLKY DRGILANYGI ELRGIAFDTM 120
LESYILNSVA GRHDMDSLAE RWLKHKTITF EEIAGKGKNQ LTFNQIALEE AGRYAAEDAD 180
```

```
VTLQLHLKMW PDLQKHKGPL NVFENIEMPL VPVLSRIERN GVKIDPKVLH NHSEELTLRL    240
AELEKKAHEI AGEEFNLSST KQLQTILFEK QGIKPLKKTP GGAPSTSEEV LEELALDYPL    300
PKVILEYRGL AKLKSTYTDK LPLMINPKTG RVHTSYHQAV TATGRLSSTD PNLQNIPVRN    360
EEGRRIRQAF IAPEDYVIVS ADYSQIELRI MAHLSRDKGL LTAFAEGKDI HRATAAEVFG    420
LPLETVTSEQ RRSAKAINFG LIYGMSAFGL ARQLNIPRKE AQKYMDLYFE RYPGVLEYME    480
RTRAQAKEQG YVETLDGRRL YLPDIKSSNG ARRAAAERAA INAPMQGTAA DIIKRAMIAV    540
DAWLQAEQPR VRMIMQVHDE LVFEVHKDDV DAVAKQIHQL MENCTRLDVP LLVEVGSGEN    600
WDQAH                                                                605

SEQ ID NO: 6            moltype = AA  length = 606
FEATURE                 Location/Qualifiers
source                  1..606
                        mol_type = protein
                        organism = synthetic construct
SEQUENCE: 6
MVISYDNYVT ILDEETLKAW IAKLEKAPVF AFATATDSLD NISANLVGLS FAIEPGVAAY     60
IPVAHDYLDA PDQISRERAL ELLKPLLEDE KALKVGQNLK YDRGILANYG IELRGIAFDT    120
MLESYILNSV AGRHDMDSLA ERWLKHKTIT FEEIAGKGKN QLTFNQIALE EAGRYAAEDA    180
DVTLQLHLKM WPDLQKHKGP LNVFENIEMP LVPVLSRIER NGVKIDPKVL HNHSEELTLR    240
LAELEKKAHE IAGEEFNLSS TKQLQTILFE KQGIKPLKKT PGGAPSTSEE VLEELALDYP    300
LPKVILEYRG LAKLKSTYTD KLPLMINPKT GRVHTSYHQA VTATGRLSST DPNLQNIPVR    360
NEEGRRIRQA FIAPEDYVIV SADYSQIELR IMAHLSRDKG LLTAFAEGKD IHRATAAEVF    420
GLPLETVTSE QRRSAKAINF GLIYGMSAFG LARQLNIPRK EAQKYMDLYF ERYPGVLEYM    480
ERTRAQAKEQ GYVETLDGRR LYLPDIKSSN GARRAAAERA AINAPMQGTA ADIIKRAMIA    540
VDAWLQAEQP RVRMIMQVHD ELVFEVHKDD VDAVAKQIHQ LMENSTRLDV PLLVEVGSGE    600
NWDQAH                                                                606

SEQ ID NO: 7            moltype = AA  length = 8
FEATURE                 Location/Qualifiers
source                  1..8
                        mol_type = protein
                        organism = synthetic construct
SEQUENCE: 7
DYSQIELR                                                               8
```

What is claimed is:

1. A method of sequencing, said method comprising:
   (a) contacting a sequencing solution comprising a plurality of labeled nucleotides comprising a free 3'-OH and a plurality of labeled nucleotides lacking a free 3'-OH with depleting reagents to generate a refined solution comprising a reduced amount of labeled nucleotides comprising a free 3'-OH, wherein the depleting reagents comprise
      a depletion primer hybridized to a depletion polynucleotide and a depletion polymerase capable of incorporating the nucleotides comprising a free 3'-OH into the depletion polynucleotide and incapable of incorporating labeled nucleotide triphosphates comprising a 3' reversible terminator moiety, wherein the depletion polynucleotide is free in solution;
   (b) contacting a sequencing primer annealed to a target polynucleotide with the refined solution, incorporating with a sequencing polymerase a labeled nucleotide lacking a free 3'-OH into the sequencing primer, and detecting the label of the incorporated labeled nucleotide; and
   (c) repeating (b).

2. The method of claim 1, wherein (b) comprises heating the refined solution to about 55° C. to about 65° C.

3. The method of claim 1, wherein the depletion polymerase comprises a Klenow fragment or mutant thereof.

4. The method of claim 1, wherein the depletion polynucleotide comprises a homopolymer sequence, or a single polynucleotide comprising a hairpin structure and a 5' overhang.

5. The method of claim 1, wherein (a) occurs at about 1° C. to about 45° C.

6. The method of claim 5, further comprising, after (a), increasing the temperature to about 55° C. to about 65° C.

7. The method of claim 1, wherein each of the labeled nucleotides lacking a free 3'-OH comprise a reversible terminator moiety.

8. The method of claim 7, wherein the reversible terminator moiety comprises an azido moiety, a disulfide moiety, or an alkoxyalkyl moiety.

9. The method of claim 1, wherein the labeled nucleotide lacking a free 3'-OH has the formula:

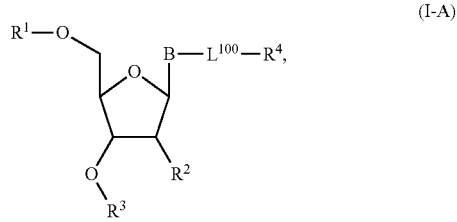

(I-A)

wherein
$R^1$ is a triphosphate moiety;
$R^2$ is hydrogen or —OH;
$R^3$ is a reversible terminator moiety;
$R^4$ is a detectable moiety;
B is a divalent cytosine or a derivative thereof, divalent guanine or a derivative thereof, divalent adenine or a derivative thereof, divalent thymine or a derivative thereof, divalent uracil or a derivative thereof, divalent hypoxanthine or a derivative thereof, divalent xanthine or a derivative thereof, divalent 7-methylguanine or a derivative thereof, divalent 5,6-dihydrouracil or a derivative thereof, divalent 5-methylcytosine or a derivative thereof, or divalent 5-hydroxymethylcytosine or a derivative thereof; and
$L^{100}$ is a divalent linker.

10. The method of claim 1, wherein the labeled nucleotide comprising a free 3'-OH has the formula:

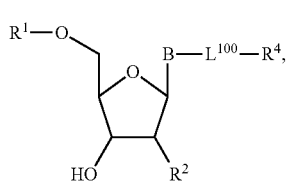

(II-A)

wherein $R^1$ is a triphosphate moiety;

$R^2$ is hydrogen or —OH;

$R^4$ is a detectable moiety;

B is a divalent cytosine or a derivative thereof, divalent guanine or a derivative thereof, divalent adenine or a derivative thereof, divalent thymine or a derivative thereof, divalent uracil or a derivative thereof, divalent hypoxanthine or a derivative thereof, divalent xanthine or a derivative thereof, divalent 7-methylguanine or a derivative thereof, divalent 5,6-dihydrouracil or a derivative thereof, divalent 5-methylcytosine or a derivative thereof, or divalent 5-hydroxymethylcytosine or a derivative thereof; and $L^{100}$ is a divalent linker.

11. The method of claim 10, wherein $L^{100}$ is a cleavable linker.

12. The method of claim 1, wherein the depletion polynucleotide comprises 2 to 30 consecutive identical nucleotides.

13. The method of claim 1, wherein the depletion polynucleotide comprises a depletion primer hybridized to a depletion template.

14. The method of claim 1, wherein the depletion polynucleotide comprises poly(A), poly(G), poly(C), and poly(T) nucleotides.

15. The method of claim 1, wherein the depletion polymerase comprises an amino acid sequence that is at least 80% identical to a continuous 500 amino acid sequence within SEQ ID NO: 5.

16. The method of claim 1, wherein the labeled nucleotides comprising a free 3'-OH and the labeled nucleotides lacking a free 3'-OH each comprise:

a first plurality of labeled adenosine triphosphates;
a second plurality of labeled thymidine triphosphates;
a third plurality of labeled guanosine triphosphates; and
a fourth plurality of labeled cytosine triphosphates.

17. The method of claim 1, wherein sequencing polymerase is mutated to favor incorporating nucleotides lacking a free 3'-OH over nucleotides comprising a free 3'-OH.

18. The method of claim 4, wherein the depletion polynucleotide is a polynucleotide comprising a hairpin structure and a 5' overhang.

19. A method of incorporating a labeled nucleotide into a sequencing primer, said method comprising:

(i) forming a refined solution comprising a reduced amount of labeled nucleotides comprising a free 3'-OH from an unrefined solution, wherein said unrefined solution comprises a labeled nucleotide comprising a 3'-OH and a labeled nucleotide comprising a 3'-reversible terminator moiety, wherein forming the refined solution comprises incorporating with a depletion polymerase the labeled nucleotide comprising a 3'-OH into a depletion primer hybridized to a depletion polynucleotide, wherein, a) the depletion polymerase is capable of incorporating a labeled nucleotide comprising a 3'-OH into the depletion polynucleotide and incapable of incorporating a labeled nucleotide comprising a 3'-reversible terminator moiety; and b) the depletion polynucleotide comprises a hairpin structure and a 5' overhang; and (ii) contacting a target polynucleotide hybridized to the sequencing primer with the refined solution and incorporating with a sequencing polymerase the labeled nucleotide sequencing comprising the 3'-reversible terminator moiety into the sequencing primer.

* * * * *